US011180559B2

(12) United States Patent
Goldenberg et al.

(10) Patent No.: US 11,180,559 B2
(45) Date of Patent: *Nov. 23, 2021

(54) SUBCUTANEOUS ANTI-HLA-DR MONOCLONAL ANTIBODY FOR TREATMENT OF HEMATOLOGIC MALIGNANCIES

(71) Applicant: Immunomedics, Inc., Morris Plains, NJ (US)

(72) Inventors: David M. Goldenberg, Mendham, NJ (US); William A. Wegener, Broomall, PA (US)

(73) Assignee: Immunomedics, Inc., Morris Plains, NJ (US)

( * ) Notice: Subject to any disclaimer, the term of this patent is extended or adjusted under 35 U.S.C. 154(b) by 661 days.

This patent is subject to a terminal disclaimer.

(21) Appl. No.: 15/868,704

(22) Filed: Jan. 11, 2018

(65) Prior Publication Data

US 2018/0162945 A1 Jun. 14, 2018

Related U.S. Application Data

(60) Continuation of application No. 15/240,052, filed on Aug. 18, 2016, now abandoned, which is a continuation-in-part of application No. 14/876,200, filed on Oct. 6, 2015, now Pat. No. 9,683,050, which is a continuation of application No. 14/163,443, filed on Jan. 24, 2014, now Pat. No. 9,180,205, which is a division of application No. 14/132,549, filed on Dec. 18, 2013, now Pat. No. 9,468,689, which is a division of application No. 13/461,307, filed on May 1, 2012, now Pat. No. 8,658,773, application No. 15/868,704, filed on Jan. 11, 2018, which is a continuation-in-part of application No. 14/630,097, filed on Feb. 24, 2015, now abandoned, which is a division of application No. 14/080,231, filed on Nov. 14, 2013, now Pat. No. 8,992,917, which is a division of application No. 12/556,718, filed on Sep. 10, 2009, now Pat. No. 8,613,903, which is a division of application No.
(Continued)

(51) Int. Cl.
| | |
|---|---|
| A61K 39/00 | (2006.01) |
| C07K 16/28 | (2006.01) |
| C07K 16/30 | (2006.01) |
| A61K 39/395 | (2006.01) |
| A61K 9/00 | (2006.01) |
| A61K 45/06 | (2006.01) |
| A61K 9/08 | (2006.01) |
| C07K 16/06 | (2006.01) |
| B82Y 5/00 | (2011.01) |

(52) U.S. Cl.
CPC ........ *C07K 16/2833* (2013.01); *A61K 9/0019* (2013.01); *A61K 9/08* (2013.01); *A61K 39/3955* (2013.01); *A61K 39/39591* (2013.01); *A61K 45/06* (2013.01); *C07K 16/065* (2013.01); *C07K 16/2803* (2013.01); *C07K 16/2851* (2013.01); *C07K 16/2887* (2013.01); *C07K 16/2896* (2013.01); *C07K 16/30* (2013.01); *C07K 16/3069* (2013.01); *A61K 2039/505* (2013.01); *A61K 2039/507* (2013.01); *A61K 2039/54* (2013.01); *A61K 2039/545* (2013.01); *A61K 2039/552* (2013.01); *B82Y 5/00* (2013.01); *C07K 2317/24* (2013.01); *C07K 2317/31* (2013.01); *C07K 2317/33* (2013.01); *C07K 2317/51* (2013.01); *C07K 2317/515* (2013.01); *C07K 2317/52* (2013.01); *C07K 2317/53* (2013.01); *C07K 2317/56* (2013.01); *C07K 2317/73* (2013.01); *C07K 2317/732* (2013.01); *C07K 2317/734* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,258,498 A | 11/1993 | Huston et al. | |

(Continued)

FOREIGN PATENT DOCUMENTS

| | | |
|---|---|---|
| EP | 0332865 | 9/1989 |
| EP | 0510949 | 10/1992 |

(Continued)

OTHER PUBLICATIONS

Edwards et al (JMB, 2003, 334: 103-118) (Year: 2003).*
(Continued)

*Primary Examiner* — G. R. Ewoldt
*Assistant Examiner* — Marianne DiBrino
(74) *Attorney, Agent, or Firm* — Richard A. Nakashima; Achim Brinker

(57) ABSTRACT

The present invention concerns compositions and methods of use of anti-HLA-DR antibodies or fragments thereof. In preferred embodiments, the antibodies are subcutaneously administered to a human patient with a hematologic cancer or autoimmune disease. The subcutaneously administered anti-HLA-DR antibody is effective to treat hematologic cancer or autoimmune disease in patients that have relapsed from or are refractory to standard therapies for hematologic cancer or autoimmune disease, such as administration of anti-CD20 antibodies, such as rituximab.

9 Claims, 29 Drawing Sheets

Specification includes a Sequence Listing.

Related U.S. Application Data

11/368,296, filed on Mar. 3, 2006, now Pat. No. 7,612,180, application No. 15/868,704, filed on Jan. 11, 2018, which is a continuation-in-part of application No. 15/353,141, filed on Nov. 16, 2016, now Pat. No. 10,174,114, which is a division of application No. 14/878,715, filed on Oct. 8, 2015, now abandoned, which is a division of application No. 14/224,866, filed on Mar. 25, 2014, now Pat. No. 9,187,561, which is a division of application No. 12/754,140, filed on Apr. 5, 2010, now Pat. No. 8,722,047, which is a continuation-in-part of application No. 12/556,718, filed on Sep. 10, 2009, now Pat. No. 8,613,903, which is a division of application No. 11/368,296, filed on Mar. 3, 2006, now Pat. No. 7,612,180.

(60) Provisional application No. 61/509,850, filed on Jul. 20, 2011, provisional application No. 61/481,489, filed on May 2, 2011, provisional application No. 62/262,692, filed on Dec. 3, 2015, provisional application No. 62/208,128, filed on Aug. 21, 2015, provisional application No. 60/657,695, filed on Mar. 3, 2005, provisional application No. 61/166,809, filed on Apr. 6, 2009, provisional application No. 61/168,715, filed on Apr. 13, 2009.

(56) References Cited

U.S. PATENT DOCUMENTS

| | | |
|---|---|---|
| 5,429,746 A | 7/1995 | Shadle et al. |
| 5,484,892 A | 1/1996 | Tedder et al. |
| 5,530,101 A | 6/1996 | Queen et al. |
| 5,585,089 A | 12/1996 | Queen et al. |
| 5,593,676 A | 1/1997 | Bhat et al. |
| 5,618,920 A | 4/1997 | Robinson et al. |
| 5,665,595 A | 9/1997 | Petell et al. |
| 5,686,072 A | 11/1997 | Uhr et al. |
| 5,693,762 A | 12/1997 | Queen et al. |
| 5,728,369 A | 3/1998 | Griffiths et al. |
| 5,736,137 A | 4/1998 | Anderson et al. |
| 5,776,456 A | 7/1998 | Anderson et al. |
| 5,789,554 A | 8/1998 | Leung et al. |
| 5,792,852 A | 8/1998 | Do Couto |
| 5,795,967 A | 8/1998 | Aggarwal et al. |
| 5,846,534 A | 12/1998 | Waldmann et al. |
| 5,859,205 A | 1/1999 | Adair et al. |
| 5,876,961 A | 3/1999 | Crowe et al. |
| 6,051,228 A | 4/2000 | Aruffo et al. |
| 6,051,230 A | 4/2000 | Thorpe et al. |
| 6,171,586 B1 | 1/2001 | Lam et al. |
| 6,180,370 B1 | 1/2001 | Queen et al. |
| 6,180,377 B1 | 1/2001 | Morgan et al. |
| 6,187,287 B1 | 2/2001 | Leung et al. |
| 6,252,055 B1 | 6/2001 | Relton |
| 6,306,393 B1 | 10/2001 | Goldenberg et al. |
| 6,416,958 B2 | 7/2002 | Vidovic |
| 6,605,279 B2 | 8/2003 | Freeman et al. |
| 6,645,493 B1 | 11/2003 | Bucala et al. |
| 6,653,104 B2 | 11/2003 | Goldenberg et al. |
| 6,676,924 B2 | 1/2004 | Hansen et al. |
| 6,730,300 B2 | 5/2004 | Leung et al. |
| 6,870,034 B2 | 3/2005 | Breece et al. |
| 6,893,639 B2 | 5/2005 | Levy et al. |
| 6,991,790 B1 | 1/2006 | Lam et al. |
| 7,022,500 B1 | 4/2006 | Queen et al. |
| 7,038,017 B2 | 5/2006 | Rinderknecht et al. |
| 7,074,403 B1 | 7/2006 | Goldenberg et al. |
| 7,109,304 B2 | 9/2006 | Hansen et al. |
| 7,138,496 B2 | 11/2006 | Hua et al. |
| 7,151,164 B2 | 12/2006 | Hansen et al. |
| 7,238,785 B2 | 7/2007 | Govindan et al. |
| 7,251,164 B2 | 7/2007 | Okhonin et al. |
| 7,262,278 B2 | 8/2007 | Tawara et al. |
| 7,282,567 B2 | 10/2007 | Goldenberg et al. |
| 7,300,655 B2 | 11/2007 | Hansen et al. |
| 7,312,318 B2 | 12/2007 | Hansen et al. |
| 7,385,040 B2 | 6/2008 | Johansson et al. |
| 7,387,773 B2 | 6/2008 | Murray et al. |
| 7,435,803 B2 | 10/2008 | Hansen et al. |
| 7,521,056 B2 | 4/2009 | Chang et al. |
| 7,521,531 B2 | 4/2009 | Govindan |
| 7,527,787 B2 | 5/2009 | Chang et al. |
| 7,534,431 B2 | 5/2009 | McBride et al. |
| 7,534,866 B2 | 5/2009 | Chang et al. |
| 7,541,440 B2 | 6/2009 | Goldenberg et al. |
| 7,550,143 B2 | 6/2009 | Chang et al. |
| 7,585,491 B2 | 9/2009 | Govindan |
| 7,592,004 B2 | 9/2009 | Kaisheva et al. |
| 7,612,180 B2 | 11/2009 | Goldenberg et al. |
| 7,625,560 B2 | 12/2009 | Basi et al. |
| 7,635,473 B2 | 12/2009 | Warne et al. |
| 7,666,400 B2 | 2/2010 | Chang et al. |
| 7,772,373 B2 | 8/2010 | Hansen et al. |
| 7,820,161 B1 | 10/2010 | Curd et al. |
| 7,829,064 B2 | 11/2010 | Griffiths et al. |
| 7,829,525 B2 | 11/2010 | Frevert |
| 7,847,071 B2 | 12/2010 | Bonnerjea et al. |
| 7,858,070 B2 | 12/2010 | Chang et al. |
| 7,863,426 B2 | 1/2011 | Wan et al. |
| 7,871,622 B2 | 1/2011 | Chang et al. |
| 7,892,547 B2 | 2/2011 | McBride et al. |
| 7,901,680 B2 | 3/2011 | Chang et al. |
| 7,906,118 B2 | 3/2011 | Chang et al. |
| 7,906,121 B2 | 3/2011 | Chang et al. |
| 7,919,087 B2 | 4/2011 | Hansen et al. |
| 7,931,903 B2 | 4/2011 | Hansen et al. |
| 8,067,006 B2 | 11/2011 | Govindan et al. |
| 8,097,252 B2 | 1/2012 | McBride et al. |
| 8,211,440 B2 | 7/2012 | Chang et al. |
| 8,246,960 B2 | 8/2012 | Chang et al. |
| 8,268,317 B2 | 9/2012 | Govindan et al. |
| 8,287,864 B2 * | 10/2012 | Goldenberg ....... A61K 39/3955 424/133.1 |
| 8,338,140 B2 | 12/2012 | Govindan et al. |
| 8,343,460 B2 | 1/2013 | McBride et al. |
| 8,343,496 B2 | 1/2013 | Griffiths et al. |
| 8,361,464 B2 | 1/2013 | Griffiths et al. |
| 8,383,081 B2 | 2/2013 | Hansen et al. |
| 8,481,003 B2 | 7/2013 | Griffiths et al. |
| 8,613,903 B2 * | 12/2013 | Goldenberg ....... A61K 47/6849 424/1.11 |
| 8,865,176 B2 | 10/2014 | Chang et al. |
| 8,913,903 B2 | 12/2014 | Hamaya et al. |
| 8,992,917 B2 | 3/2015 | Goldenberg et al. |
| 9,180,205 B2 | 11/2015 | Zeng et al. |
| 9,187,561 B2 | 11/2015 | Goldenberg et al. |
| 9,468,689 B2 | 10/2016 | Zeng et al. |
| 9,493,573 B2 * | 11/2016 | Govindan .......... C07K 16/3007 |
| 9,522,959 B2 * | 12/2016 | Govindan .......... C07K 16/3023 |
| 9,963,516 B2 * | 5/2018 | Zeng .................... A61K 9/0019 |
| 10,058,621 B2 * | 8/2018 | Goldenberg ....... A61K 31/4375 |
| 10,174,114 B2 * | 1/2019 | Goldenberg ........... C07K 16/28 |
| 10,206,918 B2 * | 2/2019 | Govindan .......... A61K 31/4184 |
| 10,799,597 B2 * | 10/2020 | Goldenberg ............ A61P 35/04 |
| 2001/0014326 A1 | 8/2001 | Andya et al. |
| 2002/0018749 A1 | 2/2002 | Hudson et al. |
| 2002/0041847 A1 | 4/2002 | Goldenberg |
| 2003/0004094 A1 | 1/2003 | Ghose et al. |
| 2003/0007968 A1 | 1/2003 | Larsen et al. |
| 2003/0013122 A1 | 1/2003 | Bucala et al. |
| 2003/0103979 A1 | 6/2003 | Leung et al. |
| 2003/0211498 A1 | 11/2003 | Morin et al. |
| 2004/0033228 A1 | 2/2004 | Krause et al. |
| 2004/0033561 A1 | 2/2004 | O'Keefe et al. |
| 2004/0208870 A1 | 10/2004 | Allan |
| 2005/0013820 A1 | 1/2005 | Holoshitz et al. |
| 2005/0053666 A1 | 3/2005 | Tzannis et al. |
| 2005/0112126 A1 | 5/2005 | Baca et al. |
| 2005/0118167 A1 | 6/2005 | Okada et al. |
| 2005/0180975 A1 | 8/2005 | Hanna |
| 2006/0152846 A1 | 7/2006 | Krause et al. |

(56) References Cited

U.S. PATENT DOCUMENTS

| | | |
|---|---|---|
| 2006/0193850 A1 | 8/2006 | Warne et al. |
| 2006/0210475 A1 | 9/2006 | Goldenberg et al. |
| 2007/0031402 A1 | 2/2007 | Zhang et al. |
| 2007/0073047 A1 | 3/2007 | Kandasamy et al. |
| 2007/0184050 A1 | 8/2007 | Ishikawa et al. |
| 2007/0258981 A1 | 11/2007 | Hilbert et al. |
| 2008/0064856 A1 | 3/2008 | Warne et al. |
| 2008/0146507 A1 | 6/2008 | Bucala et al. |
| 2008/0152658 A1 | 6/2008 | Dagan et al. |
| 2008/0306247 A1 | 12/2008 | Mizushima et al. |
| 2009/0068196 A1 | 3/2009 | Goldbach et al. |
| 2009/0104184 A1 | 4/2009 | Flemming et al. |
| 2009/0117111 A1 | 5/2009 | Aukerman et al. |
| 2009/0202487 A1 | 8/2009 | Chang et al. |
| 2009/0239259 A1 | 9/2009 | Hsieh |
| 2009/0269302 A1 | 10/2009 | Salfeld et al. |
| 2009/0291062 A1 | 11/2009 | Fraunhofer et al. |
| 2009/0300780 A1 | 12/2009 | Cattaneo et al. |
| 2010/0034738 A1 | 2/2010 | Goldenberg et al. |
| 2010/0074885 A1 | 3/2010 | Schiff et al. |
| 2010/0158899 A1 | 6/2010 | Andya et al. |
| 2010/0172862 A1 | 7/2010 | Correia et al. |
| 2010/0189721 A1 | 7/2010 | Brisbane et al. |
| 2010/0196267 A1 | 8/2010 | Goldenberg et al. |
| 2010/0209434 A1 | 8/2010 | Bishop et al. |
| 2010/0221187 A1 | 9/2010 | Lieberburg et al. |
| 2010/0226884 A1 | 9/2010 | Chang et al. |
| 2010/0260766 A1 | 10/2010 | Srivastava et al. |
| 2010/0278822 A1 | 11/2010 | Fraunhofer et al. |
| 2010/0303827 A1 | 12/2010 | Sharma et al. |
| 2011/0020328 A1 | 1/2011 | Brisbane et al. |
| 2011/0070225 A1 | 3/2011 | Goldbach et al. |
| 2011/0071054 A1 | 3/2011 | Simard |
| 2011/0071276 A1 | 3/2011 | Simard |
| 2011/0305631 A1 | 12/2011 | Govindan et al. |
| 2012/0039914 A1 | 2/2012 | Bucala et al. |

FOREIGN PATENT DOCUMENTS

| | | |
|---|---|---|
| WO | 9113974 | 9/1991 |
| WO | 94/29451 | 12/1994 |
| WO | 9427638 | 12/1994 |
| WO | 9505468 | 2/1995 |
| WO | 9804281 | 2/1998 |
| WO | 98/50435 | 11/1998 |
| WO | 9954440 | 10/1999 |
| WO | 00/67795 | 11/2000 |
| WO | 0067796 | 11/2000 |
| WO | 00/74718 | 12/2000 |
| WO | 2006094192 | 9/2006 |
| WO | WO 2006/094192 A2 * | 9/2006 |
| WO | 2007103469 | 9/2007 |
| WO | 2008028946 | 3/2008 |
| WO | 2008137915 | 11/2008 |
| WO | 2009006301 | 1/2009 |
| WO | 2009138484 | 11/2009 |
| WO | 2010011697 | 1/2010 |
| WO | 2012/151199 | 12/2012 |

OTHER PUBLICATIONS

Lloyd et al (Protein Engineering, Eng. Design & Selection, 2009, 22(3): 159-168) (Year: 2009).*
Goel et al (J. Immunol., 2004, 173: 7358-7367) (Year: 2004).*
Khan and Salunke (J. Immunol, 2014, 192: 5398-5405) (Year: 2014).*
Poosarla et al (Biotechn. Bioeng., 2017, 114(6): 1331-1342) (Year: 2017).*
Torres and Casadevall (Trend. Immunol., 2008, 29(2): 91-97) (Year: 2008).*
Gupta et al (Blood 2009, 114(22): 3738) (Year: 2009).*
Goldenberg et al (Blood 2016, 128(22): 3958) (Year: 2016).*
Anderson et al (J. Clin. Microbiol.1986, 23(3): 475-480) (Year: 1986).*
Shi et al (JIM, 2006, 314: 9-20) (Year: 2006).*
Bates and Power. (Antibodies, 2019, 8 (28): 1-31) (Year: 2019).*
Millennium 2007 (Year: 2007).*
Almasri et al (Am. J. Hematol. 1992, 40: 259-263) (Year: 1992).*
Abdel-Raheem et al., "Severe Evans's syndrome secondary to interleukin-2 therapy: treatment with chimeric monoclonal anti-CD20 antibody", Ann Hematol. Sep. 2001;80(9):543-5.
Bendig, M., "Humanization of Rodent Monoclonal Antibodies by CDR Grafting", Academic Press Inc., New York, NY, vol. 8, (1995), pp. 83-93.
Burgess et al., "Possible dissociation of the heparin-binding and mitogenic activities of heparin-binding (acidic fibroblast) growth factor-1 from its receptor-binding activities by site-directed mutagenesis of a single lysine residue", J. Cell Biol. 111:2129-2138 (1990).
Colman, P., "Effects of amino acid sequence changes on antibody-antigen interactions", Res. Immunol. 1994, 145:33-36.
Datta et al., "Expression of MHC class II-associated invariant chain (Ii;CD74) in thymic epithelial neoplasms", Appl Immunohistochem Mol Morphol. Sep. 2000;8(3):210-215.
Ellis et al., "Engineered anti-CD38 monoclonal antibodies for immunotherapy of multiple myeloma", J Immunol. Jul. 15, 1995;155(2):925-37.
Gondo et al., "HLA class II antigen associated invariant chain gene expression in malignant lymphoma", Br. J. Haematol. Dec. 1987;67(4):413-7.
Hansen et al., "Internalization and catabolism of radiolabelled antibodies to the MHC class-II invariant chain by B-cell lymphomas", Biochem. J. 1996, 320:293-300.
Ibragimova et al., "Stability of the beta-sheet of the WW domain: A molecular dynamics simulation study", Biophys. J. Oct. 1999;77(4):2191-8.
Inukai et al., "Expression of HLA-DR and its enhancing molecules in muscle fibers in polymyositis", Muscle Nerve. Mar. 2000;23(3):385-92.
Ioachim et al., "Lymphoid monoclonal antibodies reactive with lung tumors. Diagnostic applications", Am J Surg Pathol. Jan. 1996;20(1):64-71.
Ishigami et al., "Invariant chain expression in gastric cancer", Cancer Lett. Jul. 10, 2001;168(1):87-91.
Kolata, G., "Clinical promise with new hormones", Science 236:517-519 (1987).
Lazar et al., "Transforming growth factor alpha: an aromatic side chain at position 38 is essential for biological activity", Mol. Cell. Biol. 8(3):1247-1252 (1988).
Lazova et al., "LN-2 (CD74). A marker to distinguish atypical fibroxanthoma from malignant fibrous histiocytoma", Cancer. Jun. 1, 1997;79(11):2115-24.
Leung et al., "Chimerization of LL2, a Rapidly Internalizing Antibody Specific for B Cell Lymphoma", Hybridoma 13(6):469-76 (1994).
Leung et al., "Construction and characterization of a humanized, internalizing, B-cell (CD22)-specific leukemia/lymphoma antibody, LL2", Mol. Immunol. 32(17/18):1413-1427 (1995).
Lin et al., "An antibody treats almost all refractory autoimmune diseases: fact and beyond", J Formos Med Assoc. Apr. 2012;111(4):181-2.
Marks et al., "By-passing immunization. Human antibodies from V-gene libraries displayed on phage", J Mol Biol. Dec. 5, 1991;222(3):581-97.
Moller et al., "CD74", J. Biol. Regul. Homeost. Agents Oct.-Dec. 2000;14(4):299-301.
Ochakovskaya et al., "Therapy of Disseminated B-Cell Lymphoma Xenografts in Severe Combined Immunodeficient Mice with an Anti-CD74 Antibody Conjugated with (111)Indium, (67)Gallium, or (90)Yttrium", Clin. Cancer Res. 7(6):1505-1510 (2001).
Ong et al., "Cell surface expression and metabolism of major histocompatibility complex class II invariant chain (CD74) by diverse cell lines", Immunology. Oct. 1999;98(2):296-302.
Orlandi et al., "Cloning immunoglobulin variable domains for expression by the polymerase chain reaction", Proc. Natl. Acad. Sci. USA 86:3833-3837 (1989).

(56) References Cited

OTHER PUBLICATIONS

Oster et al., "Erythropoietin for the Treatment of Anemia of Malignancy Associated with Neoplastic Bone Marrow Infiltration", J. Clin. Oncol., 8(6):956-962 (1990).

Pawlak-Byczkowska et al. "Two new monoclonal antibodies, EPB-1 and EPB-2, reactive with human lymphoma", Cancer Res. Aug. 15, 1989;49(16):4568-77.

Qu et al., "Internalization and Cytotoxic Effects of a Humanized Anti-CD74 Antibody, LL1", Proc. Am. Assoc. Cancer Res 2002;43:255.

Roche et al., "Cell surface HLA-DR-invariant chain complexes are targeted to endosomes by rapid internalization", Proc Natl Acad Sci USA. Sep. 15, 1993;90(18):8581-5.

Salopek et al., "Anti-CD20 Chimeric Monoclonal Antibody (Rituximab) for the Treatment of Recalcitrant, Life-Threatening Pemphigus Vulgaris: Implications for its Use in Other Autoimmune Antibody Mediated Diseases", J Investig Dermatol. 117(2):542, Abstract #916.

Shan et al., "Apoptosis of malignant human B cells by ligation of CD20 with monoclonal antibodies", Blood. Mar. 1, 1998;91(5):1644-52.

Shih et al., "Localization of an antibody to CD74 (MHC class II invariant chain) to human B cell lymphoma xenografts in nude mice", Cancer Immunol. Immunother. 49:208-216 (2000).

Stephens et al., "Subcutaneous Injections of IMMU-114 (Anti-HLA-DR IgG4 Monoclonal Antibody): Initial Results of a Phase I First-in-Man Study in Hematologic Malignancies", Blood 2015 126:2740.

Tutt et al., "Monoclonal Antibody Therapy of B Cell Lymphoma: Signaling Activity on Tumor Cells Appears More Important Than Recruitment of Effectors", J. Immunol. 161(6):3176-85 (1998).

Wurflein et al., "Evaluating antibodies for their capacity to induce cell-mediated lysis of malignant B cells", Cancer Res. Jul. 15, 1998;58(14):3051-8.

Young et al., "Expression profiling of renal epithelial neoplasms: a method for tumor classification and discovery of diagnostic molecular markers", Am J Pathol. May 2001;158(5):1639-51.

Cardillo et al., "Superior anti-tumor effects of an anti-HLA-DR IgG4 antibody, IMMU-114, in chronic and acute lymphocytic leukemia (CLL and ALL): Comparison to anti-CD20 therapy, chemotherapy, or combined with kinase inhibitors", Abstract 587, Proceedings: AACR 107th Annual Meeting 2016; Apr. 16-20, 2016; New Orleans, LA.

Archive History for NCT01728207: "Phase I Dose Escalation Study of IMMU-114 in Relapsed or Refractory NHL and CLL", Mar. 11, 2015, URL: https://clinicaltrials.gov/ct2/history/NCT01728207?V_4=View#StudyPageTop, [retrieved on Feb. 21, 2019].

Hoyer et al., "Biologies therapy for systemic lupus erythematosus", Z Rheumatol. Apr. 2015;74(3):206-14.

Lin et al., "A phase I/II dose escalation study of apolizumab (Hu1D10) using a stepped-up dosing schedule in patients with chronic lymphocytic leukemia and acute leukemia", Leuk Lymphoma. Dec. 2009;50(12):1958-63.

Rosman et al., "Biologic therapy for autoimmune diseases: an update", BMC Med. Apr. 4, 2013;11:88.

Aagaard et al., "RNAi therapeutics: principles, prospects and challenges", Adv Drug Deliv Rev. Mar. 30, 2007;59(2-3):75-86.

Altomonte et al., "Targeting of HLA-DR molecules transduces agonistic functional signals in cutaneous melanoma", J Cell Physiol. 2004;200:272-276.

Aoudjit et al., "HLA-DR signaling inhibits Fas-mediated apoptosis in A375 melanoma cells", Exp Cell Res. 2004;299:79-90.

ATCC Deposit HB55, deposited to ATCC by LA Lampson on Dec. 14, 1981.

Blancheteau et al., "HLA class II signals sensitize B lymphocytes to apoptosis via Fas/CD95 by increasing FADD recruitment to activated Fas and activation of caspases", Hum Immunol. 2002;63:375-383.

Bridges et al., "Selective in vivo antitumor effects of monoclonal anti-I-A antibody on a B lymphoma", J Immunol. 1987;139:4242-4249.

Brown et al., "Phase II trial of Remitogen (humanized 1D10) monoclonal antibody targeting class II in patients with relapsed low-grade or follicular lymphoma", Clin Lymphoma. Dec. 2001;2(3):188-90.

Brozek et al., "Anti-DR antibodies inhibit in vitro production of human rheumatoid factor", J Clin Lab Immunol. 1990;31:105-109.

Castro and Marciani, 2012 worldwideweb at biosyn.com/tew.aspx?qid=128.

Dermer, G., "Another anniversary for the war on cancer", Bio/Technology, 1994, 12:320.

Elsasser et al., "HLA class II as potential target antigen on malignant B cells for therapy with bispecific antibodies in combination with granulocyte colony-stimulating factor", Blood 1996;87:3803-3812.

Freshney et al., "Culture of animal cells: a manual of basic technique", A.R. Liss, Inc., 1983, New York, p. 4.

Fu et al., "HLA-DR alpha chain residues located on the outer loops are involved in non-polymorphic and polymorphic antibody-binding epitopes", Hum Immunol. 1994; 39:253-260.

Gussow et al., "Humanization of monoclonal antibodies", Method Enzymol. 203:99-121, (1991).

Guy et al., "Deficient expression of MHC class II antigens in some cases of human B cell leukaemia", Clin Exp Immunol. Feb. 1986;63(2):290-7.

Hedge et al., "Phase I study of combination rituximab (CD20) and apolizumab (Hu1D10) monoclonal antibody therapy in previously treated B-cell lymphoma and chronic lymphocytic leukemia", [Abstract] Blood 100 (11 pt 1): A-1389, 2002.

Hertlein et al., "HLA-DR meets ERK", Blood. Jun. 24, 2010;115(25):5126-7.

Ivanov et al., "Monoclonal antibodies directed to CD20 and HLA-DR can elicit homotypic adhesion followed by lysosome-mediated cell death in human lymphoma and leukemia cells", J Clin Invest. Aug. 2009;119(8):2143-59.

Kabelitz et al., "Growth inhibition of Epstein-Barr virus-transformed B cells by anti-HLA-DR antibody L243: possible relationship to L243-induced down-regulation of CD23 antigen expression", Cell Immunol. 1989;120:21-30.

Kitanaka et al., "JNK Signaling in the Control of the Tumor-Initiating Capacity Associated with Cancer Stem Cells", Genes Cancer. Sep. 2013;4(9-10):388-96.

Kostelny et al., "Humanization and characterization of the anti-HLA-DR antibody 1D10", Int J Cancer. Aug. 15, 2001;93(4):556-65.

Kraiba et al., "HLA-DR and DQ antigens in chronic lymphocytic leukemia: dissociation of expression revealed by cell surface, protein, and mRNA studies", Leukemia. May 1989;3(5):386-93.

Lampson et al., "Two populations of Ia-like molecules on a human B cell line", J. Immunol. (1980) 125:293-299.

Liu et al., "Antilymphoma effects of anti-HLA-DR and CD20 monoclonal antibodies (Lym-1 and Rituximab) on human lymphoma cells", Cancer Biother Radiopharm. Oct. 2004;19(5):545-61.

Lund et al., "Expression and characterization of truncated forms of humanized L243 IgG1. Architectural features can influence synthesis of its oligosaccharide chains and affect superoxide production triggered through human Fcgamma receptor I", Eur. J. Biochem. Dec. 2000. vol. 267, No. 24, pp. 7246-7257.

Mone et al., "Hu1D10 induces apoptosis concurrent with activation of the AKT survival pathway in human chronic lymphocytic leukemia cells", Blood. Mar. 1, 2004;103(5):1846-54.

Nagy et al., "Fully human, HLA-DR-specific monoclonal antibodies efficiently induce programmed death of malignant lymphoid cells", Nat Med. 2002;8:801-807.

Nervi et al., "Factors affecting human T cell engraftment, trafficking, and associated xenogeneic graft-vs-host disease in NOD/SCID beta2mnull mice", Exp Hematol. Dec. 2007;35(12):1823-38.

Platanias, LC. "Map kinase signaling pathways and hematologic malignancies", Blood. Jun. 15, 2003;101(12):4667-79.

Qu et al., "Humanization of Immu31, an alpha-fetoprotein-specific antibody", Clin Cancer Res. Oct. 1999;5(10 Suppl):3095s-3100s.

(56) References Cited

OTHER PUBLICATIONS

Rossi et al., "A bispecific antibody-IFNalpha2b immunocytokine targeting CD20 and HLA-DR is highly toxic to human lymphoma and multiple myeloma cells", Cancer Res. Oct. 1, 2010;70(19):7600-9.
Rossi et al., "Preclinical studies on targeted delivery of multiple IFNα2b to HLA-DR in diverse hematologic cancers", Blood. Aug. 18, 2011;118(7):1877-84.
Rudikoff et al., "Single amino acid substitution altering antigen-binding specificity", Proc Natl Acad Sci U S A. Mar. 1982;79(6):1979-83.
Satoh et al., "Epigenetic inactivation of class II transactivator (CIITA) is associated with the absence of interferon-gamma-induced HLA-DR expression in colorectal and gastric cancer cells", Oncogene. Nov. 25, 2004;23(55):8876-86.
Schuurman et al., "The inter-heavy chain disulfide bonds of IgG4 are in equilibrium with intra-chain disulfide bonds", Mol Immunol. Jan. 2001;38(1):1-8.
Schweighofer et al., "Clinical safety and pharmacological profile of the HLA-DR antibody 1D09C3 in patients with B cell chronic lymphocytic leukemia and lymphoma: results from a phase I study", Cancer Immunol Immunother. Dec. 2012;61(12):2367-73.
Stein et al., "HLA-DR as a target for therapy of human and canine B-cell malignancies", Proc. Amer. Assoc. Cancer Res. 2009, 50:301, Abstr#1255.
Stein et al., "Characterization of a humanized IgG4 anti-HLA-DR monoclonal antibody that lacks effector cell functions but retains direct antilymphoma activity and increases the potency of rituximab", Blood 2006;108:2736-44.
Stein et al.,"Therapy of B-cell malignancies by anti-HLA-DR humanized monoclonal antibody, IMMU-114, is mediated through hyperactivation of ERK and JNK MAP kinase signaling pathways", Blood. Jun. 24, 2010;115(25):5180-90.
Stein et al., "Evaluation of anti-human leukocyte antigen-DR monoclonal antibody therapy in spontaneous canine lymphoma", Leuk Lymphoma. Feb. 2011;52(2):273-84.
Stockmeyer et al., "Enhanced killing of B lymphoma cells by granulocyte colony-stimulating factor-primed effector cells and Hu1D10—a humanized human leucocyte antigen DR antibody", Br J Haematol. Sep. 2002;118(4):959-67.
Ting et al., "A new monoclonal antibody recognizing a linear determinant on the HLA-DRalpha chain N-terminus", Hybridoma (Larchmt). Dec. 2009;28(6):423-9.
Vaswani et al., "Humanized antibodies as potential therapeutic drugs", Ann. Allergy Asthma Immunol. 1998;81:105-119.
Vidovic et al., "Selective apoptosis of neoplastic cells by the HLA-DR-specific monoclonal antibody", Cancer Lett. Jun. 19, 1998;128(2):127-35.
Wetzler et al., HLA-DR antigen-negative acute myeloid leukemia, Leukemia. Apr. 2003;17(4):707-15.
Zhao et al., "Combating non-Hodgkin lymphoma by targeting both CD20 and HLA-DR through CD20-243 CrossMab", MAbs. May-Jun. 2014;6(3):740-8.
Zips et al., "New anticancer agents: in vitro and in vivo evaluation", In Vivo. Jan.-Feb. 2005;19(1):1-7.
Zorn et al., "Reduced frequency of FOXP3+ CD4+CD25+ regulatory T cells in patients with chronic graft-versus-host disease", Blood. Oct. 15, 2005;106(8):2903-11.
Banapour et al., "Characterization and epitope mapping of a human monoclonal antibody reactive with the envelope glycoprotein of human immunodeficiency virus", J Immunol. Dec. 15, 1987;139(12):4027-33.
Beers et al., The Merck Manual of Diagnosis and Therapy, Ch. 180, p. 1474-1476; 17th Ed., Whitehouse Station, NJ, Merck Research Labs (1999).
Berkova et al., "Milatuzumab—a promising new immunotherapeutic agent", Expert Opin Investig Drugs. Jan. 2010;19(1):141-9.
Bernhagen et al., "MIF is a noncognate ligand of CXC chemokine receptors in inflammatory and atherogenic cell recruitment", Nat Med. May 2007;13(5):587-96.
Beswick et al., "CD74 in antigen presentation, inflammation, and cancers of the gastrointestinal tract", World J Gastroenterol. Jun. 21, 2009;15(23):2855-61.
Chu et al., "Inconsistency of the immunophenotype of Reed-Sternberg cells in simultaneous and consecutive specimens from the same patients. A paraffin section evaluation in 56 patients", Am J Pathol. Jul. 1992;141(1):11-7.
Coleman et al., "Cooperative regulation of non-small cell lung carcinoma angiogenic potential by macrophage migration inhibitory factor and its homolog, D-dopachrome tautomerase", J Immunol. Aug. 15, 2008;181(4):2330-7.
Filip et al., "Ribosomal protein S19 interacts with macrophage migration inhibitory factor and attenuates its pro-inflammatory function", J Biol Chem. Mar. 20, 2009;284(12):7977-85.
Ghetei et al., "Evaluation of ricin A chain-containing immunotoxins directed against CD19 and CD22 antigens on normal and malignant human B-cells as potential reagents for in vivo therapy", Cancer Res. May 1, 1988;48(9):2610-7.
Gold et al., "Enhanced expression of CD74 in gastrointestinal cancers and benign tissues", Int J Clin Exp Pathol. Nov. 23, 2010;4(1):1-12.
Govindan et al., "Milatuzumab-SN-38 conjugates for the treatment of CD74+ cancers", Mol Cancer Ther. Jun. 2013;12(6):968-78.
Griffiths et al., "Cure of SCID mice bearing human B-lymphoma xenografts by an anti-CD74 antibody-anthracycline drug conjugate", Clin Cancer Res. Dec. 15, 2003;9(17):6567-71.
Hekman et al., "Initial experience with treatment of human B cell lymphoma with anti-CD19 monoclonal antibody", Cancer Immunol Immunother. 1991;32(6):364-72.
Hess et al., "Specificity of effector T lymphocytes in autologous graft-versus-host disease: role of the major histocompatibility complex class II invariant chain peptide", Blood. Mar. 15, 1997;89(6):2203-9.
Kaminski et al., "Radioimmunotherapy of B-cell lymphoma with [131 I]anti-B1 (anti-CD20) antibody", N Engl J Med. Aug. 12, 1993;329(7):459-65.
Koide et al., "Establishment of perineural invasion models and analysis of gene expression revealed an invariant chain (CD74) as a possible molecule involved in perineural invasion in pancreatic cancer", Clin Cancer Res. Apr. 15, 2006;12(8):2419-26.
Lapter et al., "A role for the B-cell CD74/macrophage migration inhibitory factor pathway in the immunomodulation of systemic lupus erythematosus by a therapeutic tolerogenic peptide", Immunology. Jan. 2011;132(1):87-95.
Leng et al., "A small-molecule macrophage migration inhibitory factor antagonist protects against glomerulonephritis in lupus-prone NZB/NZW F1 and MRL/lpr mice", J Immunol. Jan. 1, 2011;186(1):527-38.
Leng et al., "MIF signal transduction initiated by binding to CD74", J Exp Med. Jun. 2, 2003;197(11):1467-76.
Levine et al., "IgM antibody-related polyneuropathies: B-cell depletion chemotherapy using Rituximab", Neurology. May 12, 1999;52(8):1701-4.
Liu et al., "Up-regulation of vascular endothelial growth factor-D expression in clear cell renal cell carcinoma by CD74: a critical role in cancer cell tumorigenesis", J Immunol. Nov. 1, 2008;181(9):6584-94.
Longo, DL., "Immunotherapy for non-Hodgkin's lymphoma", Curr Opin Oncol. Sep. 1996;8(5):353-9.
Lue et al., "Macrophage migration inhibitory factor (MIF) promotes cell survival by activation of the Akt pathway and role for CSN5/JAB1 in the control of autocrine MIF activity", Oncogene. Aug. 2, 2007;26(35):5046-59.
Maharshak et al., "CD74 is a survival receptor on colon epithelial cells", World J Gastroenterol. Jul. 14, 2010;16(26):3258-66.
Maloney et al., "Phase I clinical trial using escalating single-dose infusion of chimeric anti-CD20 monoclonal antibody (IDEC-C2B8) in patients with recurrent B-cell lymphoma", Blood. Oct. 15, 1994;84(8):2457-66.
Mark et al., "Milatuzumab: a promising new agent for the treatment of lymphoid malignancies", Expert Opin Investig Drugs. Jan. 2009;18(1):99-104.

(56) References Cited

OTHER PUBLICATIONS

McClelland et al., "Expression of CD74, the receptor for macrophage migration inhibitory factor, in non-small cell lung cancer", Am J Pathol. Feb. 2009;174(2):638-46.
Meyer-Siegler et al., "Inhibition of macrophage migration inhibitory factor decreases proliferation and cytokine expression in bladder cancer cells", BMC Cancer. Jul. 12, 2004;4:34.
Meyer-Siegler et al., "Inhibition of macrophage migration inhibitory factor or its receptor (CD74) attenuates growth and invasion of DU-145 prostate cancer cells", J Immunol. Dec. 15, 2006;177(12):8730-9.
Morand et al., "Macrophage migration inhibitory factor in rheumatoid arthritis", Front Biosci. Jan. 1, 2005;10:12-22.
O'Connel et al., "The Fas counterattack: Fas-mediated T cell killing by colon cancer cells expressing Fas ligand", J Exp Med. Sep. 1, 1996;184(3):1075-82.
Ong et al., "Single-cell cytotoxicity with radiolabeled antibodies", Clin Cancer Res. Jan. 2001;7(1):192-201.
Perez-Soler et al., Use of Drug Carriers to Ameliorate the Therapeutic Index of Anthracycline Antibiotics, Chapter 19; ACS Symposium Series; American Chemical Society, Washington, DC 1994.
Poulaki et al., "Human retinoblastoma cells are resistant to apoptosis induced by death receptors: role of caspase-8 gene silencing", Invest Ophthalmol Vis Sci. Jan. 2005;46(1):358-66.
Press et al., "Radiolabeled-antibody therapy of B-cell lymphoma with autologous bone marrow support", N. Engl. J. Med. 329(17):1219-24 (1993).
Press et al., "Phase II trial of 131I-B1 (anti-CD20) antibody therapy with autologous stem cell transplantation for relapsed B cell lymphomas", Lancet 346:336-40 (1995).
Protheroe et al., "Remission of inflammatory arthropathy in association with anti-CD20 therapy for non-Hodgkin's lymphoma", Rheumatology (Oxford) 38(11):1150-2 (1999).
Qu et al., "Carbohydrates engineered at antibody constant domains can be used for site-specific conjugation of drugs and chelates", J Immunol Methods. Apr. 15, 1998;213(2):131-44.
Reed, JC., "Dysregulation of apoptosis in cancer", J Clin Oncol. Sep. 1999;17(9):2941-53.
Rowan et al., "Cross-linking of the CAMPATH-1 antigen (CD52) mediates growth inhibition in human B- and T-lymphoma cell lines, and subsequent emergence of CD52-deficient cells", Immunology. Nov. 1998;95(3):427-36.
Shachar et al., "The secret second life of an innocent chaperone: the story of CD74 and B cell/chronic lymphocytic leukemia cell survival", Leuk Lymphoma. Aug. 2011;52(8):1446-54.
Shih et al., "Internalization and intracellular processing of an anti-B-cell lymphoma monoclonal antibody, LL2", Int J Cancer 56(4):538-45 (1994).
Stein et al., "Epitope specificity of the anti-(B cell lymphoma) monoclonal antibody, LL2", Cancer Immunol. Immunother. 37(5):293-8 (1993).
Stein et al., Combining milatuzumab with bortezomib, doxorubicin, or dexamethasone improves responses in multiple myeloma cell lines, Clin Cancer Res. Apr. 15, 2009;15(8):2808-17.
Stein et al., "Antiproliferative activity of a humanized anti-CD74 monoclonal antibody, hLL1, on B-cell malignancies", Blood. Dec. 1, 2004;104(12):3705-11.
Theocharis et al., "Characterization of in vivo mutated T cell clones from patients with systemic lupus erythematosus", Clin Immunol Immunopathol. Feb. 1995;74(2):135-42.
Ungefroren et al., "Human pancreatic adenocarcinomas express Fas and Fas ligand yet are resistant to Fas-mediated apoptosis", Cancer Res. Apr. 15, 1998;58(8):1741-9.
Vera et al., "Intraluminal blockade of cell-surface CD74 and glucose regulated protein 78 prevents substance P-induced bladder inflammatory changes in the rat", PLoS One. Jun. 8, 2009;4(6):e5835.
Abbott: Humira, US, Jan. 31, 2003, p. 1-13, Retrieved from the Internet: URL:http://www.fda.gov/ohrms/dockets/ac/03 /briefing/ 3930B1_02_B-Abbott-Humira Prescribing Info.pdf [retrieved on Mar. 20, 2014].

Anderson et al., "Identification of epitopes on respiratory syncytial virus proteins by competitive binding immunoassay", J Clin Microbiol. Mar. 1986;23(3):475-80.
Carmichael et al., "Peptide-mediated transdermal delivery of botulinum neurotoxin type A reduces neurogenic inflammation in the skin", Pain. May 2010;149(2):316-24. Epub Mar. 23, 2010.
Chen et al., "Transdermal protein delivery by a coadministered peptide identified via phage display", Nat Biotechnol. Apr. 2006;24(4):455-60.
Ellebrecht et al., "Subcutaneous veltuzumab, a humanized anti-CD20 antibody, in the treatment of refractory pemphigus vulgaris", JAMA Dermatol. Dec. 2014;150(12):1331-5.
Goldenberg et al., "Properties and structure-function relationships of veltuzumab (hA20), a humanized anti-CD20 monoclonal antibody", Blood. Jan. 29, 2009;113(5):1062-70.
Golovanov et al., "A simple method for improving protein solubility and long-term stability", J Am Chem Soc. Jul. 28, 2004;126(29):8933-9.
Haddad et al., "Home therapy with subcutaneous immunoglobulins for patients with primary immunodeficiency diseases", Transfus Apher Sci. Jun. 2012;46(3):315-21.
Jefferis et al., "Human immunoglobulin allotypes: possible implications for immunogenicity", MAbs. Jul.-Aug. 2009;1(4):1-7.
Jurynczyk et al., "Immune regulation of multiple sclerosis by transdermally applied myelin peptides", Ann Neurol. Nov. 2010;68(5):593-601.
Kavanaugh et al., "Golimumab, a new human tumor necrosis factor alpha antibody, administered every four weeks as a subcutaneous injection in psoriatic arthritis: Twenty-four-week efficacy and safety results of a randomized, placebo-controlled study", Arthritis Rheum. Apr. 2009;60(4):976-86.
Kheddo et al., "The effect of arginine glutamate on the stability of monoclonal antibodies in solution", Int J Pharm. Oct. 1, 2014;473(1-2):126-33.
Kim et al., "Biochemical enhancement of transdermal delivery with magainin peptide: modification of electrostatic interactions by changing pH", Int J Pharm. Oct. 1, 2008;362(1-2):20-8.
Liebman et al., "Low-dose anti-CD20 veltuzumab given intravenously or subcutaneously is active in relapsed immune thrombocytopenia: a phase I study", Br J Haematol. Sep. 2013;162(5):693-701.
Lundin et al., "Phase II trial of subcutaneous anti-CD52 monoclonal antibody alemtuzumab (Campath-1H) as first-line treatment for patients with B-cell chronic lymphocytic leukemia (B-CLL)", Blood. Aug. 1, 2002;100(3):768-73.
McLaughlin et al., "Rituximab chimeric anti-CD20 monoclonal antibody therapy for relapsed indolent lymphoma: half of patients respond to a four-dose treatment program", J Clin Oncol. Aug. 1998;16(8):2825-33.
Magdelaine-Beuzelin et al., "IgG1 heavy chain-coding gene polymorphism (G1m allotypes) and development of antibodies-to-infliximab", Pharmacogenet Genomics. May 2009;19(5):383-7.
Morchhauser et al., "Humanized anti-CD20 antibody, veltuzumab, in refractory/recurrent non-Hodgkin's lymphoma: phase I/II results", J Clin Oncol. Jul. 10, 2009;27(20):3346-53.
Namboodiri et al., "Differential inhibition of trastuzumab- and cetuximab-induced cytotoxicity of cancer cells by immunoglobulin G1 expressing different GM allotypes", Clin Exp Immunol. Dec. 2011;166(3):361-5.
Negrea et al., "Subcutaneous injections of low-dose veltuzumab (humanized anti-CD20 antibody) are safe and active in patients with indolent non-Hodgkin's lymphoma", Haematologica. Apr. 2011;96(4):567-73.
Robak et al., "New anti-CD20 monoclonal antibodies for the treatment of B-cell lymphoid malignancies", BioDrugs. Feb. 1, 2011;25(1):13-25.
Shi et al., "Monoclonal antibody classification based on epitope-binding using differential antigen disruption", J Immunol Methods. Jul. 31, 2006;314(1-2):9-20.
Stickler et al., "The human G1m1 allotype associates with CD4+ T-cell responsiveness to a highly conserved IgG1 constant region peptide and confers an asparaginyl endopeptidase cleavage site", Genes Immun. Apr. 2011;12(3):213-21.

(56) References Cited

OTHER PUBLICATIONS

Tay et al., "Targeting HLA-DR", Leuk Lymphoma. Dec. 2009;50(12):1911-3.
Uchida et al., "Development of an efficient transdermal delivery system of small interfering RNA using functional peptides, Tat and AT-1002", Chem Pharm Bull (Tokyo). Feb. 2011;59(2):196-201.
Wang et al., "Arginine-rich intracellular delivery peptides noncovalently transport protein into living cells", Biochem Biophys Res Commun. Aug. 4, 2006;346(3):758-67.
Warne et al., "Development of high concentration protein biopharmaceuticals: the use of platform approaches in formulation development", Eur J Pharm Biopharm. Jun. 2011;78(2):208-12.

\* cited by examiner

L243Vk

```
GACATCCAGATGACTCAGTCTCCAGCCTCCCTATCTGTGTGGGAGAAACTGTCACCATCACATGTCGAGCAAGTGAGAATATTTAC    90
  1                          10                         20                         30
  D   I   Q   M   T   Q   S   P   A   S   L   S   V   S   V   G   E   T   V   T   I   T   C   R   A   S   E   N   I   Y
                                                                                              ─────────────────────────────
                                                                                                          CDR1

AGTAATTTAGCATGGTATCGTCAGAAACAGGGGAAAATCTCCCTCAGCTCCCTGGTCTTTGCTGCATCAAACTTAGCAGATGGTGTGCCATCA    180
                     40                         50                         60
  S   N   L   A   W   Y   R   Q   K   Q   G   K   S   P   Q   L   L   V   F   A   A   S   N   L   A   D   G   V   P   S
  ─────────────                                                      ─────────────────────────
                                                                                CDR2

AGGTTCAGTGGCAGTGGATCAGGCACACAGTATTCCCTCAAGATCAACAGCCTGCAGTCTGAAGATTTTGGGGATTATTACTGTCAACAT    270
                     70                         80                         90
  R   F   S   G   S   G   S   G   T   Q   Y   S   L   K   I   N   S   L   Q   S   E   D   F   G   D   Y   Y   C   Q   H

TTTTGGACTACTCCGTGGGGCGTTCGGTGGAGGCACCAACCTGGAAATCAAACGT    321
                     100                        108
  F   W   T   T   P   W   A   F   G   G   G   T   N   L   E   I   K   R
  ─────────────────
         CDR3
```

Figure 2:
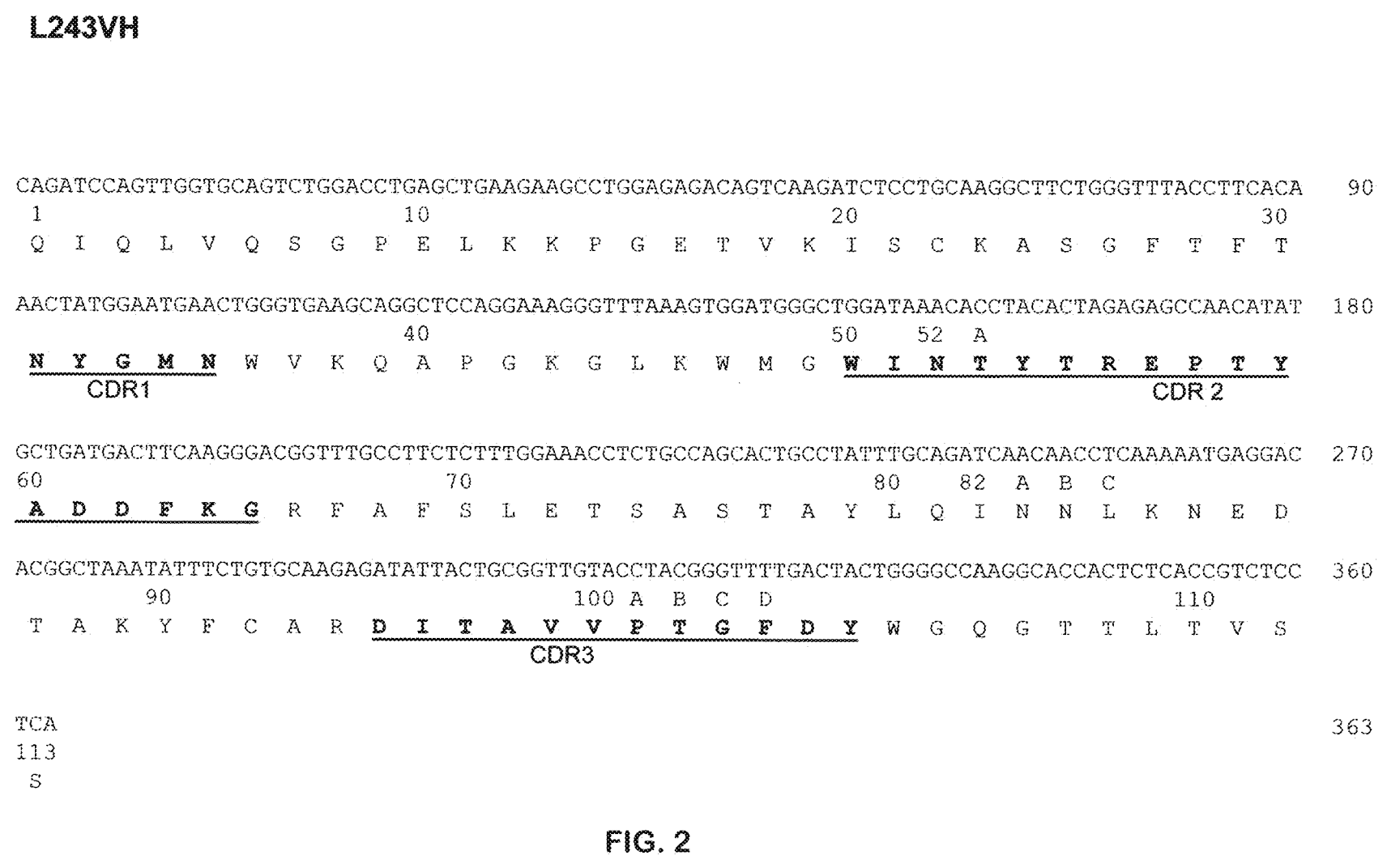

```
CAGATCCAGTTGGTGCAGTCTGGACCTGAGCTGAAGAAGCCTGGAGAGACAGTCAAGATCTCCTGCAAGGCTTCTGGGTTTACCTTCACA      90
  1                   10                  20                  30
  Q  I  Q  L  V  Q  S  G  P  E  L  K  K  P  G  E  T  V  K  I  S  C  K  A  S  G  F  T  F  T

AACTATGGAATGAACTGGGTGAAGCAGGCTCCAGGAAAGGGTTTAAAGTGGATGGGCTGGATAAACACCTACACTAGAGAGCCAACATAT    180
                   40                  50  52 A              WINTYREPTY
  N  Y  G  M  N  W  V  K  Q  A  P  G  K  G  L  K  W  M  G  W  I  N  T  Y  R  E  P  T  Y
  ───CDR1───                                                 ─────────CDR2

GCTGATGACTTCAAGGGACGGTTTGCCTTCTCTCTTGGAAACCTCTGCCAGCACTGCCTATTTGCAGATCAACAACCTCAAAAATGAGGAC    270
 60                     70                  80  82 A B C
  A  D  D  F  K  G  R  F  A  F  S  L  E  T  S  A  S  T  A  Y  L  Q  I  N  N  L  K  N  E  D

ACGGCTAAATATTTCTGTGCAAGAGATATTACTGCGGTTGTACCTACGGGGTTTGACTACTGGGGCCAAGGCACCACTCTCACCGTCTCC    360
                   90                100 A B C D                       110
  T  A  K  Y  F  C  A  R  D  I  T  A  V  V  P  T  G  F  D  Y  W  G  Q  G  T  T  L  T  V  S
                        ────────────CDR3────────────

TCA                                                                                         363
113
  S
```

FIG. 2 hL243Vk

```
GACATCCAGCTGACCCAGTCTCCATCATCTCTGAGCGCATCTGTTGGAGATAGGGTCACTATCACTTGTCGAGCAAGTGAGAATATTTAC    90
  1                    10                    20                    30
  D   I   Q   L   T   Q   S   P   S   S   L   S   A   S   V   G   D   R   V   T   I   T   C   R   A   S   E   N   I   Y
                                                                                                    CDR1

AGTAATTTAGCATGGTATCGTCAGAAACCAGGGAAAGCACCTAAACTTCTGGTCTTTGCTGCATCAAACTTAGCAGATGGTGTGCCTTCG   180
                    40                    50                    60
  S   N   L   A   W   Y   R   Q   K   P   G   K   A   P   K   L   L   V   F   A   A   S   N   L   A   D   G   V   P   S
              CDR1                                                      CDR2

CGATTCTCTGGCAGCGGGATCTGGGACAGATTATACTTTCACCATCAGCTCTCTTCAACCAGAAGACATTGCAACATATTATTGTCAACAT   270
                    70                    80                    90
  R   F   S   G   S   G   S   G   T   D   Y   T   F   T   I   S   S   L   Q   P   E   D   I   A   T   Y   Y   C   Q   H

TTTTGGACTCCGTGGGCGTTCGGCGGAGGGACCAAGCTGCAGATCAAACGT   324
                   100            108
  F   W   T   P   W   A   F   G   G   G   T   K   L   Q   I   K   R
        CDR3
```

FIG. 3 hL243VH

```
CAGGTGCAACTGCAGCAATCTGGGTCTGAGTTGAAGAAGCCTGGGGCCTCAGTGAAGGTTTCCTGCAAGGCTTCTGGATTTACCTTCACA    90
1                   10                  20                  30
Q   V   Q   L   Q   Q   S   G   S   E   L   K   K   P   G   A   S   V   K   V   S   C   K   A   S   G   F   T   F   T

AACTATGGAATGAACTGGGTGAAGCAGGCCCCTGGACAAGGGCTTAAGTGGATGGGCTGGATAAACACCTACACTAGAGAGCCAACATAT  180
        40                  50      52  A           
N   Y   G   M   N   W   V   K   Q   A   P   G   Q   G   L   K   W   M   G   W   I   N   T   Y   T   R   E   P   T   Y
    CDR1                                                            CDR2

GCTGATGACTTCAAGGGACGGTTTGCCTTCTCCCTTGGACACCTCTGTCAGCAGCATATCCAGATCAGCAGCCTAAAGGCTGACGAC  270
60                          70              80  82 A B C
A   D   D   F   K   G   R   F   A   F   S   L   D   T   S   V   S   T   A   Y   L   Q   I   S   S   L   K   A   D   D
    CDR2(cont.)

ACTGCCGTGTATTTCTGTGCAAGAGATATTACTGCGGTTGTACCTACGGGGTTTGACTACTGGGGCCAAGGGTCCCTGGTCACCGTCTCC  360
            90                  100 A B C D             110
T   A   V   Y   F   C   A   R   D   I   T   A   V   V   P   T   G   F   D   Y   W   G   Q   G   S   L   V   T   V   S
                            CDR3

TCA                                                                                          363
113
S
```

FIG. 4

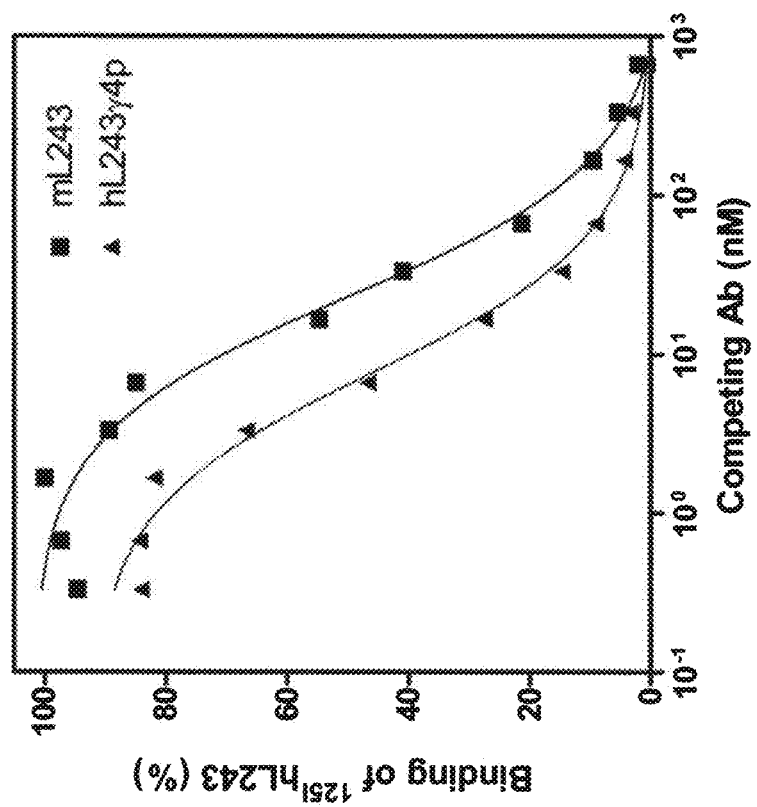
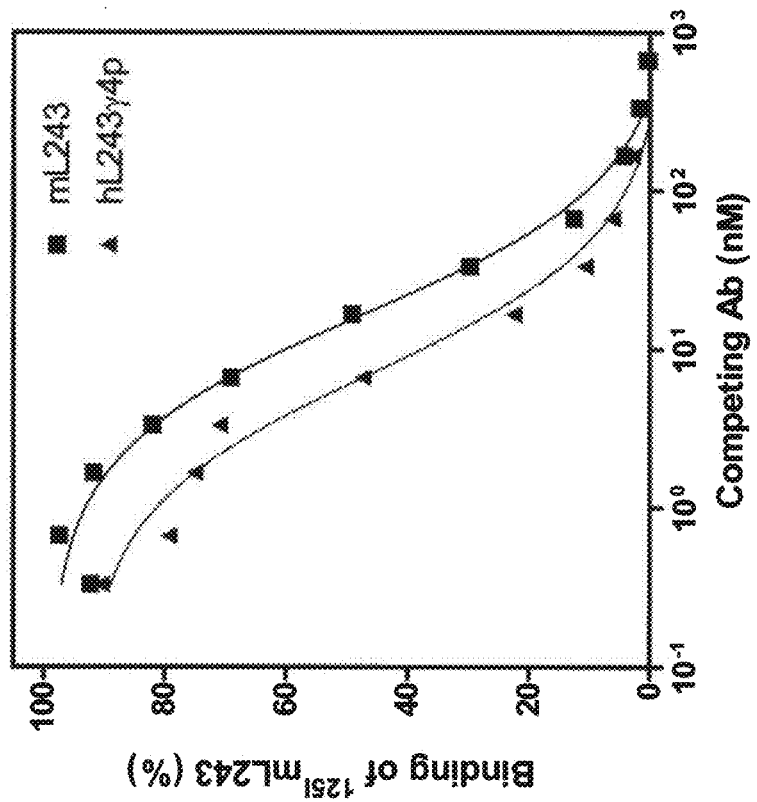
FIG. 6

FIG. 23A
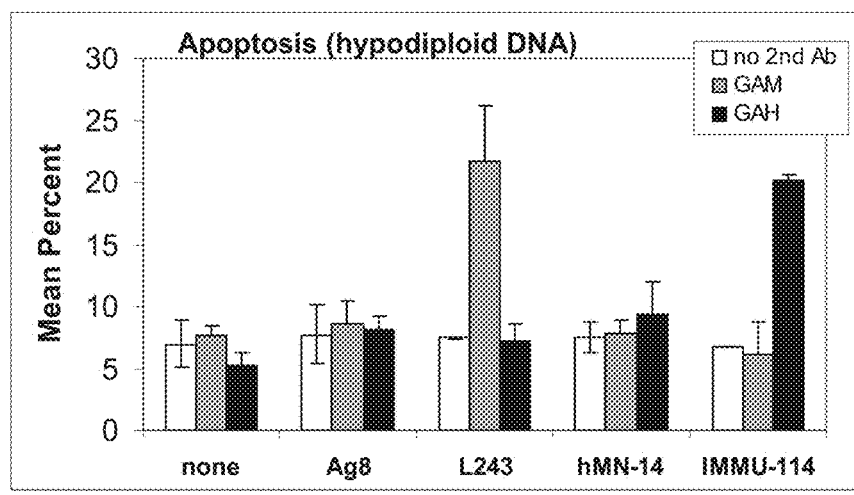
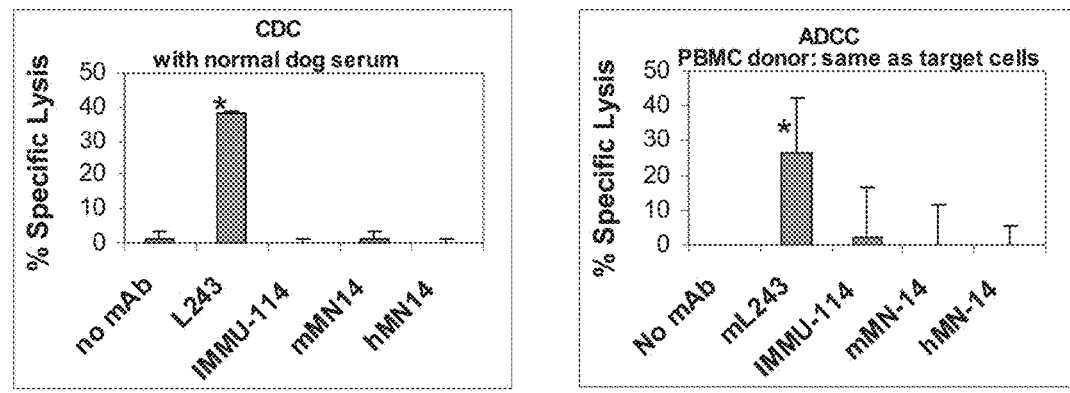
FIG. 23B
FIG. 23C

SUBCUTANEOUS ANTI-HLA-DR MONOCLONAL ANTIBODY FOR TREATMENT OF HEMATOLOGIC MALIGNANCIES

RELATED APPLICATIONS

This application is a continuation of U.S. patent application Ser. No. 15/240,052 (now abandoned), filed Aug. 18, 2016, which was continuation-in-part of U.S. patent application Ser. No. 14/876,200 (now issued U.S. Pat. No. 9,683,050), filed Oct. 6, 2015, which was a continuation of U.S. patent application Ser. No. 14/163,443 (now issued U.S. Pat. No. 9,180,205), filed Jan. 24, 2014, which was a divisional of U.S. patent application Ser. No. 14/132,549 (now issued U.S. Pat. No. 9,468,689), filed Dec. 18, 2013, which was a divisional of U.S. patent application Ser. No. 13/461,307 (now U.S. Pat. No. 8,658,773), filed May 1, 2012, which claimed the benefit under 35 U.S.C. 119(e) of U.S. Provisional Appl. Nos. 61/509,850, filed Jul. 20, 2011, and 61/481,489, filed May 2, 2011. U.S. patent application Ser. No. 15/240,052 claimed the benefit under 35 U.S.C. 119(e) of U.S. Provisional Appl. Ser. Nos. 62/208,128, filed Aug. 21, 2015, and 62/262,692, filed Dec. 2, 2015. This application is a continuation-in-part of Ser. No. 14/630,097 (now abandoned), filed Feb. 24, 2015, which was a divisional of U.S. patent application Ser. No. 14/080,231 (now issued U.S. Pat. No. 8,992,917), filed Nov. 14, 2013, which was a divisional of U.S. patent application Ser. No. 12/556,718 (now issued U.S. Pat. No. 8,613,903), filed Sep. 10, 2009, which was a divisional of U.S. patent application Ser. No. 11/368,296 (now U.S. Pat. No. 7,612,180), filed Mar. 3, 2006, which claimed the benefit under 35 U.S.C. § 119(e) of U.S. Provisional Appl. Ser. No. 60/657,695, filed Mar. 3, 2005. This application is a continuation-in-part of U.S. patent application Ser. No. 15/353,141 (now issued U.S. Pat. No. 10,174,114), filed Nov. 16, 2016, which was divisional of U.S. patent application Ser. No. 14/878,715 (now abandoned), filed Oct. 8, 2015, which was a divisional of U.S. patent application Ser. No. 14/224,866 (now issued U.S. Pat. No. 9,187,561), filed Mar. 25, 2014, which was a divisional of U.S. Pat. application Ser. No. 12/754,140 (now issued U.S. Pat. No. 8,722,047), filed Apr. 5, 2010, which was a continuation-in-part of U.S. patent application Ser. No. 12/556,718 (now issued U.S. Pat. No. 8,613,903), filed Sep. 10, 2009, which was a divisional of U.S. patent application Ser. No. 11/368,296 (now issued U.S. Pat. No. 7,612,180), filed Mar. 3, 2006, which claimed the benefit under 35 USC 119(e) of U.S. Provisional Appl. Ser. No. 60/657,695 filed on Mar. 3, 2005. U.S. patent application Ser. No. 12/754,140 (now issued U.S. Pat. No. 8,722,047), claimed the benefit under 35 U.S.C. 119(e) of U.S. Provisional Patent Appl. Ser. Nos. 61/166,809, filed Apr. 6, 2009, and 61/168,715, filed Apr. 13, 2009. The text of each priority application is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Aug. 11, 2016, is named IMM364US1_SL.txt and is 32,092 bytes in size.

FIELD OF THE INVENTION

The present invention concerns improved methods of treating hematologic cancers by subcutaneous administration of an anti-HLA-DR antibody or antigen-binding fragment thereof. In preferred embodiments, the anti-HLA-DR antibody or fragment thereof is a humanized L243 (hL243) antibody, as disclosed in the Examples below. More preferably, the hL243 antibody is an IgG4 antibody, with decreased ADCC and CDC. Most preferably, the hL243 antibody comprises a Ser241Pro point mutation in the hinge region of the antibody or fragment thereof. In particular embodiments, the anti-HLA-DR antibody is prepared in a concentrated formulation that allows for subcutaneous administration of small volumes of solution. In an exemplary embodiment, a dosage of 200 mg of antibody is administered once, twice, or three times a week for the first three weeks of a 4-week cycle. Patients may receive two or more consecutive treatment cycles, followed by maintenance therapy (e.g., one week of treatment every four weeks times 4). Preferably, administration induces no more than a Grade 3 or Grade 4 toxicity. More preferably, administration results in a decrease in tumor size for solid tumors, or a decrease in white blood cell count for non-solid tumors. Decreases in tumor size preferably are in the range of a 40% to 90% reduction in tumor volume. The antibody or fragment may be administered alone, as a conjugate of a therapeutic agent, or in combination with one or more different therapeutic agents, as discussed in detail below. In particularly preferred embodiments, the therapeutic agent is a Bruton kinase inhibitor (such as ibrutinib) or a PI3K inhibitor (such as idelalisib). The combination of antibody and therapeutic agent preferably exhibits synergistic effects in treating hematologic cancers.

BACKGROUND

Rituximab anti-CD20 IgG therapy is credited with revitalizing antibody therapies with its ability to effectively treat follicular lymphoma without the extensive side effects associated with more traditional chemotherapy regimens. Since rituximab's approval by the FDA in 1997, the mortality rate from NHL has declined by 2.8% per year (Molina, 2008, Ann Rev Med 59:237-50), and the use of this agent has been expanded to a variety of diseases. While rituximab has been a remarkable success in follicular non-Hodgkin lymphoma (NHL), for which it was first approved, only half of the patients had an objective response, with at most 10% having a complete response (McLaughlin et al., 1998, J Clin Oncol 16:2825-33). Rituximab was less effective in the more aggressive types of NHL, such as diffuse large B cell lymphoma (DLBCL), but when it was combined with combination chemotherapy, improved and durable objective responses compared to the separate therapies were found, making R-CHOP a standard protocol for the treatment of DLBCL (e.g., Leonard et al., 2008, Semin Hematol 45:S11-16; Friedberg et al., 2002, Br J Haematol 117:828-34). The success of rituximab stimulated the evaluation of a number of other antibodies and antibody conjugates, and while a number of these have shown promising activity, to-date only one other unconjugated antibody therapy, alemtuzumab (anti-CD52) for chronic lymphocytic leukemia (CLL), has been approved for use in hematologic malignancies (Robak, 2008, Curr Cancer Drug Targets 8:156-71).

The human leukocyte antigen-DR (HLA-DR) is one of three isotypes of the major histocompatibilty complex (MHC) class II antigens. HLA-DR is highly expressed on a variety of hematologic malignancies and has been actively pursued for antibody-based lymphoma therapy (Brown et al., 2001, Clin Lymphoma 2:188-90; DeNardo et al., 2005, Clin Cancer Res 11:7075s-9s; Stein et al., 2006, Blood 108:2736-44). The human HLA-DR antigen is expressed in non-Hodgkin lymphoma (NHL), chronic lymphocytic leukemia (CLL), and other B-cell malignancies at significantly higher levels than typical B-cell markers, including CD20. Preliminary studies indicate that anti-HLA-DR mAbs are markedly more potent than other naked mAbs of current clinical interest in in vitro and in vivo experiments in lymphomas, leukemias, and multiple myeloma (Stein et al., unpublished results).

HLA-DR is also expressed on a subset of normal immune cells, including B cells, monocytes/macrophages, Langerhans cells, dendritic cells, and activated T cells (Dechant et al., 2003, Semin Oncol 30:465-75). Thus, it is perhaps not surprising that prior attempts to develop anti-HLA-DR antibodies have been hampered by toxicity, notably infusion-related toxicities that are likely related to complement activation (Lin et al, 2009, Leuk Lymphoma 50:1958-63; Shi et al., 2002, Leuk Lymphoma 43:1303-12).

The L243 antibody (hereafter mL243) is a murine IgG2a anti-HLA-DR antibody. This antibody may be of potential use in the treatment of diseases such as autoimmune disease or cancer, particularly leukemias or lymphomas, by targeting the D region of HLA. mL243 demonstrates potent suppression of in vitro immune function and is monomorphic for all HLA-DR proteins. However, problems exist with the administration of mouse antibodies to human patients, such as the induction of a human anti-mouse antibody (HAMA) response. A need exists for more effective compositions and methods of use of anti-HLA-DR antibodies, with improved efficacy and decreased toxicity.

SUMMARY

In certain embodiments, the present invention relates to methods of treating hematologic cancer, autoimmune disease or immune dysfunction disease (e.g., GVHD, organ transplant rejection) by subcutaneous administration of an ant-HLA-DR antibody. Preferably the antibody is chimeric, humanized or human. More preferably, the anti-HLA-DR antibody competes for binding to, or binds to the same epitope of HLA-DR as, a murine monoclonal antibody mL243 comprising the murine L243 heavy chain CDR sequences CDR1 (NYGMN (SEQ ID NO: 39)), CDR2 (WINTYTREPTYADDFKG (SEQ ID NO: 40)) and CDR3 (DITAVVPTGFDY (SEQ ID NO: 41)) and the light chain CDR sequences CDR1 (RASENIYSNLA (SEQ ID NO: 42)), CDR2 (AASNLAD (SEQ ID NO: 43)), and CDR3 (QHFWTTPWA (SEQ ID NO: 44)). The murine L243 antibody of use for competitive binding studies is publicly available from the American Type Culture Collection, Rockville, Md., (see Accession number ATCC HB55). Most preferably, the anti-HLA-DR antibody comprises the L243 heavy chain CDR sequences CDR1 (NYGMN (SEQ ID NO: 39)), CDR2 (WINTYTREPTYADDFKG (SEQ ID NO: 40)) and CDR3 (DITAVVPTGFDY (SEQ ID NO: 41)) and the light chain CDR sequences CDR1 (RASENIYSNLA (SEQ ID NO: 42)), CDR2 (AASNLAD (SEQ ID NO: 43)), and CDR3 (QHFWTTPWA (SEQ ID NO: 44)).

In other preferred embodiments, in addition to the L243 CDR references and human framework (FR) and constant region sequences, a humanized anti-HLA-DR antibody may further comprise one or more of framework residues 27, 38, 46, 68 and 91 substituted from the mL243 heavy chain and/or one or more of framework residues 37, 39, 48 and 49 substituted from the mL243 light chain. In a more preferred embodiment, the hL243 antibody comprises the sequences of SEQ ID NO:36 and SEQ ID NO:38.

In alternative embodiments, the anti-HLA-DR antibody may be a naked antibody or an immunoconjugate that is attached to at least one therapeutic agent. Conjugates with multiple therapeutic agents of the same or different type are also encompassed. Alternatively, the anti-HLA-DR antibody may be administered in combination with at least one therapeutic agent administered before, simultaneously with or after the anti-HLA-DR antibody. Any therapeutic agent known in the art, as discussed in more detail below, may be utilized in combination with or attached to the anti-HLA-DR antibody, including but not limited to radionuclides, immunomodulators, anti-angiogenic agents, cytokines, chemokines, growth factors, hormones, drugs, prodrugs, enzymes, oligonucleotides, siRNAs, pro-apoptotic agents, photoactive therapeutic agents, cytotoxic agents, chemotherapeutic agents, toxins, Bruton kinase inhibitors, PI3K inhibitors, and other antibodies or antigen binding fragments thereof.

In certain methods of use, the subject antibody may bind to at least one epitope of HLA-DR on HLA-DR$^+$ cells, resulting in cell death. In one particular embodiment, cell death may result without use of either cytotoxic addends or immunological effector mechanisms, for example by induction of apoptosis. The anti-HLA-DR antibodies may be of use for therapy of any disease state in which HLA-DR$^+$ cells are involved, including but not limited to various forms of cancer or autoimmune disease.

In certain embodiments, the subject antibodies may be used in a pharmaceutical composition for therapeutic and/or diagnostic use. A pharmaceutical composition may contain further therapeutic agents as described below, in addition to other standard components such as buffers, detergents, salts, excipients, preservatives and other such agents known in the art. In particularly preferred embodiments, the composition may be a high-concentration formulation, as disclosed for example in U.S. Pat. Nos. 8,658,773 and 9,180,205, incorporated herein by reference.

The pharmaceutical composition or fusion protein or multispecific antibody may further comprise one or more additional antibodies or fragments thereof which bind to an antigen selected from the group consisting of carbonic anhydrase IX, alpha-fetoprotein (AFP), α-actinin-4, A3, antigen specific for A33 antibody, ART-4, B7, Ba 733, BAGE, BrE3-antigen, CA125, CAMEL, CAP-1, CASP-8/m, CCL19, CCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD80, CD83, CD95, CD126, CD132, CD133, CD138, CD147, CD154, CDC27, CDK-4/m, CDKN2A, CTLA-4, CXCR4, CXCR7, CXCL12, HIF-1α, colon-specific antigen-p (CSAp), CEA (CEACAM5), CEACAM6, c-Met, DAM, EGFR, EGFRvIII, EGP-1 (TROP-2), EGP-2, ELF2-M, Ep-CAM, fibroblast growth factor (FGF), Flt-1, Flt-3, folate receptor, G250 antigen, GAGE, gp100, GRO-β, HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-γ, IFN-α, IFN-β, IFN-.lamda., IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), KC4-antigen, KS-1-antigen, KS 1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, pancreatic cancer mucin, PD-1, PD-1 receptor, PD-L1, placental growth factor, p53, PLAGL2, prostatic acid phosphatase, PSA, PRAME, PSMA, P1GF, ILGF, ILGF-1R, IL-6, IL-25, RS5, RANTES, T101, SAGE, 5100, survivin, survivin-2B, TAC, TAG-72, tenascin, TRAIL receptors, TNF-α, Tn antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, and an oncogene product (see, e.g., Sensi et al., Clin Cancer Res 2006, 12:5023-32; Parmiani et al., J Immunol 2007, 178:1975-79; Novellino et al. Cancer Immunol Immunother 2005, 54:187-207). The additional antibody or fragment thereof may administered before, with, or after any pharmaceutical composition containing a humanized anti-HLA-DR antibody.

Exemplary additional antibodies that may be utilized in combination with an anti-HLA-DR include, but are not limited to, hR1 (anti-IGF-1R, U.S. patent application Ser. No. 13/688,812, filed Nov. 29, 2012) hPAM4 (anti-mucin, U.S. Pat. No. 7,282,567), hA20 (anti-CD20, U.S. Pat. No. 7,151,164), hA19 (anti-CD19, U.S. Pat. No. 7,109,304), hIMMU31 (anti-AFP, U.S. Pat. No. 7,300,655), hLL1 (anti-CD74, U.S. Pat. No. 7,312,318), hLL2 (anti-CD22, U.S. Pat. No. 5,789,554), hMu-9 (anti-CSAp, U.S. Pat. No. 7,387,772), hL243 (anti-HLA-DR, U.S. Pat. No. 7,612,180), hMN-14 (anti-CEA, U.S. Pat. No. 6,676,924), hMN-15 (anti-CEA, U.S. Pat. No. 7,541,440), hRS7 (anti-EGP-1, U.S. Pat. No. 7,238,785) and hMN-3 (anti-CEA, U.S. Pat. No. 8,287,865) the Examples section of each cited patent or application incorporated herein by reference. The skilled artisan will realize that this list is not limiting and that any known antibody may be used, as discussed in more detail below.

Various embodiments may concern use of the subject anti-HLA-DR antibodies or fragments thereof to treat or diagnose a disease, including but not limited to B cell non-Hodgkin's lymphomas, B cell acute and chronic lymphoid leukemias, Burkitt lymphoma, Hodgkin's lymphoma, hairy cell leukemia, acute and chronic myeloid leukemias, T cell lymphomas and leukemias, multiple myeloma, Waldenstrom's macroglobulinemia, carcinomas, melanomas, sarcomas, gliomas, and skin cancers. The carcinomas may be selected from the group consisting of carcinomas of the oral cavity, gastrointestinal tract, pulmonary tract, breast, ovary, prostate, uterus, urinary bladder, pancreas, liver, gall bladder, skin, and testes. In addition, the subject anti-HLA-DR antibodies or fragments may be used to treat an autoimmune disease, for example acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis *nodosa*, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes *dorsalis*, giant cell arteritis/polymyalgia, pernicious anemia, rapidly progressive glomerulonephritis, psoriasis, or fibrosing alveolitis. In certain embodiments, the subject antibodies may be used to treat leukemia, such as chronic lymphocytic leukemia, acute lymphocytic leukemia, chronic myeloid leukemia or acute myeloid leukemia.

Preferably, the antibody or fragment thereof may be designed or selected to comprise human constant region sequences that belong to specific allotypes, which may result in reduced immunogenicity when the immunoconjugate is administered to a human subject. Preferred allotypes for administration include a non-G1m1 allotype (nG1m1), such as G1m3, G1m3,1, G1m3,2 or G1m3,1,2. More preferably, the allotype is selected from the group consisting of the nG1m1, G1m3, nG1m1,2 and Km3 allotypes.

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

FIG. 1 (also SEQ ID NO:31 and SEQ ID NO:32) illustrates an exemplary DNA encoding an amino acid sequence $V_K$ of the mouse L243 anti-HLA-DR antibody. The putative CDR regions are underlined. Nucleotide residues are numbered sequentially. Kabat's Ig molecule numbering is used for amino acid residues. The numbering for the residues with a letter (on top) is the number of preceding residues plus the letter, eg, the number for T following N52 is 52A; the numbers for N, N and L following 82 are 82A, 82B and 82C, respectively.

FIG. 2 (also SEQ ID NO:33 and SEQ ID NO:34) illustrates an exemplary DNA encoding an amino acid sequence $V_H$ of the mouse L243 anti-HLA-DR antibody. The putative CDR regions are underlined. Nucleotide residues are numbered sequentially. Kabat's Ig molecule numbering is used for amino acid residues as described above.

FIG. 3 (also SEQ ID NO:35 and SEQ ID NO:36) illustrates exemplary DNA and amino acid sequences of a humanized L243 $V_K$. The bold and underlined sections of the amino acid sequences indicate the CDRs as defined by the Kabat numbering scheme.

FIG. 4 (also SEQ ID NO:37 and SEQ ID NO:38) illustrates exemplary DNA and amino acid sequences of a humanized L243 $V_H$. The bold and underlined sections of the amino acid sequences indicate the CDRs as defined by the Kabat numbering scheme.

FIG. 6 illustrates exemplary Ag-binding affinities comparing hL243 γ 4P and mL243 in a competitive cell surface binding assay. A constant amount (100,000 cpm, ~10 µCi/µg) of $^{125}$I-labeled mL234 (on left) or hL243γ4P (on right) was mixed with varying concentrations (0.2-700 nM) of unlabeled hL243γ4P (solid triangle) or mL2343 (solid box).

The mixtures were added to Raji cells and incubated at room temperature for 2 h. The cells were washed to remove unbound antibodies and the radioactivity associated with the cells was counted. hL243γ4P and mL234 were shown to compete with each other for binding to cell surface Ag. In both cases hL243γ4P appeared to bind to Raji cells more strongly than mL243.

Figure 7:
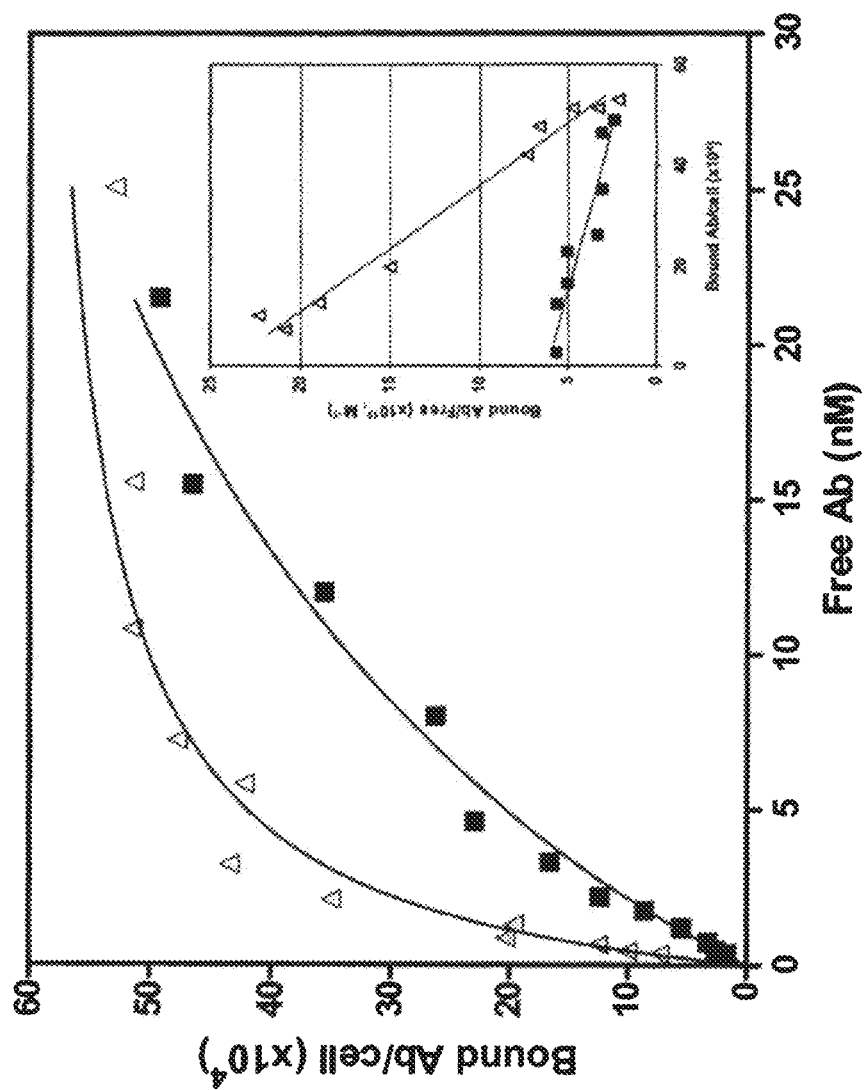

FIG. 7 illustrates exemplary Ag-binding affinities of hL243γ4P and mL243 determinated by direct cell surface saturation binding and Scachard plot analysis. Varying concentrations of $^{125}$I-labeled mL234 (solid square) or hL243γ4P (open triangle) were incubated with 2×10$^5$ Daudi human lymphoma cells at 4° C. for 2 h, and unbound radioactivity was removed from cell suspensions by washing. The cell-associated radioactivity was counted, specific binding of radiolabeled antibody to the cell surface antigen calculated, and Scatchard plot analysis was then applied to determine the maximum number of binding sites per cell and the apparent antigen-binding affinity constant. The maximum binding of mL234 or hL243γ4P to Daudi cell surface was 6×10$^6$ molecules/cell. The dissociation constants determined for mL234 or hL243γ4P were 14 and 2.6 nM, respectively.

Figure 8:
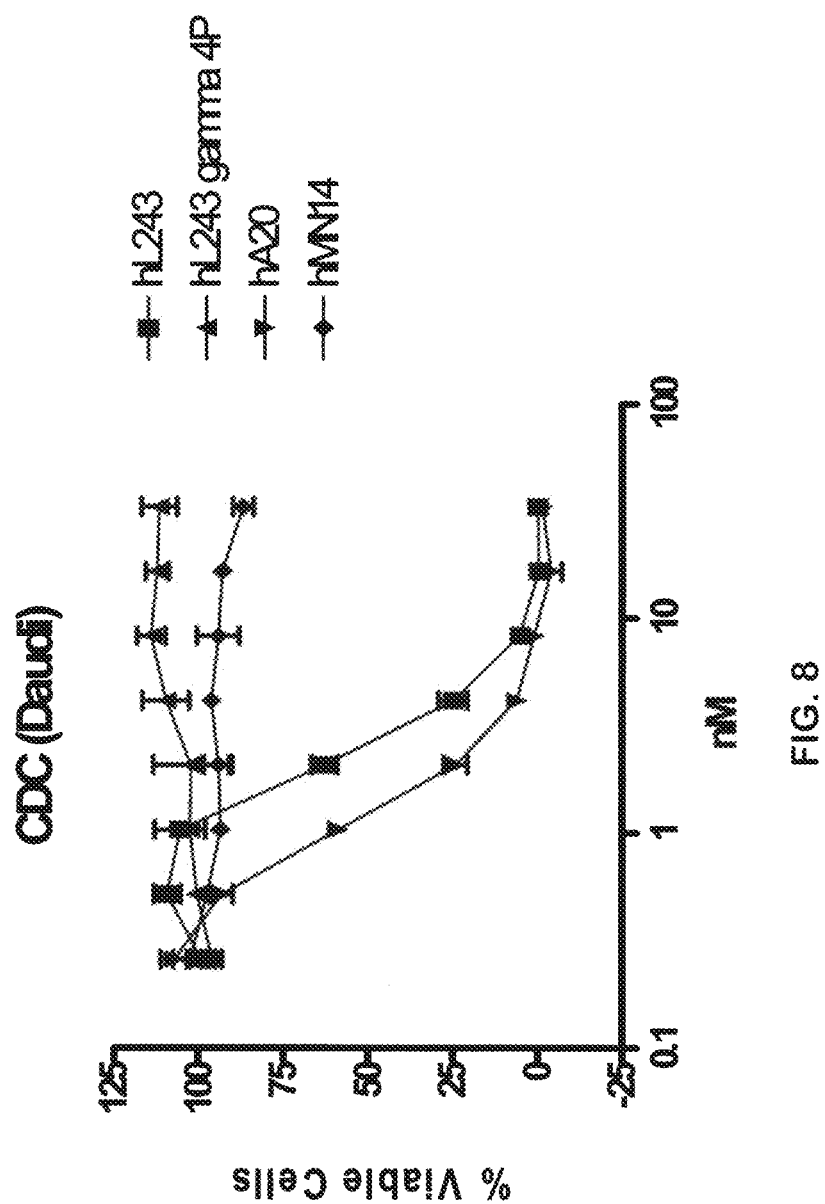

FIG. 8 illustrates that hL243 is effective in killing target cells in the presence of human serum complement. Daudi cells were incubated with hL243, hL243γ4P, hA20 (a positive control), and hMN-14 (a negative control) in the presence of human serum complement. hL243γ4P was shown not to produce any complement-induced cytotoxicity.

Figure 9A:
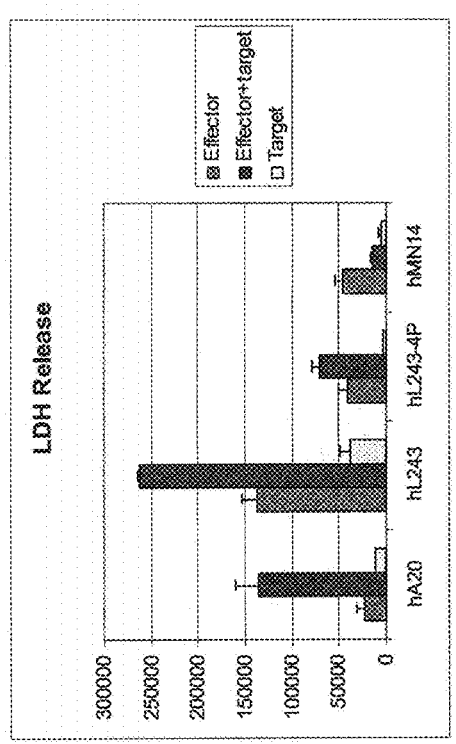

FIG. 9A illustrates LDH release by ADCC as observed for hL243, hL243γ4P, hA20 (positive control) and hMN-14 (negative control).

Figure 9B:
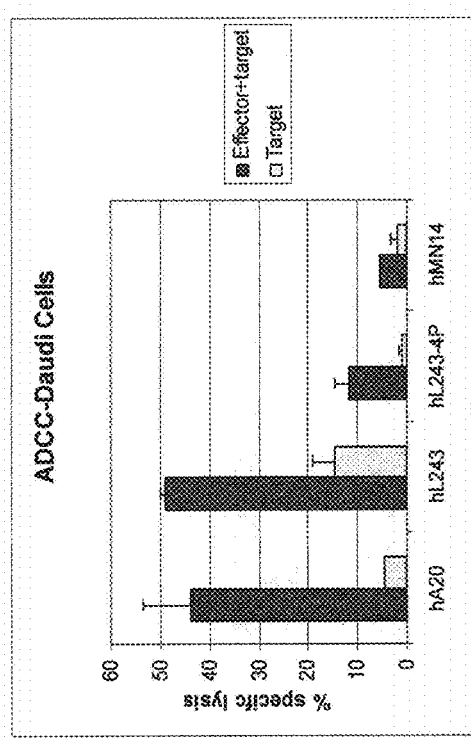

FIG. 9B illustrates % cell lysis by ADCC as observed for hL243, hL243γ4P, hA20 (positive control) and hMN-14 (negative control).

Figure 10:
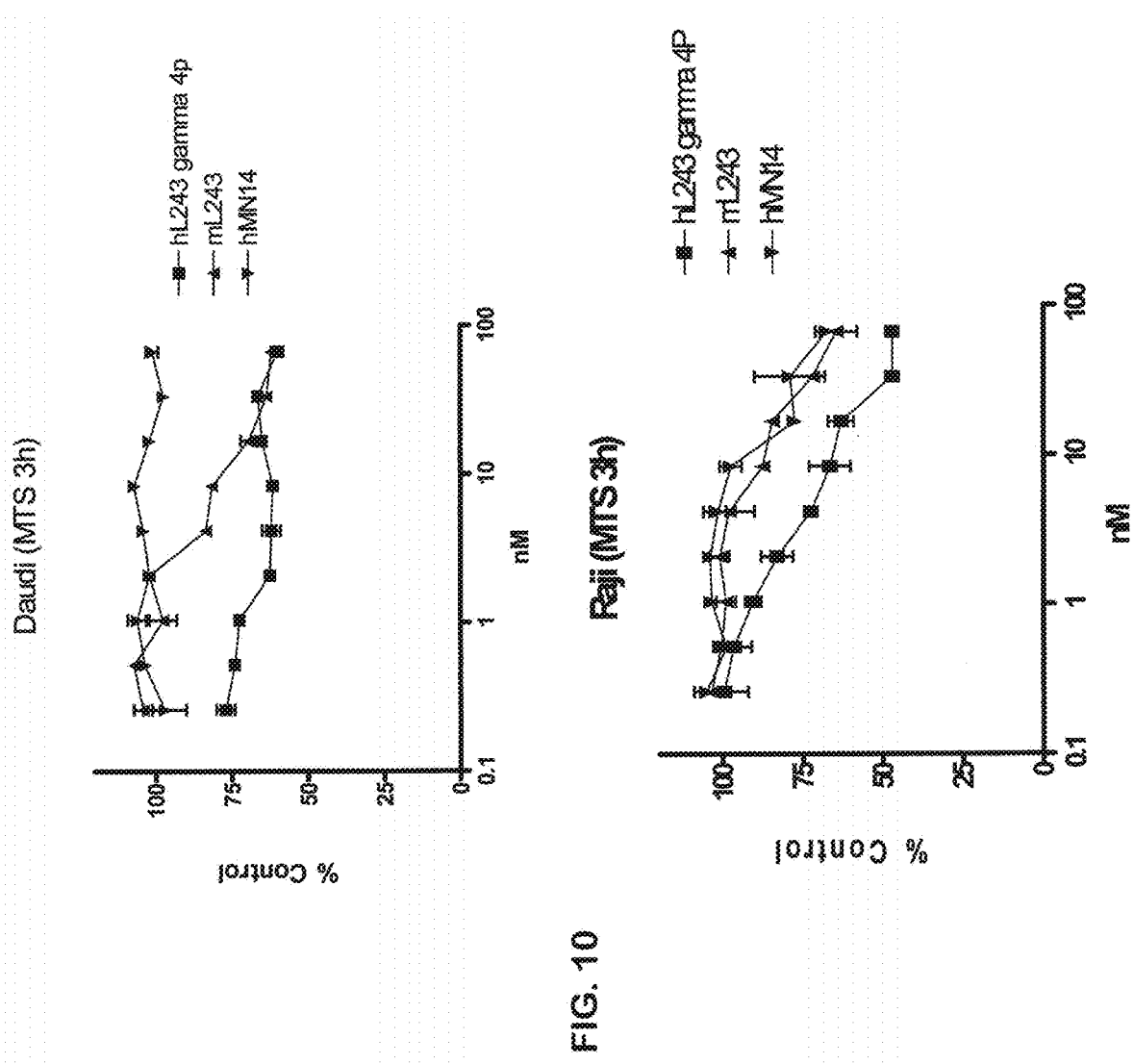

FIG. 10 illustrates exemplary in vitro proliferative assays on Daudi (top) and Raji (bottom) cell lines at the end of 2 days.

Figure 11A:
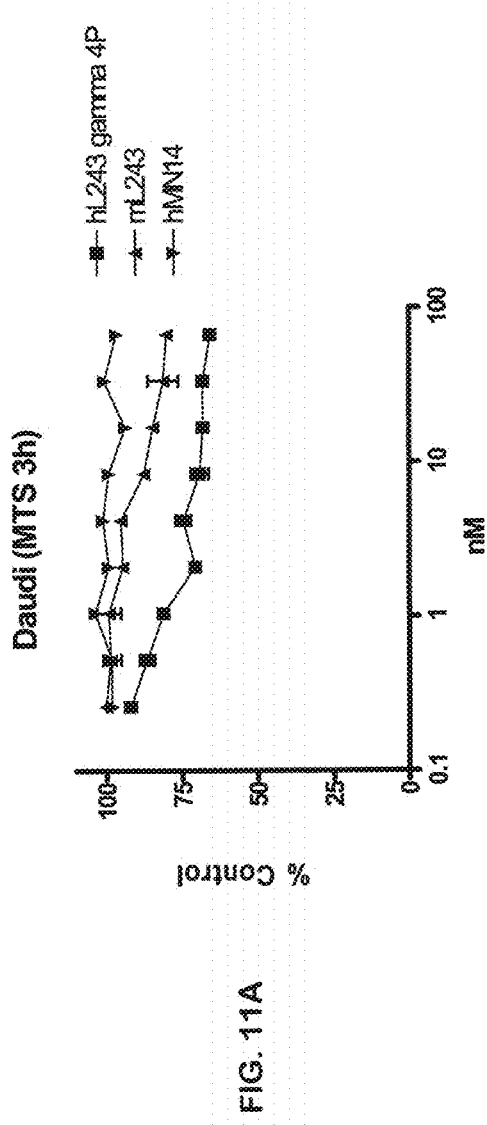

FIG. 11A illustrates exemplary in vitro proliferative assays on Daudi cell lines at the end of 3 days.

Figure 11B:
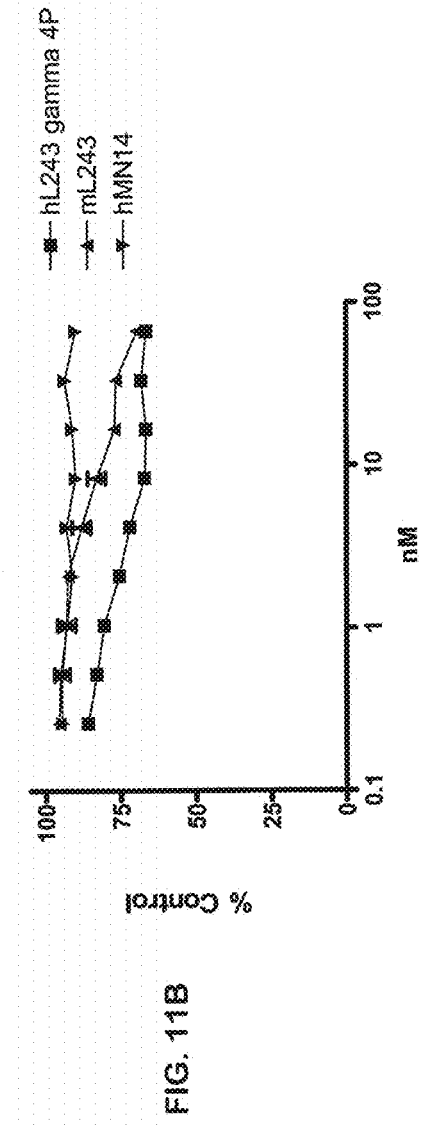

FIG. 11B illustrates exemplary in vitro proliferative assays on Raji cell lines at the end of 3 days.

Figure 12:
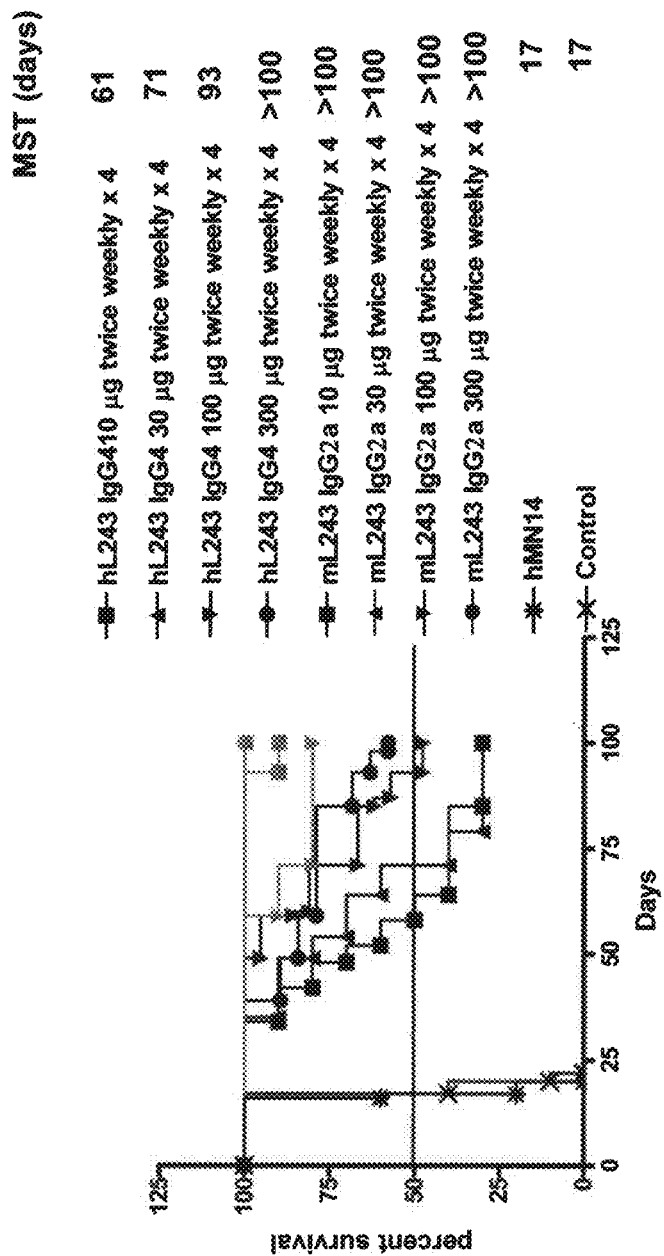

FIG. 12 illustrates exemplary median survival times for tumor-bearing SCID mice injected with hL243γ4P.

Figure 13:
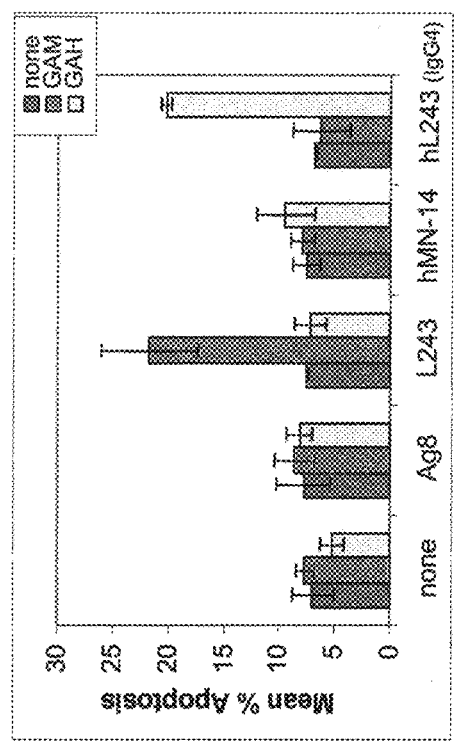

FIG. 13 illustrates comparative induction of apoptosis in dog lymphoma cells (measured as % cells with a sub G0/G1 phase DNA content) caused by L243, hL243 (IgG4 isotype), hMN-14 (humanized MN-14 IgG), and Ag8 (murine myeloma derived mAb). L243 and hL243 caused apoptosis when crosslinked with goat anti-mouse (GAM) and goat-anti human (GAH) antibodies respectively.

Figure 14A:
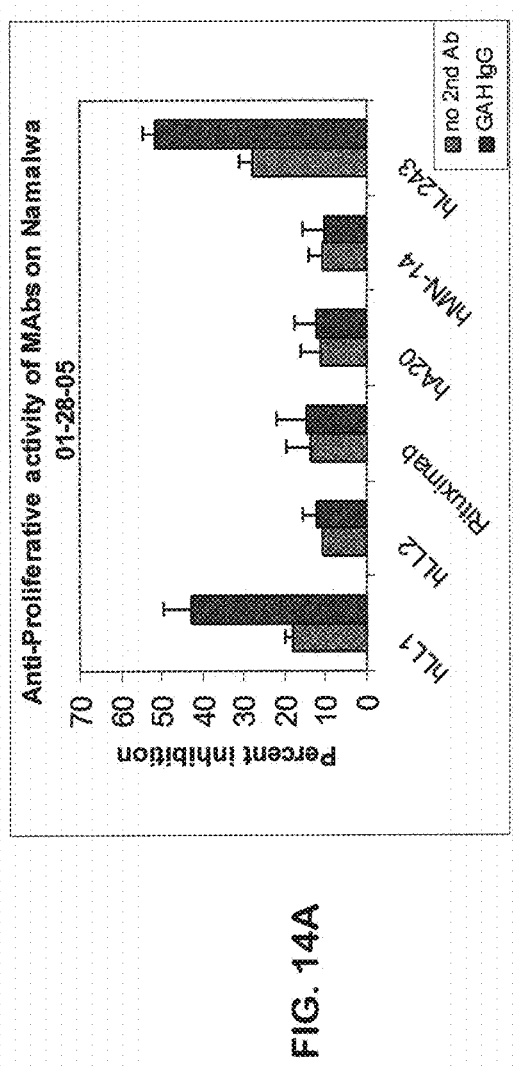

FIG. 14A illustrates anti-proliferative effects of humanized antibodies (hLL1, hLL2, Rituximab, hA2, hMN-14 and hL243 IgG4 isotype), with and without goat anti-human IgG (GAH)) on Namalwa human B cell lymphoma cell line as determined by a $^3$H-thymidine uptake assay with single antibodies.

Figure 14B:
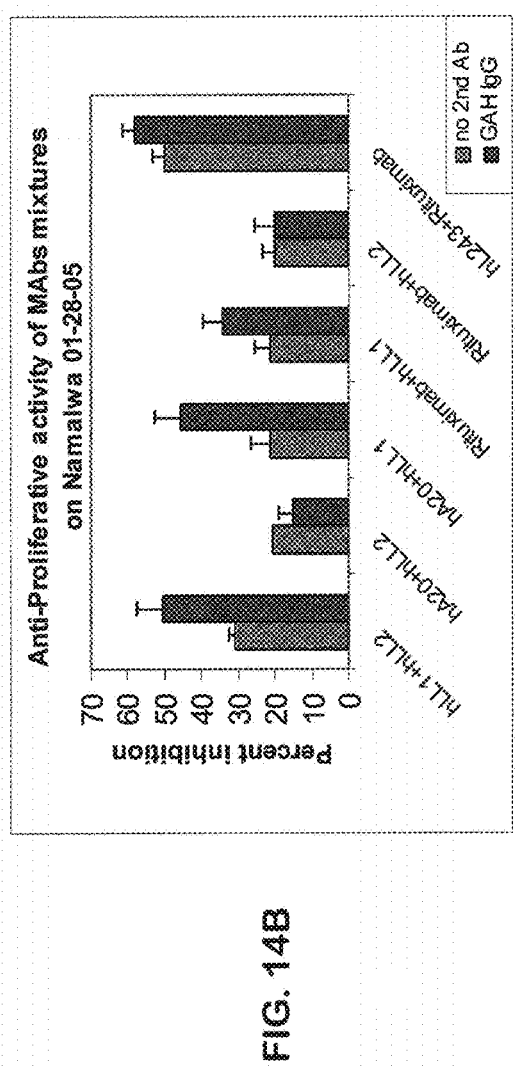

FIG. 14B illustrates anti-proliferative effects of humanized antibodies (hLL1, hLL2, Rituximab, hA2, hMN-14 and hL243 IgG4 isotype), with and without goat anti-human IgG (GAH)) on Namalwa human B cell lymphoma cell line as determined by a $^3$H-thymidine uptake assay with mixtures of antibodies.

Figure 15A:
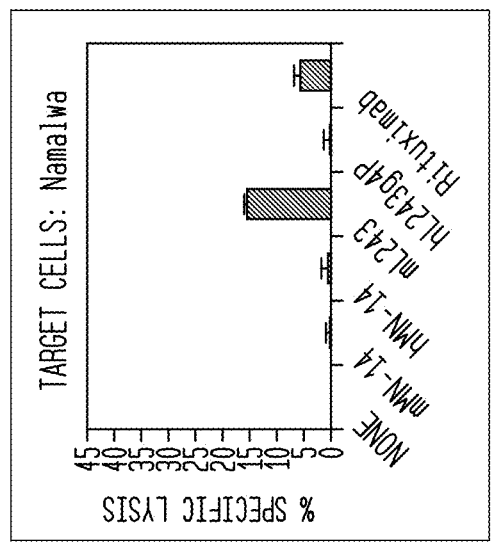

FIG. 15A illustrates CDC assays in Raji cells when exposed to various antibodies disclosed herein.

Figure 15B:
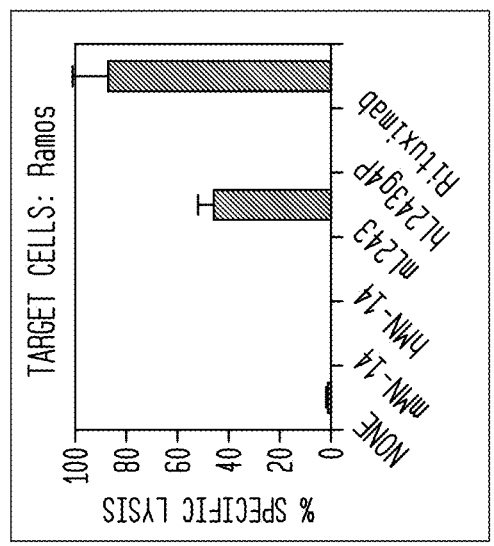

FIG. 15B illustrates CDC assays in Ramos cells when exposed to various antibodies disclosed herein.

Figure 15C:
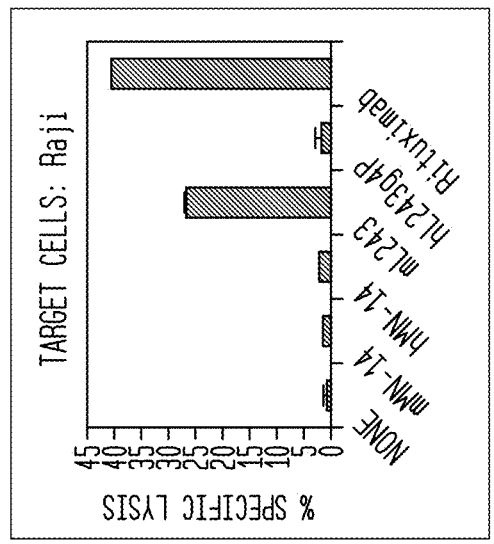

FIG. 15C illustrates CDC assays in Namalwa cells when exposed to various antibodies disclosed herein.

Figure 16:
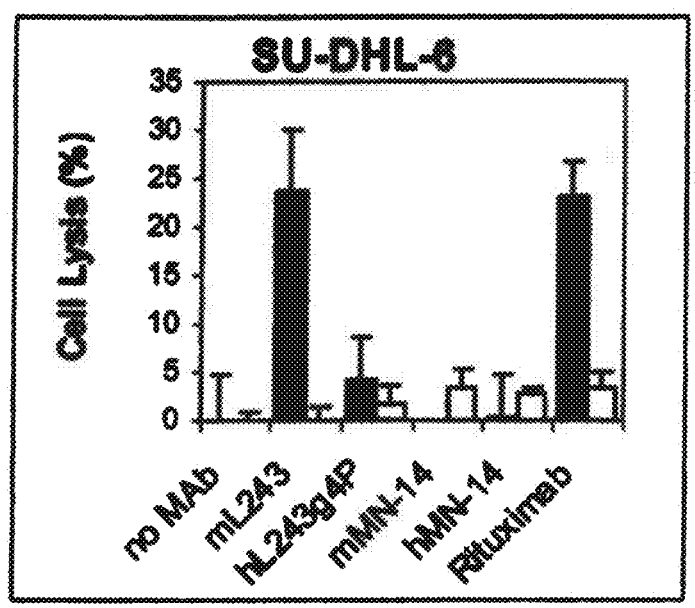

FIG. 16 illustrates ADCC assays and calcein AM release when SU-DHL-6 cells are exposed to various antibodies disclosed herein.

Figure 17A:
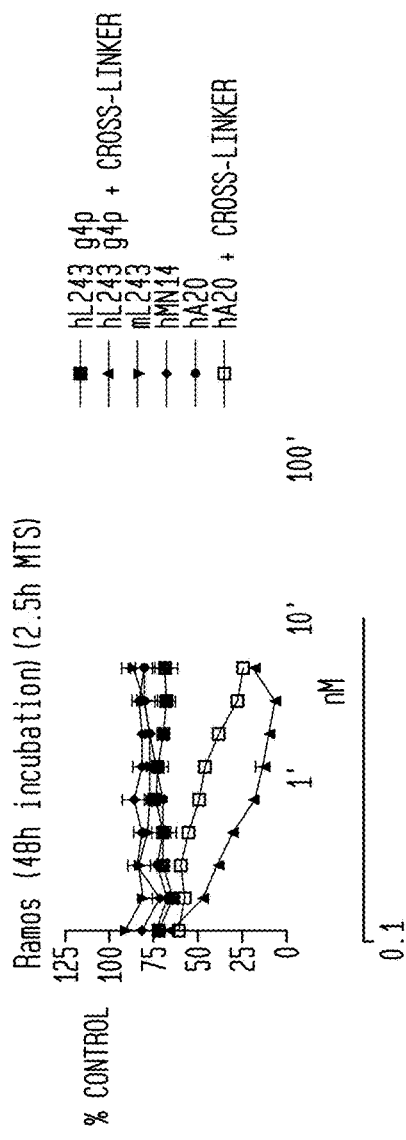

FIG. 17A illustrates anti-proliferative effects of hL243γ4P on several cell lines disclosed in MTT studies.

Figure 17B:
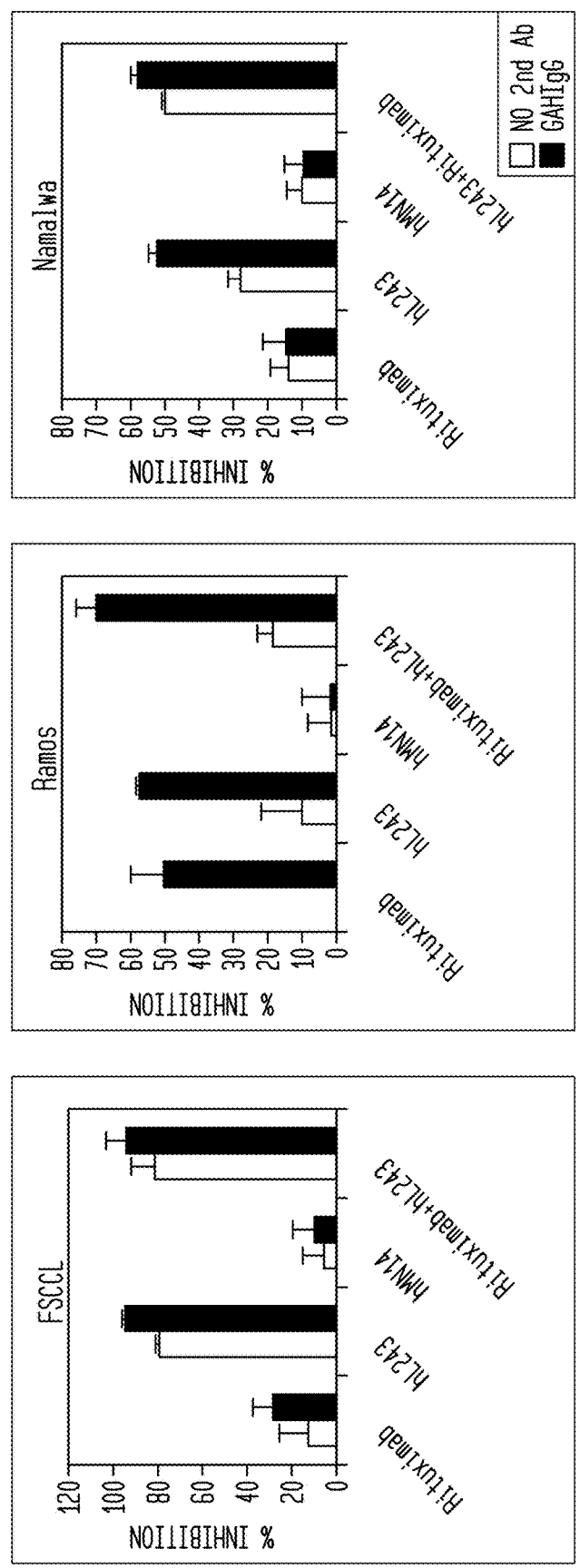

FIG. 17B illustrates anti-proliferative effects of hL243γ4P on several cell lines disclosed in $^3$H-thymidine uptake assays. hL243 refers to the γ4P form of the antibody.

Figure 18A:
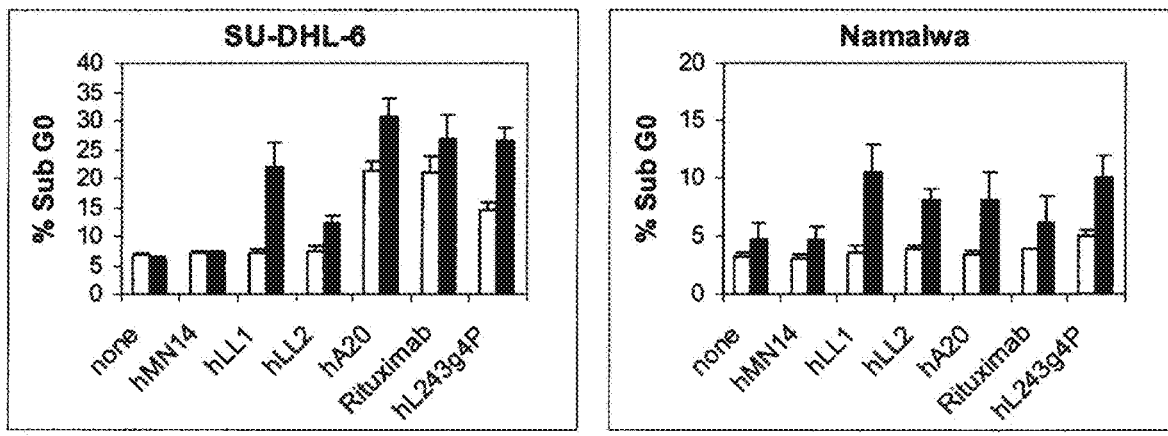

FIG. 18A illustrates induction of apoptosis. Dead cells are represented by clear and apoptotic cells are represented by solid bars. The Figure shows measurement of Sub G DNA in SU-DHL-6 and Namalwa cells. Cells used had 97% viability prior to treatment.

Figure 18B:
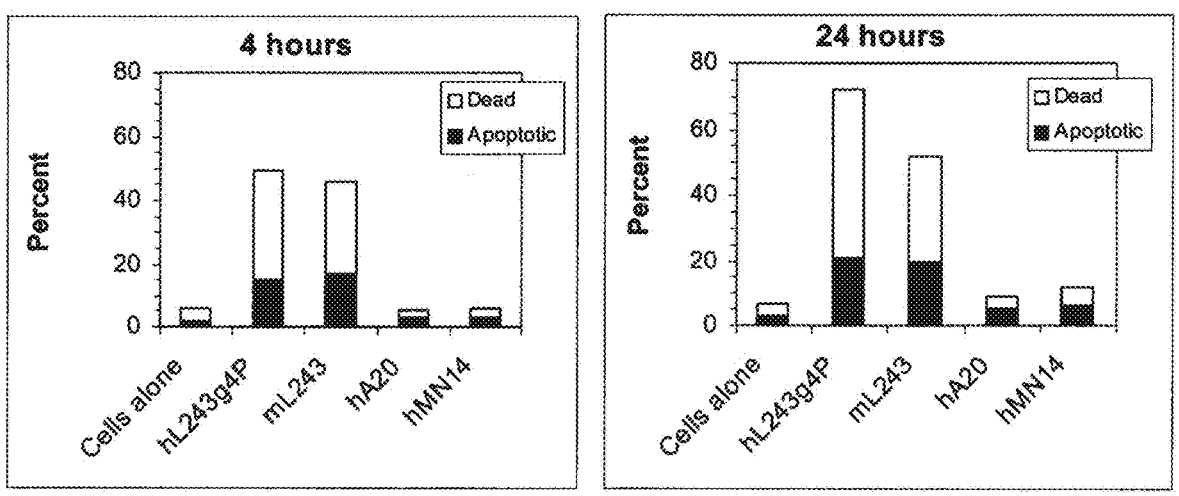

FIG. 18B illustrates induction of apoptosis. Dead cells are represented by clear and apoptotic cells are represented by solid bars. The Figure shows Annexin V/7-ADD at 4 and 24 hours. Cells used had 97% viability prior to treatment.

Figure 19:
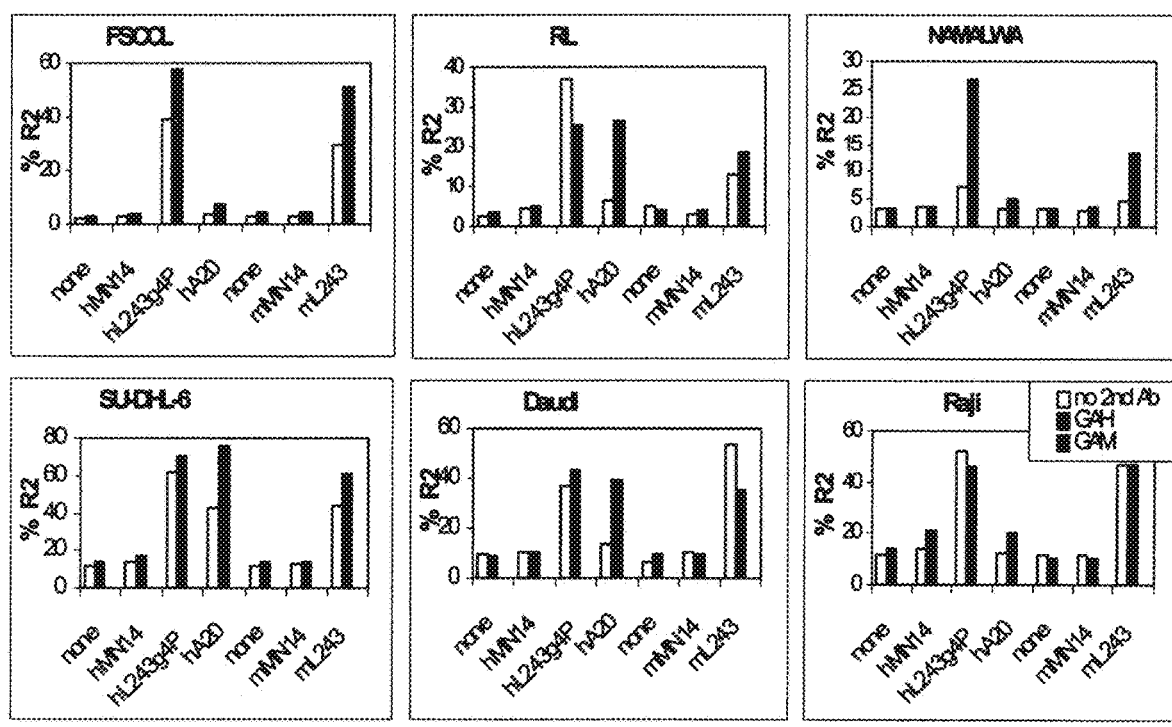

FIG. 19 illustrates mitochondrial membrane potential using a JC-1 assay in several cell lines.

Figure 20A:
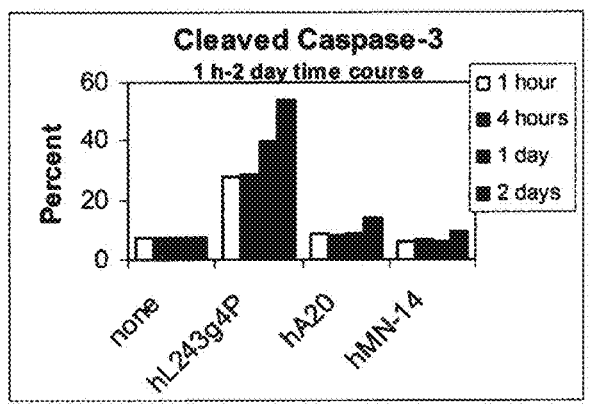

FIG. 20A illustrates cleaved caspase-3 time course studies in Daudi cells.

Figure 20B:
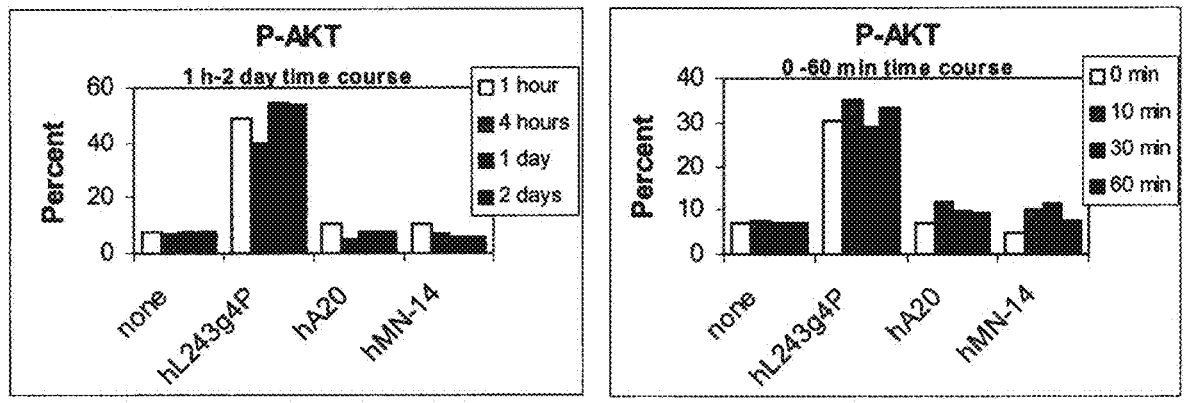

FIG. 20B illustrates P-AKT time course studies in Daudi cells.

Figure 21:
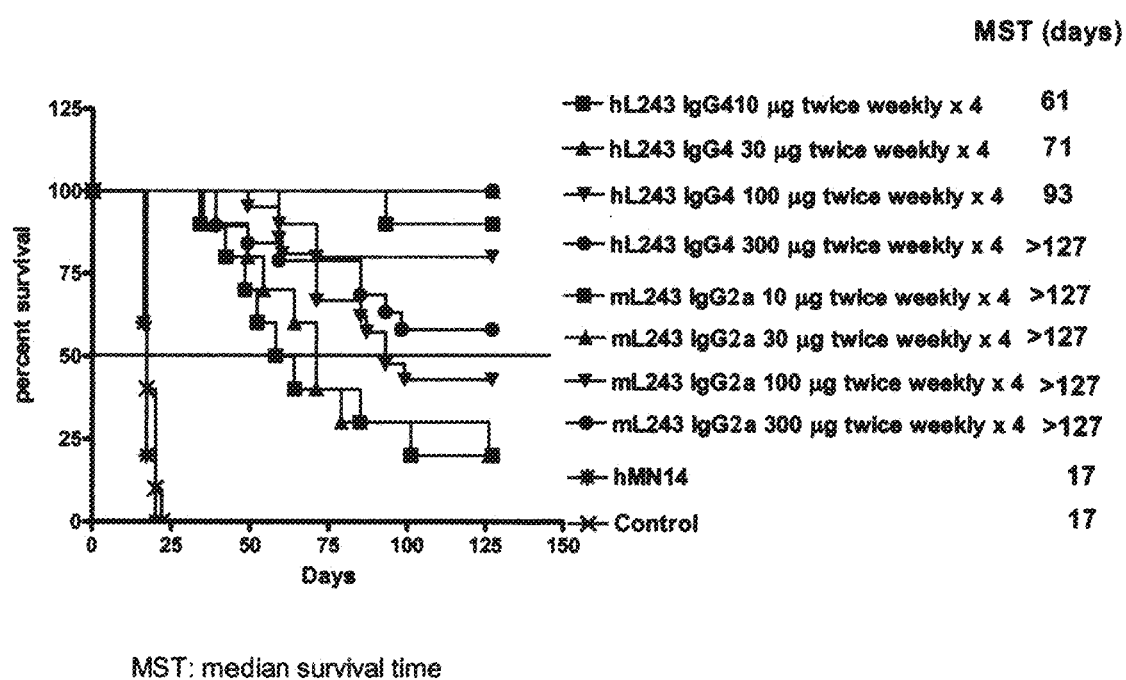

FIG. 21 illustrates therapy of Raji-bearing SCID mice with murine L243 and L243 γ4P.

Figures 22A, 22B, 22C:
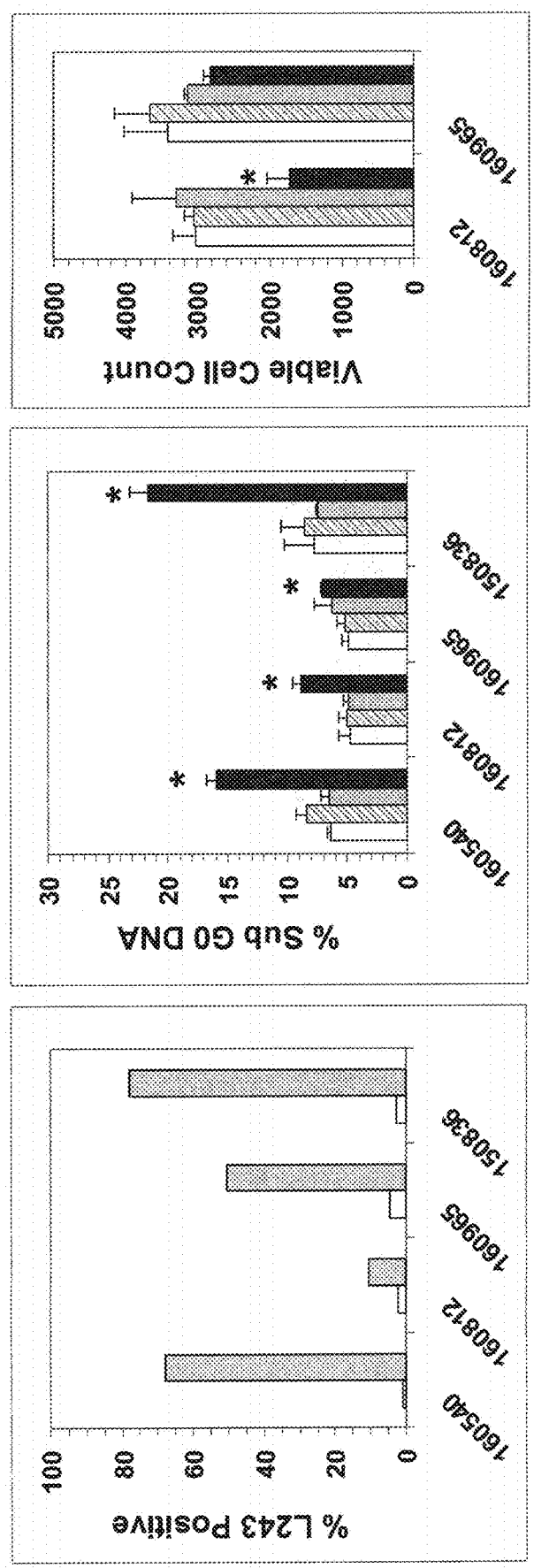

FIG. 22A. In vitro effects of murine L243 on canine lymphoma aspirates. L234 binding to the aspirates from 4 dogs. White bars, Ag8; gray bars, L243.

FIG. 22B. In vitro effects of murine L243 on canine lymphoma aspirates. Percent apoptotic cells as measured by flow cytometry of hypodiploid DNA (sub G0) following propidium iodine staining. Incubations were performed without second antibody or in the presence of goat anti-mouse IgG: white bars, Ag8 without second antibody; striped bars, Ag8 with GAM; gray bars, L243 without second antibody; black bars, L243 with GAM; *, P<0.05 vs. Ag8.

FIG. 22C. In vitro effects of murine L243 on canine lymphoma aspirates. Viable cell count was performed on two of the specimens by flow cytometry analysis of the cell count within a viable gate defined in the forward scatter vs. side scatter dot plot: white bars, Ag8 without second antibody; striped bars, Ag8 with GAM; gray bars, L243 without second antibody; black bars, L243 with GAM; *, P<0.05 vs. Ag8.

FIG. 23A. In vitro effects of IMMU-114 on canine lymphoma aspirates. Percent apoptotic cells as measured by flow cytometry of hypodiploid DNA (sub G0) following propidium iodine staining. Incubations were performed without second antibody or in the presence of goat anti-mouse IgG (GAM) or goat anti-human IgG (GAH). Error bars, SD of three replicates. *, significant change (P<0.05) relative to no mAb control.

FIG. 23B. In vitro effects of IMMU-114 on canine lymphoma aspirates. Percent specific lysis in CDC assays on aspirate of dog #171205. Error bars, SD of three replicates. *, significant change (P<0.05) relative to no mAb control.

FIG. 23C. In vitro effects of IMMU-114 on canine lymphoma aspirates. Percent specific lysis in ADCC assays on aspirate of dog #171205. Error bars, SD of three replicates. *, significant change (P<0.05) relative to no mAb control.

Figure 24:
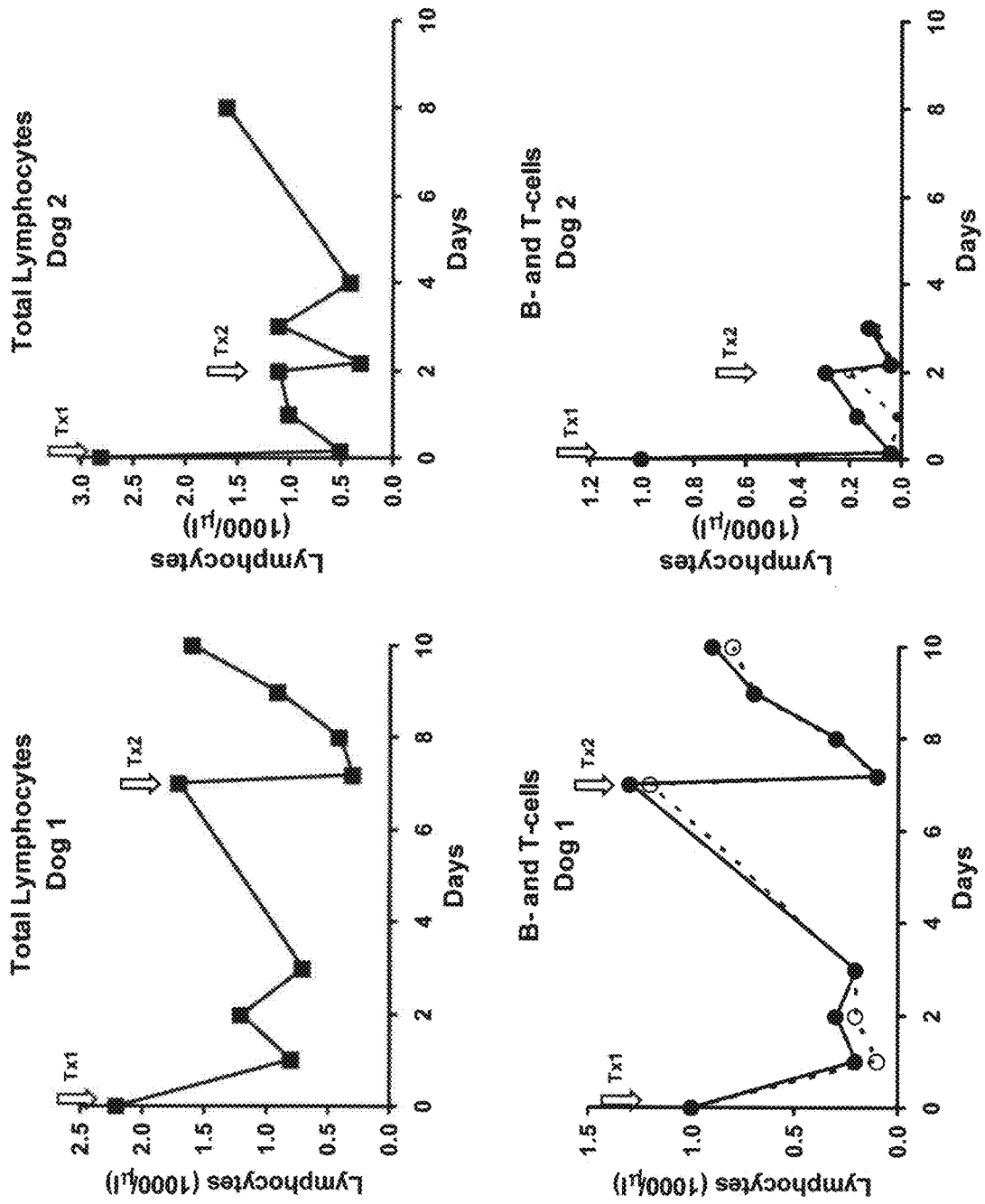

FIG. 24. Peripheral blood lymphocyte count and lymphocyte subset phenotyping indicated a decrease in both B- and T-cell lymphocytes. ■, total lymphocyte count; ●, T-cell count, relative to baseline; ○, B cell count, relative to baseline.

Figure 25:
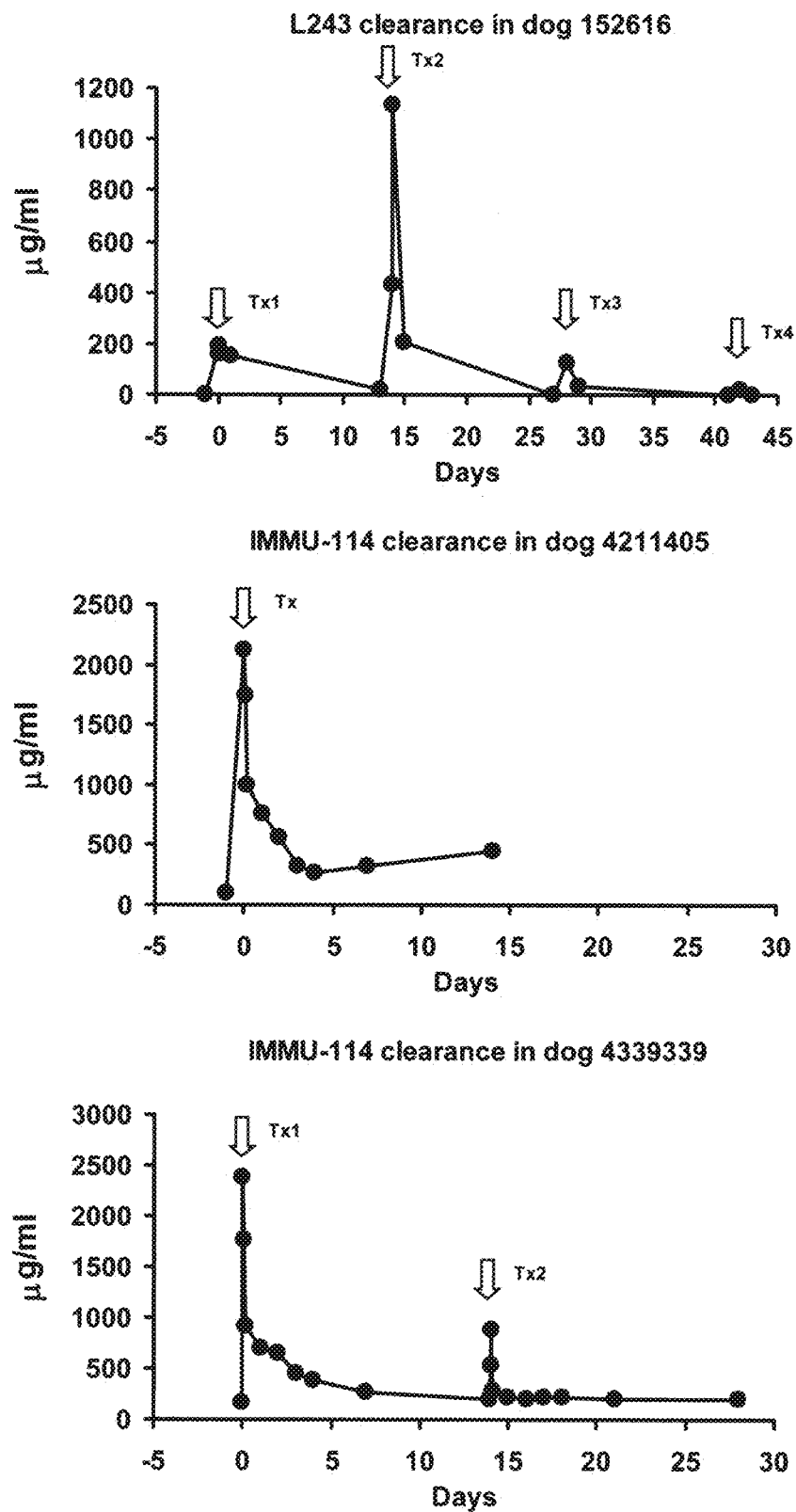

FIG. 25. Clearance of L243 in a dog with lymphoma (upper) and of IMMU-114 in two normal dogs (middle and lower). The L243 doses administered in the dog with lymphoma (upper) were 1.5 mg/kg for treatment 1 and 3.0 mg/kg for the remaining 3 treatments. IMMU-114 doses were 3.0 mg/kg for the initial dose in both normal dogs (middle and lower). The second dose of IMMU-114 administered to second normal dog (lower) was 1.3 mg/kg.

Figure 26:
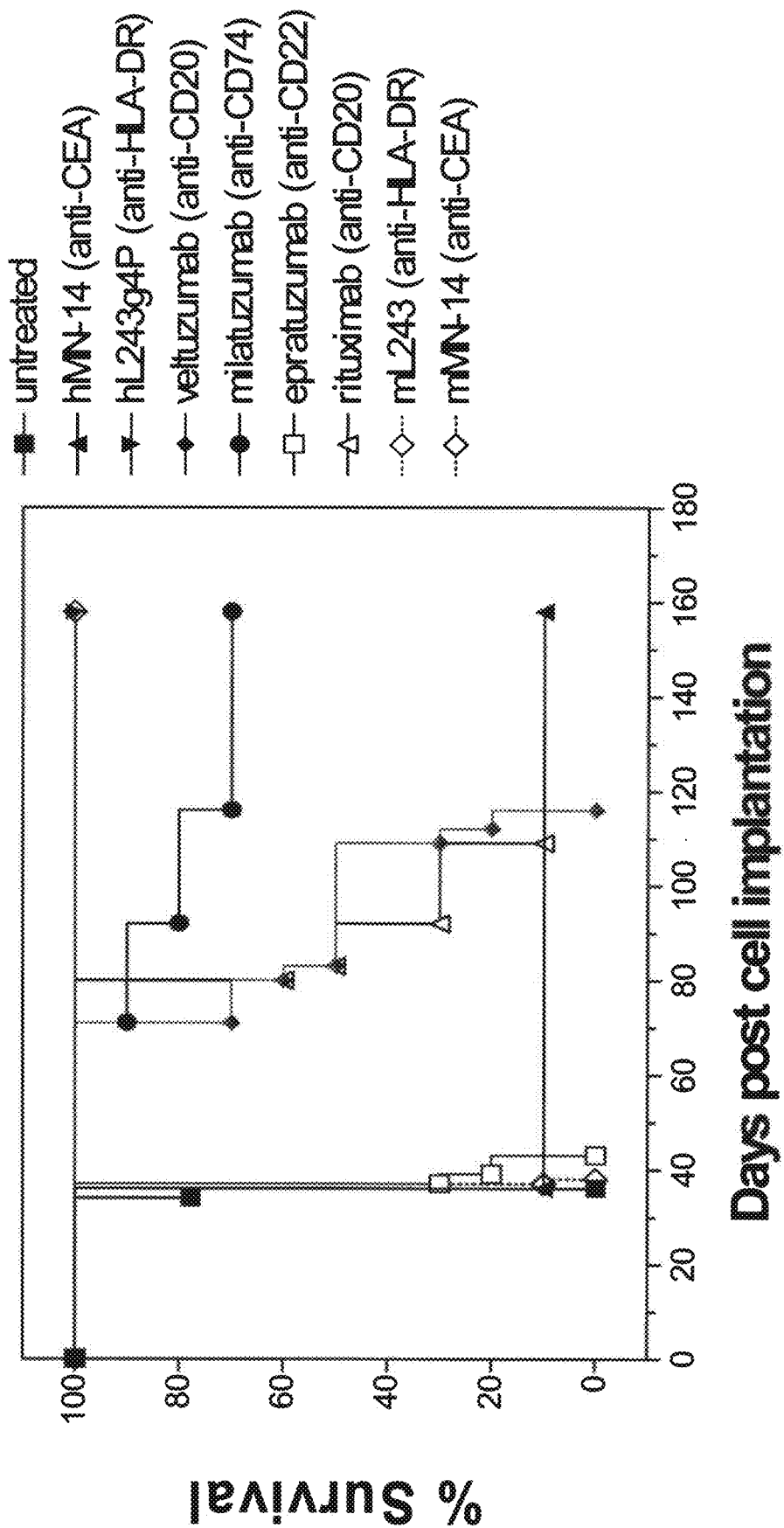

FIG. 26. Effect of different specificity antibodies on survival. 250 μg of the indicated antibodies was injected twice per week for 4 weeks, starting 1 day after injection of WSU-FSCCL tumor cells.

Figure 27:
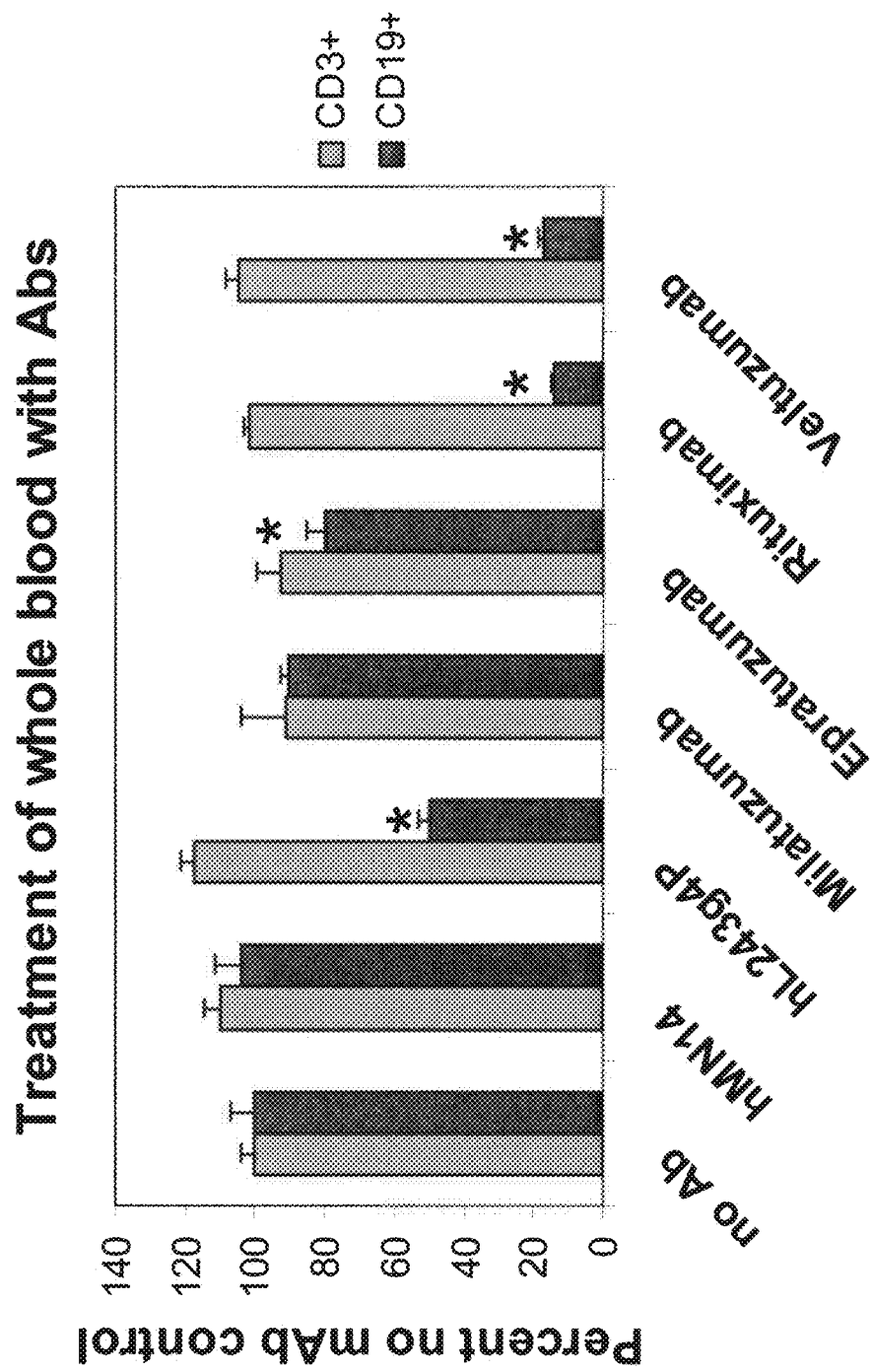

FIG. 27. Ex vivo effects of mAbs on whole blood. Heparinized whole blood of healthy volunteers was incubated with mAbs then assayed by flow cytometry. Data are shown as % of untreated control. Error bars, SD of 3 replicates. *, P<0.05 relative to no mAb control.

Figure 28:
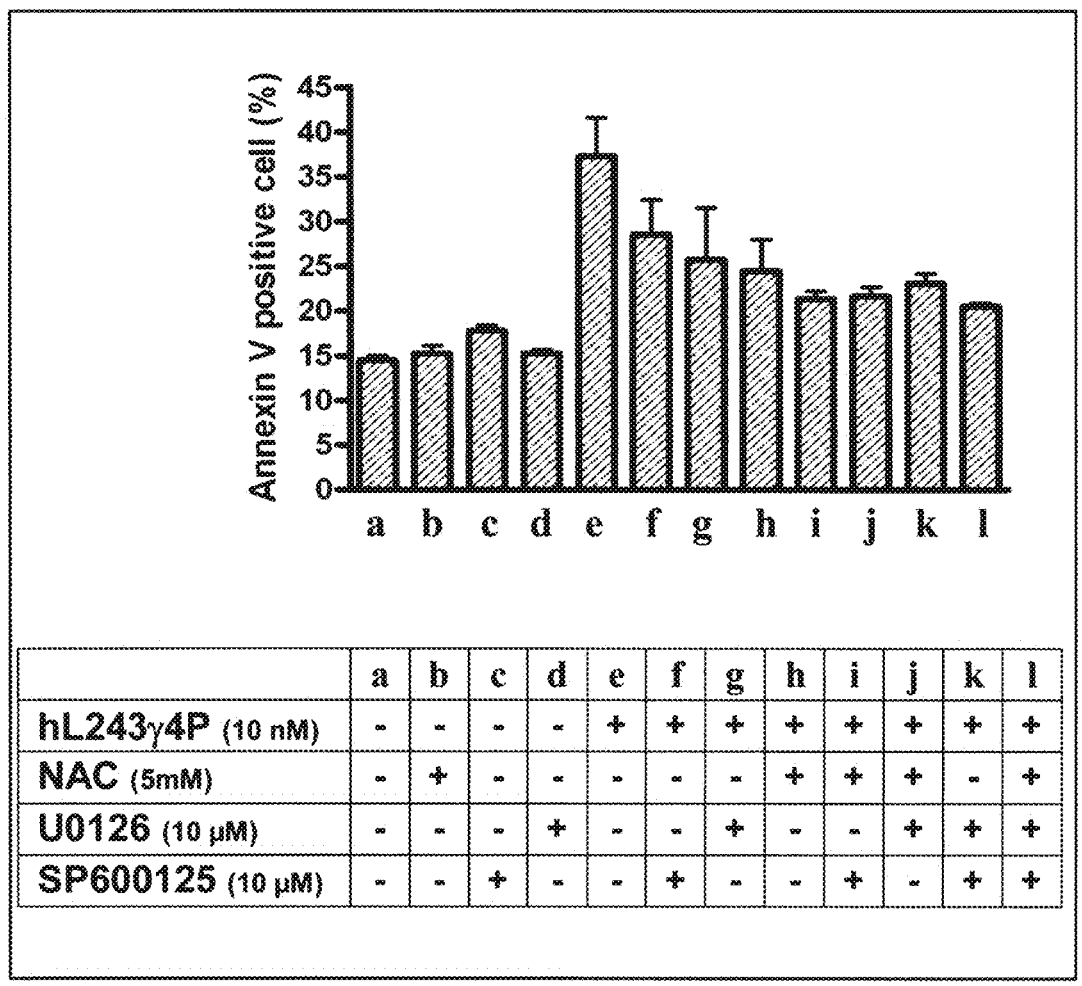

FIG. 28. Effect of ERK, JNK and ROS inhibitors on hL234g4P mediated apoptosis in Raji cells.

Figure 29:
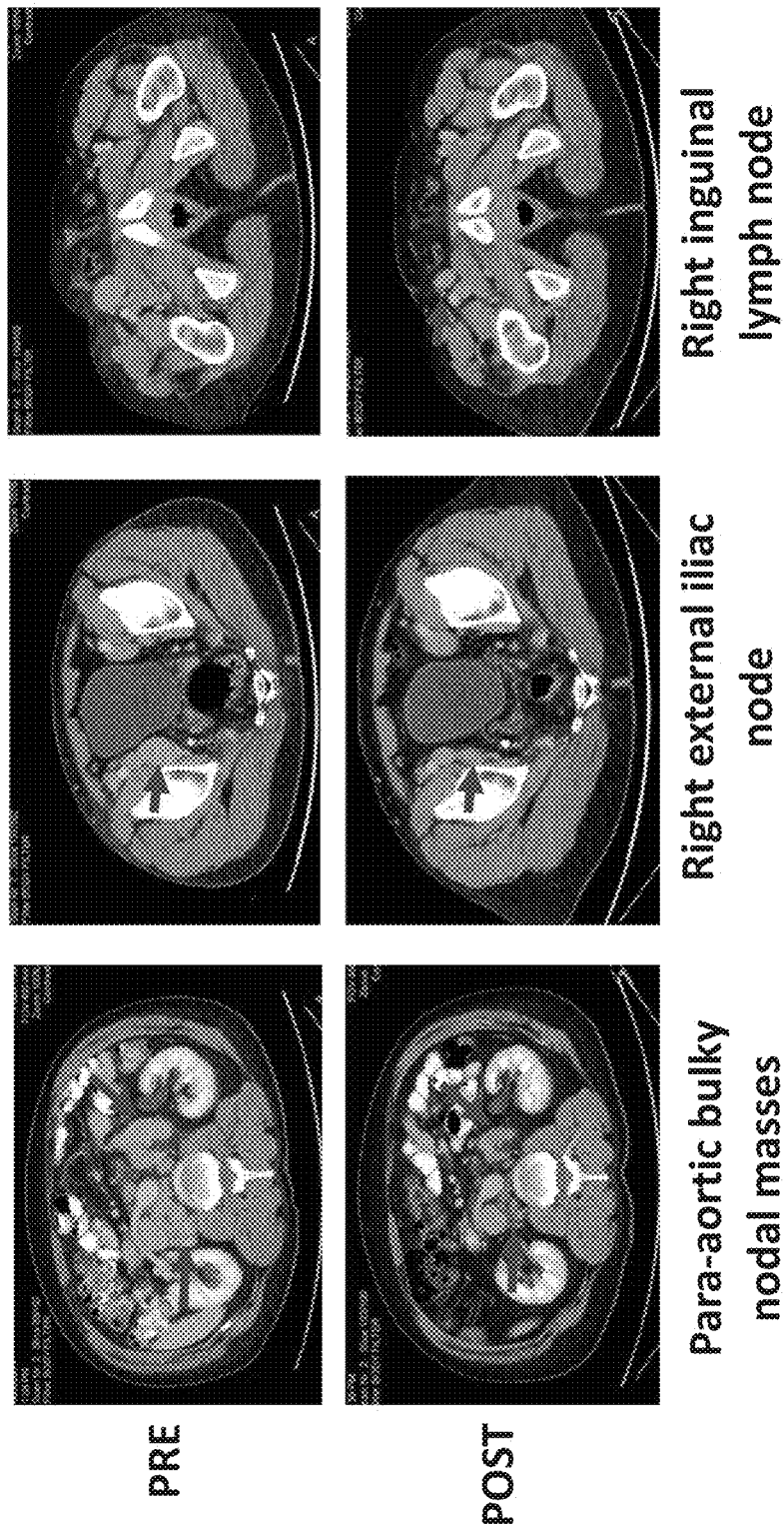

FIG. 29. Tumor reduction in a patient with follicular lymphoma treated with anti-HLA-DR antibody.

DETAILED DESCRIPTION

Definitions

Unless otherwise specified, "a" or "an" means "one or more".

"Antibody-dependent cell mediated cytotoxicity" or "ADCC" is a cell-mediated reaction in which nonspecific cytotoxic cells that express Fc receptors (natural killer cells, neutrophils, and macrophages) recognize bound antibody on target cells and subsequently cause lysis of the target cells. The primary cells for mediating ADCC are the natural killer cells (express the FcDRIII only) and monocytes (express FcDRI, FcDRII and FcDRIII).

"Complement-dependent cytotoxicity" or "CDC" refers to the lysing of a target in the presence of complement. The complement activation pathway is initiated by the binding of the first component of the complement system (C1q) to a molecule (eg, an antibody) complexed with a cognate antigen.

The "Fc receptor" or "FcR" is used to describe a receptor that binds to the Fc region of an antibody. Both CDC and ADCC require the Fc portion of a MAb and the effect of ADCC can be augmented by increasing the binding affinity for FcγR (IgG Fc receptors) on effector cells (Shinkawa, et al, *J Biol Chem* 278: 3466-3473, 23; Shields et al, *J Biol Chem* 211: 26733-2674, 22; Shields et al, *J Biol Chem* 276: 6591-664, 22; Davies et al, *Biotechnol Bioeng* 74: 288-294, 21; and Umana et al, *Nature Biotechnol* 176-18, 1999).

An "antibody" as used herein refers to a full-length (ie, naturally occurring or formed by normal immunoglobulin gene fragment recombinatorial processes) immunoglobulin molecule (eg, an IgG antibody) or an immunologically active (ie, specifically binding) portion of an immunoglobulin molecule, like an antibody fragment. An "antibody" includes monoclonal, polyclonal, bispecific, multispecific, murine, chimeric, humanized and human antibodies.

A "naked antibody" is an antibody or antigen binding fragment thereof that is not attached to a therapeutic or diagnostic agent. The Fc portion of an intact naked antibody can provide effector functions, such as complement fixation and ADCC (see, e.g., Markrides, *Pharmacol Rev* 50:59-87, 1998). Other mechanisms by which naked antibodies induce cell death may include apoptosis. (Vaswani and Hamilton, *Ann Allergy Asthma Immunol* 81: 105-119,1998.)

An "antibody fragment" is a portion of an intact antibody such as F(ab')$_2$, F(ab)$_2$, Fab', Fab, Fv, sFv, scFv and the like. Regardless of structure, an antibody fragment binds with the same antigen that is recognized by the full-length antibody. For example, antibody fragments include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). "Single-chain antibodies", often abbreviated as "scFv" consist of a polypeptide chain that comprises both a $V_H$ and a $V_L$ domain which interact to form an antigen-binding site. The $V_H$ and $V_L$ domains are usually linked by a peptide of 1 to 25 amino acid residues. Antibody fragments also include diabodies, triabodies and single domain antibodies (dAb).

Humanized L243 Antibodies

In preferred embodiments, the subject anti-HLA-DR antibody may be a humanized L243 antibody. Such antibodies bind to the same epitope on HLA-DR as the parental murine L243 antibody, but have reduced immunogenicity. mL243 is a monoclonal antibody previously described by Lampson & Levy (J Immunol, 1980, 125:293). The amino acid sequences of the light and heavy chain variable regions of the mL243 antibody are shown in FIG. 1 and FIG. 2. mL243 has been deposited at the American Type Culture Collection, Rockville, Md., under Accession number ATCC HB55.

The humanized L243 antibodies may comprise the L243 heavy chain CDR sequences CDR1 (NYGMN (SEQ ID NO: 39)), CDR2 (WINTYTREPTYADDFKG (SEQ ID NO: 40)) and CDR3 (DITAVVPTGFDY (SEQ ID NO: 41)) and the light chain CDR sequences CDR1 (RASENIYSNLA (SEQ ID NO: 42)), CDR2 (AASNLAD (SEQ ID NO: 43)), and CDR3 (QHFWTTPWA (SEQ ID NO: 44)), attached to human antibody FR and constant region sequences. In more preferred embodiments, one or more murine FR amino acid residues are substituted for the corresponding human FR residues, particularly at locations adjacent to or nearby the CDR residues. Exemplary murine $V_H$ residues that may be substituted in the humanized design are at positions: F27, K38, K46, A68 and F91. Exemplary murine $V_L$ residues that may be substituted in the humanized design are at positions R37, K39, V48, F49, and G1. Further details for humanizing antibody sequences, while retaining the antigenic specificity of the original non-human antibody, are disclosed in the Examples below.

A particularly preferred form of hL243 antibody is illustrated in FIG. 3 and FIG. 4, incorporating FR sequences from the human RF-TS3, NEWM and REI antibodies. However, in other embodiments, the FR residues may be derived from any suitable human immunoglobulin, provided that the humanized antibody can fold such that it retains the ability to specifically bind HLA-DR. Preferably the type of human framework (FR) used is of the same/similar class/type as the donor antibody. More preferably, the human FR sequences are selected to have a high degree of sequence homology with the corresponding murine FR sequences, particularly at positions spatially close or adjacent to the CDRs. In accordance with this embodiment, the frameworks (ie, FR1-4) of the humanized L243 $V_H$ or $V_L$ may be derived from a combination of human antibodies. Examples of human frameworks which may be used to construct CDR-grafted humanized antibodies are LAY, POM, TUR, TEI, KOL, NEWM, REI, RF and EU. Preferably human RF-TS3

FR1-3 and NEWM FR4 are used for the heavy chain and REI FR1-4 are used for the light chain. The variable domain residue numbering system used herein is described in Kabat et al, (1991), Sequences of Proteins of Immunological Interest, 5th Edition, United States Department of Health and Human Services The light and heavy chain variable domains of the humanized antibody molecule may be fused to human light or heavy chain constant domains. The human constant domains may be selected with regard to the proposed function of the antibody. In one embodiment, the human constant domains may be selected based on a lack of effector functions. The heavy chain constant domains fused to the heavy chain variable region may be those of human IgA ($\alpha$1 or $\alpha$2 chain), IgG ($\gamma$1, $\gamma$2, $\gamma$3 or $\gamma$4 chain) or IgM ($\mu$ chain). The light chain constant domains which may be fused to the light chain variable region include human lambda and kappa chains.

In one particular embodiment of the present invention, a $\gamma$1 chain is used. In yet another particular embodiment, a $\gamma$4 chain is used. The use of the $\gamma$4 chain may in some cases increase the tolerance to hL243 in subjects (decreased side effects and infusion reactions, etc).

In one embodiment, analogues of human constant domains may be used. These include but are not limited to those constant domains containing one or more additional amino acids than the corresponding human domain or those constant domains wherein one or more existing amino acids of the corresponding human domain have been deleted or altered. Such domains may be obtained, for example, by oligonucleotide directed mutagenesis.

In a particular embodiment, an anti-HLA-DR antibody or fragment thereof may be a fusion protein. The fusion protein may contain one or more anti-HLA-DR antibodies or fragments thereof. In various embodiments, the fusion protein may also comprise one or more additional antibodies against a different antigen, or may comprise a different effector protein or peptide, such as a cytokine. For example, the different antigen may be a tumor marker selected from a B cell lineage antigen, (eg, CD19, CD20, or CD22) for the treatment of B cell malignancies. In another example, the different antigen may be expressed on other cells that cause other types of malignancies. Further, the cell marker may be a non-B cell lineage antigen, such as selected from the group consisting of HLA-DR, CD3, CD33, CD52, CD66, MUC1 and TAC.

In one embodiment, an anti-HLA-DR antibody may be combined with other antibodies and used to treat a subject having or suspected of developing a disease. In accordance with this embodiment, an anti-HLA-DR antibody or fragment thereof may be combined with an anticancer monoclonal antibody such as a humanized monoclonal antibody (eg hA20, anti-CD20 Mab) and used to treat cancer. It is contemplated herein that an anti-HLA-DR antibody may be used as a separate antibody composition in combination with one or more other separate antibody compositions, or used as a bi-functional antibody containing, for example, one anti-HLA-DR and one other anti-tumor antibody, such as hA20. In another particular embodiment, the antibody may target a B cell malignancy. The B cell malignancy may consist of indolent forms of B cell lymphomas, aggressive forms of B cell lymphomas, chronic lymphatic leukemias, acute lymphatic leukemias, Waldenstrom's macroglobulinemia, and multiple myeloma. Other non-malignant B cell disorders and related diseases that may be treated with the subject antibodies include many autoimmune and immune dysregulatory diseases, such as septicemia and septic shock.

Antibodies and Antibody Fragments

Techniques for preparing monoclonal antibodies against virtually any target antigen are well known in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures. In preferred embodiments, the antigen is a human antigen.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art. The use of antibody components derived from humanized, chimeric or human antibodies obviates potential problems associated with the immunogenicity of murine constant regions.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., Proc. Nat'l Acad. Sci. USA 86: 3833 (1989). Techniques for constructing chimeric antibodies are well known to those of skill in the art. As an example, Leung et al., Hybridoma 13:469 (1994), produced an LL2 chimera by combining DNA sequences encoding the $V_\kappa$ and $V_H$ domains of murine LL2, an anti-CD22 monoclonal antibody, with respective human $\kappa$ and $IgG_1$ constant region domains.

Humanized Antibodies

Techniques for producing humanized MAbs are well known in the art (see, e.g., Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Generally, those human FR amino acid residues that differ from their murine counterparts and are located close to or touching one or more CDR amino acid residues would be candidates for substitution.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50). A fully human antibody also can be constructed by genetic or chromosomal transfection methods, as well as phage display technology, all of which are known in the art. See for example, McCafferty et al., *Nature* 348:552-553 (1990). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art (see, e.g., Pasqualini and Ruoslahti, 1996, Nature 380:364-366; Pasqualini, 1999, The Quart. J. Nucl. Med. 43:159-162).

Phage display can be performed in a variety of formats, for their review, see e.g. Johnson and Chiswell, *Current Opinion in Structural Biology* 3:5564-571 (1993). Human antibodies may also be generated by in vitro activated B cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Antibody Fragments

Antibody fragments which recognize specific epitopes can be generated by known techniques. Antibody fragments are antigen binding portions of an antibody, such as $F(ab')_2$, Fab', $F(ab)_2$, Fab, Fv, sFv and the like. $F(ab')_2$ fragments can be produced by pepsin digestion of the antibody molecule and Fab' fragments can be generated by reducing disulfide bridges of the $F(ab')_2$ fragments. Alternatively, Fab' expression libraries can be constructed (Huse et al., 1989, *Science*, 246:1274-1281) to allow rapid and easy identification of monoclonal Fab' fragments with the desired specificity. $F(ab)_2$ fragments may be generated by papain digestion of an antibody and Fab fragments obtained by disulfide reduction.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are described in U.S. Pat. No. 4,704,692, U.S. Pat. No. 4,946,778, R. Raag and M. Whitlow, "*Single Chain Fvs.*" FASEB Vol 9:73-80 (1995) and R. E. Bird and B. W. Walker, "*Single Chain Antibody Variable Regions*," TIBTECH, Vol 9: 132-137 (1991).

Techniques for producing single domain antibodies (DABs) are also known in the art, as disclosed for example in Cossins et al. (2006, *Prot Express Purif* 51:253-259), incorporated herein by reference.

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. These methods are described, for example, by Goldenberg, U.S. Pat. Nos. 4,036,945 and 4,331,647 and references contained therein. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Known Antibodies

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312, 318; 7,282,567; 7,151,164; 7,074,403; 7,060,802; 7,056, 509; 7,049,060; 7,045,132; 7,041,803; 7,041,802; 7,041, 293; 7,038,018; 7,037,498; 7,012,133; 7,001,598; 6,998, 468; 6,994,976; 6,994,852; 6,989,241; 6,974,863; 6,965, 018; 6,964,854; 6,962,981; 6,962,813; 6,956,107; 6,951, 924; 6,949,244; 6,946,129; 6,943,020; 6,939,547; 6,921, 645; 6,921,645; 6,921,533; 6,919,433; 6,919,078; 6,916, 475; 6,905,681; 6,899,879; 6,893,625; 6,887,468; 6,887, 466; 6,884,594; 6,881,405; 6,878,812; 6,875,580; 6,872, 568; 6,867,006; 6,864,062; 6,861,511; 6,861,227; 6,861, 226; 6,838,282; 6,835,549; 6,835,370; 6,824,780; 6,824, 778; 6,812,206; 6,793,924; 6,783,758; 6,770,450; 6,767, 711; 6,764,688; 6,764,681; 6,764,679; 6,743,898; 6,733, 981; 6,730,307; 6,720,155; 6,716,966; 6,709,653; 6,693, 176; 6,692,908; 6,689,607; 6,689,362; 6,689,355; 6,682, 737; 6,682,736; 6,682,734; 6,673,344; 6,653,104; 6,652, 852; 6,635,482; 6,630,144; 6,610,833; 6,610,294; 6,605, 441; 6,605,279; 6,596,852; 6,592,868; 6,576,745; 6,572, 856; 6,566,076; 6,562,618; 6,545,130; 6,544,749; 6,534, 058; 6,528,625; 6,528,269; 6,521,227; 6,518,404; 6,511, 665; 6,491,915; 6,488,930; 6,482,598; 6,482,408; 6,479, 247; 6,468,531; 6,468,529; 6,465,173; 6,461,823; 6,458, 356; 6,455,044; 6,455,040; 6,451,310; 6,444,206; 6,441, 143; 6,432,404; 6,432,402; 6,419,928; 6,413,726; 6,406, 694; 6,403,770; 6,403,091; 6,395,276; 6,395,274; 6,387, 350; 6,383,759; 6,383,484; 6,376,654; 6,372,215; 6,359, 126; 6,355,481; 6,355,444; 6,355,245; 6,355,244; 6,346, 246; 6,344,198; 6,340,571; 6,340,459; 6,331,175; 6,306, 393; 6,254,868; 6,187,287; 6,183,744; 6,129,914; 6,120, 767; 6,096,289; 6,077,499; 5,922,302; 5,874,540; 5,814, 440; 5,798,229; 5,789,554; 5,776,456; 5,736,119; 5,716, 595; 5,677,136; 5,587,459; 5,443,953, 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Exemplary antibodies that may be utilized include, but are not limited to, hR1 (anti-IGF-1R, U.S. patent application Ser. No. 13/688,812, filed Nov. 29, 2012), hPAM4 (anti-mucin, U.S. Pat. No. 7,282,567), hA20 (anti-CD20, U.S. Pat. No. 7,151,164), hA19 (anti-CD19, U.S. Pat. No. 7,109, 304), hIMMU31 (anti-AFP, U.S. Pat. No. 7,300,655), hLL1 (anti-CD74, U.S. Pat. No. 7,312,318), hLL2 (anti-CD22, U.S. Pat. No. 5,789,554), hMu-9 (anti-CSAp, U.S. Pat. No. 7,387,772), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 8,287,865), hRS7 (anti-EGP-1, U.S. Pat. No. 7,238,785), hMN-3 (anti-CEACAM6, U.S. Pat. No. 7,541,440), Ab124 and Ab125 (anti-CXCR4, U.S. Pat. No. 7,138,496), the Examples section of each cited patent or application incorporated herein by reference. More preferably, the antibody is IMMU-31 (anti-AFP), hRS7 (anti-TROP-2), hMN-14 (anti-CEACAM5), hMN-3 (anti-CEACAM6), hMN-15 (anti-CEACAM6), hLL1 (anti-CD74), hLL2 (anti-CD22), hL243 or IMMU-114 (anti-HLA-DR), hA19 (anti-CD19) or hA20 (anti-CD20). As used herein, the terms epratuzumab and hLL2 are interchangeable, as are the terms veltuzumab and hA20, hL243g4P, hL243gamma4P and IMMU-114.

Alternative antibodies of use include, but are not limited to, abciximab (anti-glycoprotein IIb/IIIa), alemtuzumab (anti-CD52), bevacizumab (anti-VEGF), cetuximab (anti-EGFR), gemtuzumab (anti-CD33), ibritumomab (anti-CD20), panitumumab (anti-EGFR), rituximab (anti-CD20), tositumomab (anti-CD20), trastuzumab (anti-ErbB2), lambrolizumab (anti-PD-1 receptor), nivolumab (anti-PD-1 receptor), ipilimumab (anti-CTLA-4), abagovomab (anti-CA-125), adecatumumab (anti-EpCAM), atlizumab (anti-IL-6 receptor), benralizumab (anti-CD125), obinutuzumab (GA101, anti-CD20), CC49 (anti-TAG-72), AB-PG1-XG1-026 (anti-PSMA, U.S. patent application Ser. No. 11/983, 372, deposited as ATCC PTA-4405 and PTA-4406), D2/B (anti-PSMA, WO 2009/130575), tocilizumab (anti-IL-6 receptor), basiliximab (anti-CD25), daclizumab (anti-CD25), efalizumab (anti-CD11a), GA101 (anti-CD20; Glycart Roche), natalizumab (anti-.alpha.4 integrin), omalizumab (anti-IgE); anti-TNF-.alpha. antibodies such as CDP571 (Ofei et al., 2011, Diabetes 45:881-85), MTNFAI, M2TNFAI, M3TNFAI, M3TNFABI, M302B, M303 (Thermo Scientific, Rockford, Ill.), infliximab (Centocor, Malvern, Pa.), certolizumab pegol (UCB, Brussels, Belgium), anti-CD40L (UCB, Brussels, Belgium), adalimumab (Abbott, Abbott Park, Ill.), or Benlysta (Human Genome Sciences).

A comprehensive analysis of suitable antigen (Cluster Designation, or CD) targets on hematopoietic malignant cells, as shown by flow cytometry and which can be a guide to selecting suitable antibodies for drug-conjugated immunotherapy, is Craig and Foon, Blood prepublished online Jan. 15, 2008; DOL 10.1182/blood-2007-11-120535.

The CD66 antigens consist of five different glycoproteins with similar structures, CD66a-e, encoded by the carcinoembryonic antigen (CEA) gene family members, BCG, CGM6, NCA, CGM1 and CEA, respectively. These CD66 antigens (e.g., CEACAM6) are expressed mainly in granulocytes, normal epithelial cells of the digestive tract and tumor cells of various tissues. Also included as suitable targets for cancers are cancer testis antigens, such as NY-ESO-1 (Theurillat et al., Int. J. Cancer 2007; 120(11):2411-7), as well as CD79a in myeloid leukemia (Kozlov et al., Cancer Genet. Cytogenet. 2005; 163(1):62-7) and also B-cell diseases, and CD79b for non-Hodgkin's lymphoma (Poison et al., Blood 110(2):616-623). A number of the aforementioned antigens are disclosed in U.S. Provisional Application Ser. No. 60/426,379, entitled "Use of Multi-specific, Non-covalent Complexes for Targeted Delivery of Therapeutics," filed Nov. 15, 2002. Cancer stem cells, which are ascribed to be more therapy-resistant precursor malignant cell populations (Hill and Penis, J. Natl. Cancer Inst. 2007; 99:1435-40), have antigens that can be targeted in certain cancer types, such as CD133 in prostate cancer (Maitland et al., Ernst Schering Found. Sympos. Proc. 2006; 5:155-79), non-small-cell lung cancer (Donnenberg et al., J. Control Release 2007; 122(3):385-91), and glioblastoma (Beier et al., Cancer Res. 2007; 67(9):4010-5), and CD44 in colorectal cancer (Dalerba er al., Proc. Natl. Acad. Sci. USA 2007; 104(24) 10158-63), pancreatic cancer (Li et al., Cancer Res. 2007; 67(3):1030-7), and in head and neck squamous cell carcinoma (Prince et al., Proc. Natl. Acad. Sci. USA 2007; 104(3)973-8).

For multiple myeloma therapy, suitable targeting antibodies have been described against, for example, CD38 and CD138 (Stevenson, Mol Med 2006; 12(11-12):345-346; Tassone et al., Blood 2004; 104(12):3688-96), CD74 (Stein et al., ibid.), CS1 (Tai et al., Blood 2008; 112(4):1329-37, and CD40 (Tai et al., 2005; Cancer Res. 65(13):5898-5906).

Macrophage migration inhibitory factor (MIF) is an important regulator of innate and adaptive immunity and apoptosis. It has been reported that CD74 is the endogenous receptor for MIF (Leng et al., 2003, J Exp Med 197:1467-76). The therapeutic effect of antagonistic anti-CD74 antibodies on MIF-mediated intracellular pathways may be of use for treatment of a broad range of disease states, such as cancers of the bladder, prostate, breast, lung, colon and chronic lymphocytic leukemia (e.g., Meyer-Siegler et al., 2004, BMC Cancer 12:34; Shachar & Haran, 2011, Leuk Lymphoma 52:1446-54); autoimmune diseases such as rheumatoid arthritis and systemic lupus erythematosus (Morand & Leech, 2005, Front Biosci 10:12-22; Shachar & Haran, 2011, Leuk Lymphoma 52:1446-54); kidney diseases such as renal allograft rejection (Lan, 2008, Nephron Exp Nephrol. 109:e79-83); and numerous inflammatory diseases (Meyer-Siegler et al., 2009, Mediators Inflamm epub Mar. 22, 2009; Takahashi et al., 2009, Respir Res 10:33; Milatuzumab (hLL1) is an exemplary anti-CD74 antibody of therapeutic use for treatment of MIF-mediated diseases.

Anti-TNF-.alpha. antibodies are known in the art and may be of use to treat immune diseases, such as autoimmune disease, immune dysfunction (e.g., graft-versus-host disease, organ transplant rejection) or diabetes. Known antibodies against TNF-.alpha. include the human antibody CDP571 (Ofei et al., 2011, Diabetes 45:881-85); murine antibodies MTNFAI, M2TNFAI, M3TNFAI, M3TNFABI, M302B and M303 (Thermo Scientific, Rockford, Ill.); infliximab (Centocor, Malvern, Pa.); certolizumab pegol (UCB, Brussels, Belgium); and adalimumab (Abbott, Abbott Park, Ill.). These and many other known anti-TNF-.alpha. antibodies may be used in the claimed methods and compositions. Other antibodies of use for therapy of immune dysregulatory or autoimmune disease include, but are not limited to, anti-B-cell antibodies such as veltuzumab, epratuzumab, milatuzumab or hL243; tocilizumab (anti-IL-6 receptor); basiliximab (anti-CD25); daclizumab (anti-CD25); efalizumab (anti-CD11a); muromonab-CD3 (anti-CD3 receptor); anti-CD40L (UCB, Brussels, Belgium); natalizumab (anti-.alpha.4 integrin) and omalizumab (anti-IgE).

Studies with checkpoint inhibitor antibodies for cancer therapy have generated unprecedented response rates in cancers previously thought to be resistant to cancer treatment (see, e.g., Ott & Bhardwaj, 2013, Frontiers in Immunology 4:346; Menzies & Long, 2013, Ther Adv Med Oncol 5:278-85; Pardoll, 2012, Nature Reviews 12:252-264; Mavilio & Lugli,). Therapy with antagonistic checkpoint blocking antibodies against CTLA-4, PD-1 and PD-L1 are one of the most promising new avenues of immunotherapy for cancer and other diseases. In contrast to the majority of anti-cancer agents, checkpoint inhibitor do not target tumor cells directly, but rather target lymphocyte receptors or their ligands in order to enhance the endogenous antitumor activity of the immune system. (Pardoll, 2012, Nature Reviews 12:252-264) Because such antibodies act primarily by regulating the immune response to diseased cells, tissues or pathogens, they may be used in combination with other therapeutic modalities, such as the subject anti-HLA-DR antibodies, to enhance their anti-tumor effect.

Programmed cell death protein 1 (PD-1, also known as CD279) encodes a cell surface membrane protein of the immunoglobulin superfamily, which is expressed in B cells and NK cells (Shinohara et al., 1995, Genomics 23:704-6; Blank et al., 2007, Cancer Immunol Immunother 56:739-45; Finger et al., 1997, Gene 197:177-87; Pardoll, 2012, Nature Reviews 12:252-264). Anti-PD1 antibodies have been used for treatment of melanoma, non-small-cell lung cancer, bladder cancer, prostate cancer, colorectal cancer, head and neck cancer, triple-negative breast cancer, leukemia, lymphoma and renal cell cancer (Topalian et al., 2012, N Engl J Med 366:2443-54; Lipson et al., 2013, Clin Cancer Res 19:462-8; Berger et al., 2008, Clin Cancer Res 14:3044-51; Gildener-Leapman et al., 2013, Oral Oncol 49:1089-96; Menzies & Long, 2013, Ther Adv Med Oncol 5:278-85).

Exemplary anti-PD1 antibodies include lambrolizumab (MK-3475, MERCK), nivolumab (BMS-936558, BRISTOL-MYERS SQUIBB), and pidilizumab (CT-011, CURETECH LTD.). Anti-PD1 antibodies are commercially available, for example from ABCAM® (AB137132), BIOLEGEND® (EH12.2H7, RMP1-14) and AFFYMETRIX EBIOSCIENCE (J105, J116, MIH4).

Programmed cell death 1 ligand 1 (PD-L1, also known as CD274) is a ligand for PD-1, found on activated T cells, B cells, myeloid cells and macrophages. The complex of PD-1 and PD-L1 inhibits proliferation of CD8+ T cells and reduces the immune response (Topalian et al., 2012, N Engl J Med 366:2443-54; Brahmer et al., 2012, N Eng J Med 366:2455-65). Anti-PDL1 antibodies have been used for treatment of non-small cell lung cancer, melanoma, colorectal cancer, renal-cell cancer, pancreatic cancer, gastric cancer, ovarian cancer, breast cancer, and hematologic malignancies (Brahmer et al., N Eng J Med 366:2455-65; Ott et al., 2013, Clin Cancer Res 19:5300-9; Radvanyi et al., 2013, Clin Cancer Res 19:5541; Menzies & Long, 2013, Ther Adv Med Oncol 5:278-85; Berger et al., 2008, Clin Cancer Res 14:13044-51).

Exemplary anti-PDL1 antibodies include MDX-1105 (MEDAREX), MEDI4736 (MEDIMMUNE) MPDL3280A (GENENTECH) and BMS-936559 (BRISTOL-MYERS SQUIBB). Anti-PDL1 antibodies are also commercially available, for example from AFFYMETRIX EBIOSCIENCE (MIH1).

Cytotoxic T-lymphocyte antigen 4 (CTLA-4, also known as CD152) is also a member of the immunoglobulin superfamily that is expressed exclusively on T-cells. CTLA-4 acts to inhibit T cell activation and is reported to inhibit helper T cell activity and enhance regulatory T cell immunosuppressive activity (Pardoll, 2012, Nature Reviews 12:252-264). Anti-CTL4A antibodies have been used in clinical trials for treatment of melanoma, prostate cancer, small cell lung cancer, non-small cell lung cancer (Robert & Ghiringhelli, 2009, Oncologist 14:848-61; Ott et al., 2013, Clin Cancer Res 19:5300; Weber, 2007, Oncologist 12:864-72; Wada et al., 2013, J Transl Med 11:89).

Exemplary anti-CTLA4 antibodies include ipilimumab (Bristol-Myers Squibb) and tremelimumab (PFIZER). Anti-PD1 antibodies are commercially available, for example from ABCAM® (AB134090), SINO BIOLOGICAL INC. (11159-H03H, 11159-H08H), and THERMO SCIENTIFIC PIERCE (PAS-29572, PAS-23967, PAS-26465, MA1-12205, MA1-35914). Ipilimumab has recently received FDA approval for treatment of metastatic melanoma (Wada et al., 2013, J Transl Med 11:89).

These and other known checkpoint inhibitor antibodies may be used in combination with anti-HLA-DR antibodies alone or in further combination with an interferon, such as interferon-a, for improved cancer therapy.

The person of ordinary skill will be aware that it is possible to generate any number of antibodies against a known and well characterized target antigen, such as human HLA-DR. The human HLA-DR antigen has been well characterized in the art, for example by its amino acid sequence (see, e.g., GenBank Accession No. ADM15723.1).

Antibody Allotypes

Immunogenicity of therapeutic antibodies is associated with increased risk of infusion reactions and decreased duration of therapeutic response (Baert et al., 2003, N Engl J Med 348:602-08). The extent to which therapeutic antibodies induce an immune response in the host may be determined in part by the allotype of the antibody (Stickler et al., 2011, Genes and Immunity 12:213-21). Antibody allotype is related to amino acid sequence variations at specific locations in the constant region sequences of the antibody. The allotypes of IgG antibodies containing a heavy chain γ-type constant region are designated as Gm allotypes (1976, J Immunol 117:1056-59).

For the common IgG1 human antibodies, the most prevalent allotype is G1m1 (Stickler et al., 2011, Genes and Immunity 12:213-21). However, the G1m3 allotype also occurs frequently in Caucasians (Id.). It has been reported that G1m1 antibodies contain allotypic sequences that tend to induce an immune response when administered to non-G1m1 (nG1m1) recipients, such as G1m3 patients (Id.). Non-G1m1 allotype antibodies are not as immunogenic when administered to G1m1 patients (Id.).

The human G1m1 allotype comprises the amino acids D12 (Kabat position 356) and L14 (Kabat position 358) in the CH3 sequence of the heavy chain IgG1. The nG1m1 allotype comprises the amino acids E12 and M14 at the same locations. Both G1m1 and nG1m1 allotypes comprise an E13 residue in between the two variable sites and the allotypes are sometimes referred to as DEL and EEM allotypes. A non-limiting example of the heavy chain constant region sequences for G1m1 and nG1m1 allotype antibodies is shown for the exemplary antibodies rituximab (SEQ ID NO:45) and veltuzumab (SEQ ID NO:46).

```
Rituximab heavy chain variable region sequence
                                  (SEQ ID NO: 45)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKA

EPKSCDKTHTCPPCPAPELLGGPSVFLEPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFELYSKLT

VDKSRWQQGNVFSCSVMHEALHNHYTQKSLSLSPGK

Veltuzumab heavy chain variable region
                                  (SEQ ID NO: 46)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKRV

EPKSCDKTHTCPPCPAPELLGGPSVFLEPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSREEMTKNQ

VSLTCLVKGFYPSDIAVEWESNGQPENNYKTTPPVLDSDGSFELYSKLT

VDKSRWQQGNVFSCSVMHEALHNHYTQKSLSLSPGK
```

With regard to therapeutic antibodies, veltuzumab and rituximab are, respectively, humanized and chimeric IgG1 antibodies against CD20, of use for therapy of a wide variety of hematological malignancies and/or autoimmune diseases. Table 1 compares the allotype sequences of rituximab vs. veltuzumab. As shown in Table 1, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, J Clin Oncol 27:3346-53; Goldenberg et al., 2009, Blood 113:1062-70; Robak & Robak, 2011, BioDrugs 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

| | | Heavy chain position and associated allotypes | | | | | |
|---|---|---|---|---|---|---|---|
| | Complete allotype | 214 | (allo-type) | 356/358 | (allo-type) | 431 | (allo-type) |
| Rituximab | G1m17,1 | K | 17 | D/L | 1 | A | — |
| Veltuzumab | G1m3 | R | 3 | E/M | — | A | — |

In order to reduce the immunogenicity of therapeutic antibodies in individuals of nG1m1 genotype, it is desirable to select the allotype of the antibody to correspond to the EEM allotype, with a glutamate residue at Kabat position 356, a methionine at Kabat position 358, and preferably an arginine residue at Kabat position 214. Surprisingly, it was found that repeated subcutaneous administration of G1m3 antibodies over a long period of time did not result in a significant immune response.

Bi-Specific Antibodies

In certain embodiments, the anti-HLA-DR antibodies disclosed herein may be used in combination with another molecule attached to the antibody. Attachment may be either covalent or non-covalent. In some embodiments, an anti-HLA-DR antibody may be used in a bi-specific antibody, i.e., an antibody that has two different binding sites, one for HLA-DR antibody and another for a different target antigen, such as a hapten or a disease-associated antigen. Methods for construction and use of bi-specific and multi-specific antibodies are disclosed, for example, in U.S. Pat. Nos. 6,962,702; 7,074,405; 7,230,084; 7,300,644; 7,429,381 and 7,563,439, the Examples section of each of which is incorporated herein by reference.

Where the bi-specific antibody is targeted in part against a tumor-associated antigen, exemplary types of tumors that may be targeted include acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid, non-Hodgkin's lymphoma, ovarian cancer, pancreatic cancer, glioma, melanoma, liver cancer, prostate cancer, and urinary bladder cancer Preferred are tumors that have constitutive expression of HLA-DR.

Pre-Targeting

One strategy for use of bi-specific antibodies includes pretargeting methodologies, in which therapeutic agent attached to a targetable construct is administered to a subject after a bi-specific antibody has been administered. Pretargeting methods have been developed to increase the target:background ratios of detection or therapeutic agents Examples of pre-targeting and biotin/avidin approaches are described, for example, in Goodwin et al, U.S. Pat. No. 4,863,713; Goodwin et al, J Nucl Med 29:226, 1988; Hnatowich et al, J Nucl Med 28:1294, 1987; Oehr et al, J Nucl Med 29:728, 1988; Klibanov et al, J Nucl Med 29:1951, 1988; Sinitsyn et al, J Nucl Med 3:66, 1989; Kalofonos et al, J Nucl Med 31:1791, 199; Schechter et al, Int J Cancer 48:167, 1991; Paganelli et al, Cancer Res 51:596, 1991; Paganelli et al, Nucl Med Commun 12:211, 1991; U.S. Pat. No. 5,256,395; Stickney et al, Cancer Res 51:665, 1991; Yuan et al, Cancer Res 51:3119, 1991; U.S. Pat. No. 6,77,499; U.S. Pat. No. 6,472,511; the Examples section of each of which is incorporated herein by reference.

In certain embodiments, bispecific antibodies and targetable constructs may be of use in treating and/or imaging normal or diseased tissue and organs, for example using the methods described in U.S. Pat. Nos. 6,126,916; 5,772,981; 5,746,996; 5,328,679; and 5,128,119, each incorporated herein by reference.

Immunoconjugates

In certain embodiments, the anti-HLA-DR antibody or fragment may be conjugated to one or more therapeutic or diagnostic agents. The therapeutic agents do not need to be the same but can be different, e.g. a drug and a radioisotope. For example, $^{131}$I can be incorporated into a tyrosine of an antibody or fusion protein and a drug attached to an epsilon amino group of a lysine residue. Therapeutic and diagnostic agents also can be attached, for example to reduced SH groups and/or to carbohydrate side chains. Many methods for making covalent or non-covalent conjugates of therapeutic or diagnostic agents with antibodies or fusion proteins are known in the art and any such known method may be utilized.

A therapeutic or diagnostic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent.

Methods for conjugating peptides to antibody components via an antibody carbohydrate moiety are well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, incorporated herein in their entirety by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antibody fragment. However, it is possible to introduce a carbohydrate moiety into the light chain variable region of a full length antibody or antibody fragment. See, for example, Leung et al., J. Immunol. 154: 5919 (1995); Hansen et al., U.S. Pat. No. 5,443,953 (1995), Leung et al., U.S. Pat. No. 6,254,868, incorporated herein by reference in their entirety. The engineered carbohydrate moiety is used to attach the therapeutic or diagnostic agent.

In some embodiments, a chelating agent may be attached to an antibody, antibody fragment or fusion protein and used to chelate a therapeutic or diagnostic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins are well known in the art (see, e.g., U.S. patent application Ser. No. 12/112,289, incorporated herein by reference in its entirety).

In certain embodiments, radioactive metals or paramagnetic ions may be attached to proteins or peptides by reaction with a reagent having a long tail, to which may be attached a multiplicity of chelating groups for binding ions. Such a tail can be a polymer such as a polylysine, polysaccharide, or other derivatized or derivatizable chains having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

Chelates may be directly linked to antibodies or peptides, for example as disclosed in U.S. Pat. No. 4,824,659, incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99m}$Tc, $^{94m}$Tc, $^{11}$C, $^{13}$N, $^{15}$O, $^{76}$Br, for radioimaging. The same chelates, when complexed with non-radioactive metals, such as manganese, iron and gadolinium are useful for MRI. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed.

More recently, methods of $^{18}$F-labeling of use in PET scanning techniques have been disclosed, for example by reaction of F-18 with a metal or other atom, such as aluminum. The $^{18}$F-Al conjugate may be complexed with chelating groups, such as DOTA, NOTA or NETA that are attached directly to antibodies or used to label targetable constructs in pre-targeting methods. Such F-18 labeling techniques are disclosed in U.S. patent application Ser. No. 12/112,289, filed Apr. 30, 2008, the entire text of which is incorporated herein by reference.

Therapeutic Agents

In alternative embodiments, therapeutic agents such as cytotoxic agents, anti-angiogenic agents, pro-apoptotic agents, antibiotics, hormones, hormone antagonists, chemokines, drugs, prodrugs, toxins, enzymes, Bruton kinase inhibitors, PI3K inhibitors or other agents may be used, either conjugated to the subject anti-HLA-DR antibodies or separately administered before, simultaneously with, or after the antibody. Drugs of use may possess a pharmaceutical property selected from the group consisting of antimitotic, antikinase, alkylating, antimetabolite, antibiotic, alkaloid, anti-angiogenic, pro-apoptotic agents and combinations thereof.

Exemplary drugs of use may include 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epipodophyllotoxin, estrogen receptor binding agents, etoposide (VP16), etoposide glucuronide, etoposide phosphate, floxuridine (FUdR), 3',5'-O-dioleoyl-FudR (FUdR-d0), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosurea, plicomycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine and *vinca* alkaloids.

Toxins of use may include ricin, abrin, alpha toxin, saporin, ribonuclease (RNase), e.g., onconase, DNase I, Staphylococcal enterotoxin-A, pokeweed antiviral protein, gelonin, diphtheria toxin, *Pseudomonas* exotoxin, and *Pseudomonas* endotoxin.

Chemokines of use may include RANTES, MCAF, MIP1-alpha, MIP1-Beta and IP-10.

In certain embodiments, anti-angiogenic agents, such as angiostatin, baculostatin, canstatin, maspin, anti-VEGF antibodies, anti-P1GF peptides and antibodies, anti-vascular growth factor antibodies, anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-B, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide (roquinimex), thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Immunomodulators of use may be selected from a cytokine, a stem cell growth factor, a lymphotoxin, an hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β or -γ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -ß; mullerian-inhibiting substance; mouse gonadotropin-associated peptide; inhibin; activin; vascular endothelial growth factor; integrin; thrombopoietin (TPO); nerve growth factors such as NGF-ß; platelet-growth factor; transforming growth factors (TGFs) such as TGF-α and TGF-ß; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor and LT. Radionuclides of use include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{227}$Th, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Th-227 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like. Some useful diagnostic nuclides may include $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, or $^{111}$In. In certain embodiments anti-, HLA-DR antibodies, such as hL243, may be of use in combination with therapeutic radionuclides for sensitization of tumors to radiation therapy (see, e.g., Allen et al., 2007, Cancer Res. 67:1155).

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Joni et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photoactivated dyes for achieving phototherapy. See Mew et al., J. Immunol. (1983),130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529.

Other useful therapeutic agents may comprise oligonucleotides, especially antisense oligonucleotides that preferably are directed against oncogenes and oncogene products, such as bcl-2 or p53. A preferred form of therapeutic oligonucleotide is siRNA.

Diagnostic Agents

Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$TC, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$CO, $^{72}$As, $^{75}$Br, $^{76}$Br, $^{82m}$Rb, $^{83}$Sr, or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Methods of Therapeutic Treatment

Various embodiments concern methods of treating a cancer in a subject, such as a mammal, including humans, domestic or companion pets, such as dogs and cats, comprising administering to the subject a therapeutically effective amount of an anti-HLA-DR antibody. In preferred embodiments, the anti-HLA-DR antibody is a humanized L243 antibody, as described in further detail in the Examples below. In more preferred embodiments, the anti-HLA-DR antibody is administered subcutaneously as a high concentration formulation of between about 100 mg/ml to 225 mg/ml. Use of high concentration formulations allows subcutaneous administration of low volumes of antibody, preferably between 1 to 3 ml or less.

In certain embodiments, the anti-HLA-DR antibody may be used to treat a hematologic cancer, such as indolent forms of B cell lymphomas, aggressive forms of B cell lymphomas, non-Hodgkin's lymphoma, Hodgkin's lymphoma, chronic lymphocytic leukemia, acute lymphoblastic leukemia, acute myelogenous leukemia, chronic myelogenous leukemia, hairy cell leukemia, Burkitt lymphoma, Waldenstrom's macroglobulinemia, and multiple myeloma.

In one embodiment, immunological diseases which may be treated with the subject antibodies may include, for example, joint diseases such as ankylosing spondylitis, juvenile rheumatoid arthritis, rheumatoid arthritis; neurological disease such as multiple sclerosis and myasthenia gravis; pancreatic disease such as diabetes, especially juvenile onset diabetes; gastrointestinal tract disease such as chronic active hepatitis, celiac disease, ulcerative colitis, Crohn's disease, pernicious anemia; skin diseases such as psoriasis or scleroderma; allergic diseases such as asthma and in transplantation related conditions such as graft versus host disease and allograft rejection.

The administration of anti-HLA-DR antibody can be supplemented by administering concurrently or sequentially a therapeutically effective amount of another antibody that binds to or is reactive with another antigen on the surface of the target cell. Preferred additional MAbs comprise at least one humanized, chimeric or human MAb selected from the group consisting of a MAb reactive with CD4, CD5, CD8, CD14, CD15, CD16, CD19, IGF-1R, CD20, CD21, CD22, CD23, CD25, CD30, CD32b, CD33, CD37, CD38, CD40, CD40L, CD45, CD46, CD52, CD54, CD70, CD74, CD79a, CD80, CD95, CD126, CD133, CD138, CD154, CEACAM5, CEACAM6, B7, AFP, PSMA, EGP-1, EGP-2, carbonic anhydrase IX, PAM4 antigen, MUC1, MUC2, MUC3, MUC4, MUC5, Ia, MIF, HM1.24, HLA-DR, tenascin, Flt-3, VEGFR, P1GF, ILGF, IL-6, IL-25, tenascin, TRAIL-R1, TRAIL-R2, complement factor C5, oncogene product, or a combination thereof. Various antibodies of use, such as anti-CD19, anti-CD20, and anti-CD22 antibodies, are known to those of skill in the art. See, for example, Ghetie et al., Cancer Res. 48:2610 (1988); Hekman et al., Cancer Immunol. Immunother. 32:364 (1991); Longo, Curr. Opin. Oncol. 8:353 (1996), U.S. Pat. Nos. 5,798,554; 6,187, 287; 6,306,393; 6,676,924; 7,109,304; 7,151,164; 7,230, 084; 7,230,085; 7,238,785; 7,238,786; 7,282,567; 7,300, 655; 7,312,318; and U.S. Patent Application Publ. Nos. 20080131363; 20080089838; 20070172920; 20060193865; 20060210475; 20080138333; and 20080146784, each incorporated herein by reference.

The anti-HLA-DR antibody therapy can be further supplemented with the administration, either concurrently or sequentially, of at least one therapeutic agent. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., Eur. J. Haematol. 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1.

The anti-HLA-DR antibody can be formulated according to known methods to prepare pharmaceutically useful compositions, whereby the anti-HLA-DR antibody is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The anti-HLA-DR antibody can be formulated for intravenous administration via, for example, bolus injection or continuous infusion. Preferably, anti-HLA-DR antibody is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the anti-HLA-DR antibody. Control release preparations can be prepared through the use of polymers to complex or adsorb the anti-HLA-DR antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release from such a matrix depends upon the molecular weight of the anti-HLA-DR antibody, the amount of anti-HLA-DR antibody within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The anti-HLA-DR antibody may also be administered to a mammal subcutaneously or even by other parenteral routes. Moreover, the administration may be by continuous infusion or by single or multiple boluses. Preferably, the anti-HLA-DR antibody is administered subcutaneously with relatively rapid injection of a small volume of antibody formulation (see, e.g., U.S. Pat. No. 8,658,773, incorporated herein by reference).

More generally, the dosage of an administered anti-HLA-DR antibody for humans will vary depending upon such factors as the patient's age, weight, height, sex, general medical condition and previous medical history. It may be desirable to provide the recipient with a dosage of anti-HLA-DR antibody that is in the range of from about 1 mg/kg to 25 mg/kg as a single intravenous infusion, although a lower or higher dosage also may be administered as circumstances dictate. More preferably, the dosage will be 4 to 18 mg/kg, more preferably 6 to 16 mg/kg, more preferably 8 to 12 mg/kg. A dosage of 1-20 mg/kg for a 70 kg patient, for example, is 70-1,400 mg, or 41-824 mg/m$^2$ for a 1.7-m patient. Most preferably, the dose administered to the subject is 200 mg. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy.

Alternatively, an anti-HLA-DR antibody may be administered as one dosage every 2 or 3 weeks, repeated for a total of at least 3 dosages. Or, the construct may be administered twice per week for 4-6 weeks. If the dosage is lowered to approximately 200-300 mg/m$^2$ (340 mg per dosage for a 1.7-m patient, or 4.9 mg/kg for a 70 kg patient), it may be administered once, twice or even thrice weekly for 3 or more weeks. Alternatively, the dosage schedule may be decreased, namely every 2 or 3 weeks for 2-3 months. This is particularly true for maintenance therapy, where lower dosages (e.g. 1, 2, 3, or 4 mg/kg or even lower) may be administered less frequently, for a prolonged period. It has been determined, however, that even higher doses, such as 20 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule In preferred embodiments, the anti-HLA-DR antibodys are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor). Cancers conducive to treatment methods of the present invention involves cells which express, overexpress, or abnormally express HLA-DR.

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis *punctata*, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Expression Vectors

Still other embodiments may concern DNA sequences comprising a nucleic acid encoding an anti-HLA-DR antibody or fusion protein. Fusion proteins may comprise an antibody or fragment attached to a different antibody or fragment or to a therapeutic protein or peptide, such as a cytokine.

Various embodiments relate to expression vectors comprising the coding DNA sequences. The vectors may contain sequences encoding the light and heavy chain constant regions and the hinge region of a human immunoglobulin to which may be attached chimeric, humanized or human variable region sequences. The vectors may additionally contain promoters that express the encoded protein(s) in a selected host cell, enhancers and signal or leader sequences. Vectors that are particularly useful are pdHL2 or GS. More preferably, the light and heavy chain constant regions and hinge region may be from a human EU myeloma immunoglobulin, where optionally at least one of the amino acid in the allotype positions is changed to that found in a different IgG1 allotype, and wherein optionally amino acid 253 of the heavy chain of EU based on the EU number system may be replaced with alanine. See Edelman et al., *Proc. Natl. Acad. Sci USA* 63: 78-85 (1969). In other embodiments, an IgG1 sequence may be converted to an IgG4 sequence.

The skilled artisan will realize that methods of genetically engineering expression constructs and insertion into host cells to express engineered proteins are well known in the art and a matter of routine experimentation. Host cells and methods of expression of cloned antibodies or fragments have been described, for example, in U.S. patent application Ser. No. 11/187,863, filed Jul. 25, 2005; Ser. No. 11/253,666, filed Oct. 20, 2005 and Ser. No. 11/487,215, filed Jul. 14, 2006, each incorporated herein by reference in its entirety.

Kits

Various embodiments may concern kits containing components suitable for treating or diagnosing diseased tissue in a patient. Exemplary kits may contain at least one or more anti-HLA-DR antibody as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, a therapeutic agent may be provided in the form of a prefilled syringe or autoinjection pen containing a sterile, liquid formulation or lyophilized preparation.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

DOCK AND LOCK® (DNL®) Method

In certain embodiments, the anti-HLA-DR antibodies or fragments may be incorporated into a multimeric complex, for example using a technique referred to as DOCK-AND-LOCK® (DNL®). The method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci USA. 1984; 81:6723), more than 50 AKAPs that localize to various suB cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). Interestingly, AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

DDD of Human RIIα and AD of AKAPs as Linker Modules

We have developed a platform technology to utilize the DDD of human RIIα and the AD of AKAP proteins as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chimura et al., Proc. Natl. Acad. Sci. USA. 2001; 98:8480) to ligate site-specifically.

In preferred embodiments, the anti-HLA-DR MAb DNL constructs may be based on a variation of the $a_2b$ structure, in which an IgG immunoglobulin molecule (e.g., hL243) is attached at its C-terminal end to two copies of an AD moiety. Preferably the AD moiety is attached to the C-terminal end of each light chain. Each AD moiety is capable of binding to two DDD moieties in the form of a dimer. By attaching a cytokine or other therapeutic protein or peptide to each DDD moiety, four copies of cytokine or other therapeutic moiety are conjugated to each IgG molecule.

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances. The DNL method was disclosed in U.S. Pat. Nos. 7,550,143; 7,521,056; 76,534,866; 7,527,787 and 7,666,400, the Examples section of each incorporated herein by reference.

In preferred embodiments, the effector moiety is a protein or peptide, more preferably an antibody, antibody fragment or cytokine, which can be linked to a DDD or AD unit to form a fusion protein or peptide. A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

DDD and AD Sequence Variants

In certain embodiments, the AD and DDD sequences incorporated into the anti-HLA-DR MAb DNL complex comprise the amino acid sequences of DDD1 (SEQ ID NO:1) and AD1 (SEQ ID NO:3) below. In more preferred embodiments, the AD and DDD sequences comprise the amino acid sequences of DDD2 (SEQ ID NO:2) and AD2 (SEQ ID NO:4), which are designed to promote disulfide bond formation between the DDD and AD moieties.

```
DDD1
                                          (SEQ ID NO: 1)
SHIQIPPGLTELLQGYTVEVLRQQPPDLVEFAVEYFTRLREARA

DDD2
                                          (SEQ ID NO: 2)
CGHIQIPPGLTELLQGYTVEVLRQQPPDLVEFAVEYFTRLREARA

AD1
                                          (SEQ ID NO: 3)
QIEYLAKQIVDNAIQQA

AD2
                                          (SEQ ID NO: 4)
CGQIEYLAKQIVDNAIQQAGC
```

However, in alternative embodiments sequence variants AD and/or DDD moieties may be utilized in construction of the anti-HLA-DR MAb DNL complexes. The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408, the entire text of each of which is incorporated herein by reference.)

For example, Kinderman et al. (2006) examined the crystal structure of the AD-DDD binding interaction and concluded that the human DDD sequence contained a number of conserved amino acid residues that were important in either dimer formation or AKAP binding, underlined below in SEQ ID NO:1. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding. Thus, a potential alternative DDD sequence of use for construction of DNL complexes is shown in SEQ ID NO:5, wherein "X" represents a conservative amino acid substitution. Conservative amino acid substitutions are discussed in more detail below, but could involve for example substitution of an aspartate residue for a glutamate residue, or a leucine or valine residue for an isoleucine residue, etc. Such conservative amino acid substitutions are well known in the art.

```
Human DDD sequence from protein kinase A
                                          (SEQ ID NO: 1)
SHIQIPPGLTELLQGYTVEVLRQQPPDLVEFAVEYFTRLREARA
```

```
                                                 (SEQ ID NO: 5)
XXIXIXXXLXXLLXXYXVXVLXXXXXXLVXFXVXYFXXLXXXXX
```

Alto et al. (2003) performed a bioinformatic analysis of the AD sequence of various AKAP proteins to design an RII selective AD sequence called AKAP-IS (SEQ ID NO:3), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:3. Therefore, the skilled artisan will realize that variants which may function for DNL constructs are indicated by SEQ ID NO:6, where "X" is a conservative amino acid substitution.

```
AKAP-IS sequence
                                                 (SEQ ID NO: 3)
QIEYLAKQIVDNAIQQA (SEQ ID NO: 6)
XXXXXAXXIVXXAIXXX
```

Similarly, Gold (2006) utilized crystallography and peptide screening to develop a SuperAKAP-IS sequence (SEQ ID NO:7), exhibiting a five order of magnitude higher selectivity for the RII isoform of PKA compared with the RI isoform. Underlined residues indicate the positions of amino acid substitutions, relative to the AKAP-IS sequence, that increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare anti-HLA-DR MAb DNL constructs. Other alternative sequences that might be substituted for the AKAP-IS AD sequence are shown in SEQ ID NO:8-10. Substitutions relative to the AKAP-IS sequence are underlined. It is anticipated that, as with the AKAP-IS sequence shown in SEQ ID NO:3, the AD moiety may also include the additional N-terminal residues cysteine and glycine and C-terminal residues glycine and cysteine, as shown in SEQ ID NO:4.

```
SuperAKAP-IS
                                                 (SEQ ID NO: 7)
QIEYVAKQIVDYAIHQA Alternative AKAP sequences
                                                 (SEQ ID NO: 8)
QIEYKAKQIVDHAIHQA (SEQ ID NO: 9)
QIEYHAKQIVDHAIHQA (SEQ ID NO: 10)
QIEYVAKQIVDHAIHQA
```

Stokka et al. (2006) also developed peptide competitors of AKAP binding to PKA, shown in SEQ ID NO:11-13. The peptide antagonists were designated as Ht31 (SEQ ID NO:11), RIAD (SEQ ID NO:12) and PV-38 (SEQ ID NO:13). The Ht-31 peptide exhibited a greater affinity for the RII isoform of PKA, while the RIAD and PV-38 showed higher affinity for RI.

```
Ht31
                                                 (SEQ ID NO: 11)
DLIEEAASRIVDAVIEQVKAAGAY

RIAD
                                                 (SEQ ID NO: 12)
LEQYANQLADQIIKEATE

PV-38
                                                 (SEQ ID NO: 13)
FEELAWKIAKMIWSDVFQQC
```

Hundsrucker et al. (2006) developed still other peptide competitors for AKAP binding to PKA, with a binding constant as low as 0.4 nM to the DDD of the RII form of PKA. The sequences of various AKAP antagonistic peptides is provided in Table 1 of Hundsrucker et al. (incorporated herein by reference). Residues that were highly conserved among the AD domains of different AKAP proteins are indicated below by underlining with reference to the AKAP IS sequence (SEQ ID NO:3). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence are shown in SEQ ID NO:14-16.

```
AKAP-IS
                                                 (SEQ ID NO: 3)
QIEYLAKQIVDNAIQQA

AKAP7δ-wt-pep
                                                 (SEQ ID NO: 14)
PEDAELVRLSKRLVENAVLKAVQQY AKAP7δ-L304T-pep
                                                 (SEQ ID NO: 15)
PEDAELVRTSKRLVENAVLKAVQQY AKAP7δ-L308D-pep
                                                 (SEQ ID NO: 16)
PEDAELVRLSKRDVENAVLKAVQQY
```

Carr et al. (2001) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIa DDD sequence of SEQ ID NO:1. Residues that were particularly conserved are further indicated by italics. The residues overlap with, but are not identical to those suggested by Kinderman et al. (2006) to be important for binding to AKAP proteins. Thus, a potential DDD sequence is indicated in SEQ ID NO:17, wherein "X" represents a conservative amino acid substitution.

```
                                                 (SEQ ID NO: 1)
SHIQIPPGLTELLQGYTVEVLRQQPPDLVEFAVEYFTRLREARA (SEQ ID NO: 17)
XHIXIPXGLXELLQGYTXEVLRXQPXDLVEFAXXYFXXLXEXRX
```

The skilled artisan will realize that in general, those amino acid residues that are highly conserved in the DDD and AD sequences from different proteins are ones that it may be preferred to remain constant in making amino acid substitutions, while residues that are less highly conserved may be more easily varied to produce sequence variants of the AD and/or DDD sequences described herein.

In addition to sequence variants of the DDD and/or AD moieties, in certain embodiments it may be preferred to introduce sequence variations in the antibody moiety or the linker peptide sequence joining the antibody with the AD sequence. In one illustrative example, three possible variants of fusion protein sequences, are shown in SEQ ID NO:18-20.

```
(L)
                                    (SEQ ID NO: 18)
QKSLSLSPGLGSGGGGSGGCG (A)
                                    (SEQ ID NO: 19)
QKSLSLSPGAGSGGGGSGGCG (-)
                                    (SEQ ID NO: 20)
QKSLSLSPGGSGGGGSGGCG
```

Amino Acid Substitutions

In certain embodiments, the disclosed methods and compositions may involve production and use of proteins or peptides with one or more substituted amino acid residues. As discussed above, methods for making monoclonal antibodies against virtually any target antigen are well known in the art. Typically, these result in production of murine antibodies against a target antigen. As is well known in the art, the antigen-binding specificity of murine monoclonal antibodies is determined largely by the hypervariable complementarity determining region (CDR) sequences. Murine antibodies generally comprise 6 CDR sequences, 3 on the antibody light chain and 3 on the heavy chain. As described in detail above, chimeric, humanized or human versions of murine antibodies may be constructed by techniques such as CDR grafting, where the murine CDR sequences are inserted into, for example, human antibody framework and constant region sequences, or by attaching the entire murine variable region sequences to human antibody constant region sequences. In alternative embodiments, the variable region sequences of an antibody may be constructed, for example, by chemical synthesis and assembly of oligonucleotides encoding the entire light and heavy chain variable regions of an antibody.

In various embodiments, the structural, physical and/or therapeutic characteristics of native, chimeric, humanized or human antibodies, or AD or DDD sequences may be optimized by replacing one or more amino acid residues. For example, it is well known in the art that the functional characteristics of humanized antibodies may be improved by substituting a limited number of human framework region (FR) amino acids with the corresponding FR amino acids of the parent murine antibody. This is particularly true when the framework region amino acid residues are in close proximity to the CDR residues.

In other cases, the therapeutic properties of an antibody, such as binding affinity for the target antigen, the dissociation- or off-rate of the antibody from its target antigen, or even the effectiveness of induction of CDC (complement-dependent cytotoxicity) or ADCC (antibody dependent cellular cytotoxicity) by the antibody, may be optimized by a limited number of amino acid substitutions.

In alternative embodiments, the DDD and/or AD sequences used to make the anti-HLA-DR DNL constructs may be further optimized, for example to increase the DDD-AD binding affinity. Potential sequence variations in DDD or AD sequences are discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

EXAMPLES

Example 1. Phase I Trial of Subcutaneous hL243 Administration in Patients with B-Cell NHL or CLL In preclinical studies, a novel anti-HLA-DR IgG4 antibody, hL243 (IMMU-114), was consistently more cytotoxic than rituximab (anti-CD20) in the cell lines studied, with minimal CDC and ADCC, but activating internal signaling and inducing apoptosis via the AKT survival pathway (Stein et al, 2006, *Blood* 108:2736-44; Stein et al., 2010, *Blood* 115:5180-90). In vitro studies demonstrated significant growth inhibition of B-cell lymphoma cell lines, including a rituximab-resistant cell line. In vivo canine lymphoma safety studies were performed (Stein et al, 2011, *Leuk Lymphoma* 52:273-84). A monkey toxicology study found toxicities with once weekly SQ injections×4 were limited to mild redness and itching at the injection site.

The present Example represents a Phase I first-in-man study of IMMU-114, to evaluate subcutaneous (SQ) IMMU-114 injection in patients with recurrent/relapsed B-cell NHL or CLL. Table 2 shows the demographics of the treated patient population. Eligible patients had recurrent/relapsed NHL/CLL with at least one prior therapy, ECOG performance status <3, normal baseline renal and liver function, with platelets ≥50,000/mm$^3$ and ANC ≥1000/mm$^3$.

TABLE 2

| Patient Demographics for Phase I Clinical Trial of SQ anti-HLA-DR | |
|---|---|
| Male/Female | 11/6 |
| Age, median (range) | 72 (46-80) |
| ECOG: 0, 1, 2 | 4/9/4 |
| Histology | |
| DLBCL | 7 |
| FL | 5 |
| MZL | 2 |
| CLL | 2 |
| SLL | 1 |
| Prior treatments, median (range) | 2 (1-7) |
| Rituximab/anti-CD20 containing | 17 |
| Bendamustine containing | 11 |
| CHOP-based | 8 |
| Other* | ≤3 |

*R-CVP (n = 3), RICE (n = 3), Ibrutinib (n = 3), SCT + myeloablative chemotherapy (n = 2), other agents/regimens (n = 1, each)

Cohorts of 3-6 patients received 200 mg IMMU-114 administered once-, twice-, or thrice-weekly for the first 3 weeks of a 4-week cycle. All patients received 2 consecutive treatment cycles, followed 4 weeks later by elective maintenance therapy (one week of treatment every 4 weeks×4). NCI-CTCAE v. 4.0 was used to grade adverse events (AEs). Dose-limiting toxicity was defined as including: Grade 4 (or Grade 3>7 days) hematologic toxicity, excluding lymphopenia; Grade 4 (or Grade 3 requiring hospitalization/dialysis) injection reaction, infection or tumor lysis syndrome; Grade 4 fatigue ≥7 days; other Grade 3 or 4 toxicity (excluding nausea/vomiting, electrolyte abnormalities w/o clinical sequelae, or liver function abnormality resolved to Grade 1 within 3 days of maximal antiemetic/electrolyte replacement therapy); or toxicity of any Grade causing treatment delays >14 days. Treatment response was assessed 4 weeks after cycle 2, then every 3 months until progression, using 2007 IWG-NHL or 2008 IW-CLL criteria.

Results—

Eleven patients (46-80 years old) with 2 median prior treatments (range, 1-5; all had received rituximab) have now been treated at dose level (DL) 1 (200 mg weekly, n=3), 2 (400 mg weekly, n=5), and 3 (600 mg weekly, n=3). They had diffuse large B-cell lymphoma (DLBCL, n=5); follicular lymphoma (FL, n=3); CLL (n=1), small lymphocytic lymphoma (SLL, n=1), or marginal zone lymphoma (MZL, n=1). Administration reactions were limited and all were Grade 1-2 events, predominantly injection site erythema. No serious adverse events (SAEs) occurred at DL1 or DL2. At DL3, one DLBCL patient with unrelated anorexia/hypovolemia withdrew prior to cycle 2 with acute renal failure and fatal gastrointestinal bleeding, and one MZL patient developed fatal septic shock after completing cycle 2.

Safety laboratories were unremarkable and there has been no evidence of human anti-IMMU-114 antibodies in 5 patients currently evaluated. Circulating leukemic cells in the single CLL patient decreased with each cycle, but normal B-cell changes in the NHL patients were modest. At DL1, 2 DLBCL patients progressed after cycle 2, but one FL patient achieved an unconfirmed partial response (PR; 47% tumor shrinkage, progressing 3 months later after completing maintenance treatment). At DL 2, one DLBCL patient with unrelated pneumonia withdrew after one dose, one DLBCL patient had a PR (60% shrinkage) with a confirmatory scan pending, one FL patient progressed after cycle 2, one FL patient achieved a PR (83% shrinkage continuing now 10 months later), and one CLL patient had an unconfirmed PR during cycle 1 (WBC<50% baseline, progressing after 2 months). At DL3, one patient with SLL progressed after cycle 2 and the other 2 patients with SAEs were not assessed for treatment response.

A representative example of solid tumor reduction is shown in FIG. 29. Patient 181-001 had extensive abdominopelvic lymphadenopathy, including target lesions shown above (arrows). Comparison of post-treatment CT images (POST) with baseline CT images (PRE) shows reduction in target lesions 4 weeks after completing 2 cycles of treatment at dose level 1 (200 mg once-weekly).

Antibody serum levels were evaluated on injection days by ELISA. For dose level 1 (once-weekly), IMMU-114 levels were not detectable (<24 ng/ml). For dose levels 2 and 3, IMMU-114 levels on the last weekl injection day increased on treatment weeks 1, 2 and 3 of cycles 1 and 2, with peak concentrations of about 40 to 50 ng/ml seen at week 3 with both dose levels.

Table 3 summarizes the results from five patients with objective evidence of treatment activity. Activity was seen in five of ten evaluable patients (50%), including one complete response (10%). The best response by subgroup is shown in Table 4.

TABLE 3

Treatment Activity in Evaluable Patients

| Patient | Best Response | Duration/Outcome |
|---|---|---|
| 181-001 (FL, DL1) | SD (48% tumor reduction after cycle 2) | Progression after maintenance (5.3 months from 1$^{st}$ dose) |
| 212-002 (FL, DL2) | CR (initial 83% tumor shrinkage after cycle 2; improvement after maintenance with eventual complete response) | Response ongoing 1.4 years after 1$^{st}$ dose |
| 258-001 (DLBCL, DL2) | PR (60% tumor shrinkage after cycle 2) | Currently receiving maintenance with next evaluation pending |
| 181-005 (CLL, DL2) | PR$_{BL}$* (WBC 87% decreased from 102,300 to 12,900 at end of cycle 2) | Progression 4 weeks after cycle 2 |
| 181-008 (CLL, DL2) | PR$_{BL}$* (WBC 59% decreased from 22,100 to 9,000 at end of cycle 2) | Progression 4 weeks after cycle 2 |

*PR$_{BL}$ = ≥50% decrease in peripheral blood leukocytosis in CLL patients. Changes in other PR response criteria were not assessed until after treatment.

TABLE 4

Best Response by Subgroup

| Response by Subgroups | Patients | Best Response | | | |
|---|---|---|---|---|---|
| | | CR | PR/PR$_{BL}$ | SD | PD |
| Overall Histology | 10 | 1 | 3 | 1 | 5 |
| DLBCL | 4 | — | 1 | — | 3 |
| FL | 3 | 1 | — | 1 | 1 |
| CLL/SLL | 3 | — | 2 | — | 1 |
| Dose Level | | | | | |
| DL1: 200 mg once-weekly | 3 | — | — | 1 | 2 |
| DL2: 200 mg twice-weekly | 6 | 1 | 3 | — | 2 |
| DL3: 200 mg thrice-weekly | 1 | — | — | — | 1 |

*Results based on 10 patients currently assessable for treatment response. Excludes 2 patients currently being treated (too early for response assessment) and 5 patients withdrawn without assessment either prior to treatment (neutropenic fever), during treatment cycle 1 (pneumonia, disease complication), prior to completing treatment cycle 2 (clinical deterioration), or after treatment but prior to first response assessment 4 weeks later (septic shock).

Conclusion—

SQ injections of IMMU-114 appear to avoid the significant administration reactions that have limited the development of other anti-HLA-DR antibodies given IV. With lack of toxicity and preliminary efficacy observed at the two lowest dose levels, DL 2 was selected as for subsequent expansion cohorts. While IMMU-114 demonstrated activity in this population relapsed/refractory to rituximab-containing therapies, the presence of short responses in some patients suggests treatment should be maintained beyond 2 cycles. Thus, the dosing scheme is being amended to allow treatment cycles to be repeated until disease progression, to determine an appropriate dosing schedule for undertaking a phase II study. In total, five of ten (50%) of assessable patients (FL×2, CLL×2, DLBCL) had objective evidence of treatment response, with one complete response observed. Circulating leukemic cells in CLL patients decreased with treatment, while B-cell changes in NHL patients were modest. The excellent safety profile and apparent therapeutic effect of IMMU-114 supports its use in hematologic cancers of human patients.

Example 2. Construction of a Humanized L243 Antibody

Molecular Cloning of L243V$_K$ and V$_H$ Genes

The hybridoma cell clone producing the mAb mL243 (ATCC HB55) was cultured in HSFM medium (Life Technologies, Inc) supplemented with 10% FBS (Hyclone). The genes encoding the VK (VK1BACK/CK3') and VH (VH1BACK/VH1FOR) of mL243 were cloned by RT-PCR and the sequences were determined by DNA sequencing. Multiple independent clones were sequenced to eliminate possible errors resulting from the PCR reaction.

Sequence Design of hL243 V Genes

Searching the human V$_K$ and V$_H$ sequences in the Kabat database, the FRs of mL243 V$_K$ and V$_H$ were found to exhibit the highest degree of sequence homology to human REI V$_K$ and RF-TS3 V$_H$, respectively. One exception is the FR4 of mL243 V$_H$, which showed the highest sequence homology with that of NEWM V$_H$. Therefore, the human REI framework sequences were used as the scaffold for grafting the CDRs of mL243VK, and a combination of RF-TS3 and NEWM framework sequences were used for hL243 V$_H$. There are a number of amino acid changes in each chain outside of the CDR regions when compared to the starting human antibody frameworks. Several amino acid residues in murine FRs that flank the putative CDRs were maintained in the reshaped hL243 Fv based on the guideline previously established (Qu et al, Clin Cancer Res (1999) 5 3095s-3100s). These residues are R37, K39, V48, F49, and G100 of mL243V$_k$ and F27, K38, K46, A68, and F91 of mL243V$_H$ (FIG. 3 and FIG. 4 respectively). Also see SEQ ID NO:3 and SEQ ID NO:4 respectively for the sequences of hL243 V$_L$ and hL243 V$_H$ respectively.

Construction of hL243 V Sequences

A modified strategy as described by Leung et al. (Mol Immunol (1995) 32:1413-1427) was used to construct the designed V$_K$ and V$_H$ genes for hL243, using a combination of long oligonucleotide syntheses and PCR. For the construction of the hL243 V$_H$ domain, two long oligonucleotides, hL243VHA (175-mer) and hL243VHB (168-mer) were synthesized on an automated DNA synthesizer (Applied Biosystem).

hL243VHA represents nt 23 to 197 of the HL243VH domain (SEQ ID NO: 21)
GGTCTGAGTTGAAGAAGCCTGGGGCCTCAGTGAAGGTTTCCTGCAAGGCT

TCTGGATTTACCTTCACAAACTATGGAATGAACTGGGTGAAGCAGGCCCC

TGGACAAGGGCTTAAGTGGATGGGCTGGATAAACACCTACACTAGAGAGC

CAA<u>CATATGCTGATGACTTCAAGGG</u> hL243VHB represents the minus strand of the hL243VH domain complementary to nt 176 to 343.

(SEQ ID NO: 22)
ACCCTTGGCCCCAGTAGTCAAAACCCGTAGGTACAACCGCAGTAATATCT

CTTGCACAGAAATACACGGCAGTGTCGTCAGCCTTTAGGCTGCTGATCTG

GAGATATGCCGTGCTGACAGAGGTGTCCAAGGAGAAGGCAAACCGT<u>CCCT</u>

<u>TGAAGTCATCAGCATATG</u>

The 3'-terminal sequences (22 nt residues) of hL243VHA and B are complementary to each other, as underlined in the above sequences. The 3'-ends of hL243VHA and B anneal to form a short double stranded DNA flanked by the rest of the long oligonucleotides. Each annealed end serves as a primer for the replication of the single stranded DNA in a PCR reaction, resulting in a double strand DNA composed of the nt 23 to 343 of hL243VH. This DNA was further amplified in the presence of a short oligonucleotide primer pair, hRS7VHBACK and hL243VHFOR, to form the full-length hL243VH. Because of the sequence identity between hRS7VH and hL243VH in this region, hRS7VHBACK, previously designed and used for hRS7 Ab, was used here.

hRS7VHBACK
(SEQ ID NO: 23)
GTGGTGCTGCAGCAATCTGGGTCTGAGTTGAAGAAGCC hL243VHFOR
(SEQ ID NO: 24)
TGAGGAGACGGTGACCAGGGACCCTTGGCCCCAGTAGT

A minimum amount of hL243VHA and B (determined empirically) was amplified in the presence of 10 µl of 10×PCR Buffer (500 mM KCl, 100 mM TrisHCL buffer, pH 8.3, 15 mM MgCl$_2$), 2 µmol of hRS7VHBACK and hL243VHFOR, and 2.5 units of Taq DNA polymerase (Perkin Elmer Cetus, Norwalk, Conn.). This reaction mixture was subjected to 3 cycle of PCR reaction consisting of denaturation at 94° C. for 1 minute, annealing at 45° C. for 1 minute, and polymerization at 72° C. for 15 minutes, and followed by 27 cycles of PCR reaction consisting of denaturation at 94° C. for 1 minute, annealing at 55° C. for 1 minute, and polymerization at 72° C. for 1 minute. Double-stranded PCR-amplified product for hL243VH was gel-purified, restriction-digested with PstI and BstEII and cloned into the complementary PstI/BstEII sites of the heavy chain staging vector, VHpBS4.

For constructing the full length DNA of the humanized V$_K$ sequence, hL243 VKA (155-mer) and hL243VKB (155-mer) were synthesized as described above. hL243VKA and B were amplified by two short oligonucleotides hImmu31VKBACK and hImmu31VKFOR as described above. hImmuS 1 VKB ACK and hImmuSl VKFOR were designed and used previously for a humanized anti-AFP Ab (Qu et al, Clin Cancer Res (1999) 5 395-31).

hL243VKA represents nt 21 to 175 of the hL243VD domain (SEQ ID NO: 25)
TCCATCATCTCTGAGCGCATCTGTTGGAGATAGGGTCACTATCACTTGTC

GAGCAAGTGAGAATATTTACAGTAATTTAGCATGGTATCGTCAGAAACCA

GGGAAAGCACCTAAACTGCTGGTCTTTGCTGCATCAAACTTAGCAGATGG

TGTGC hL243VKB represents the minus strand of the hL243VK domain complementary to nt 154 to 312

(SEQ ID NO: 26)
CAGCTTGGTCCCTCCACCGAACGCCCACGGAGTAGTCCAAAAATGTTGAC

AATAATATGTTGCAATGTCTTCTGGTTGAAGAGAGCTGATGGTGAAAGTA

TAATCTGTCCCAGATCCGCTGCCAGAGAATCGCGAAGGCACACCATCTGC

TAAGTTTGA hImmu31VKBACK
(SEQ ID NO: 27)
GACATTCAGCTGACCCAGTCTCCATCATCTCTGAGCGC hImmu31VKFOR
(SEQ ID NO: 28)
CCGGCAGATCTGCAGCTTGGTCCCTCCACCG Gel-purified PCR products for hL243VK were restriction-digested with PvuII and BglHI and cloned into the complementary PvuI/BclI sites of the light chain staging vector, VKpBR2. The final expression vector hL243pdHL2 was constructed by sequentially subcloning the Xbal-BamHI and XhoI/NotI fragments of hL243V$_K$ and V$_H$, respectively, into pdHL2 as described above.

Construction of the Expression Vectors for hL243 Antibodies

A final expression vector hL243pdHL2 was constructed by sequentially subcloning the Xbal-BamHI and XhoI/NotI fragments of hL243V$_K$ and V$_H$, respectively, into pdHL2 as described previously (Losman et al Cancer, 80:266, 1997). The expression vector pdHL2, as described by Gilles et al (J Immunol Methods 125:191, 1989), contains the genomic sequence of the human γ1 chain, therefore, the hL243 is an IgG1/K isotype.

To construct the expression vector for hL243 of other isotypes, such as IgG4/K, the genomic sequence of human γ1 chain was replaced with that of γ4 chain, which was obtained by PCR amplification. The template used was the genomic DNA extracted from ATCC CRL-11397 cell and the primer pair was P-SacII CCGCGGTCACATGGCAC-CACCTCTCTTGCAGCTTCCACCAAGGGCCC (SEQ ID NO:29) and P-EagI CCGGCCGTCGCACTCATT-TACCCAGAGACAGGG (SEQ ID NO:30). The amplified PCR product was cloned into TOPO-TA sequencing vector (Invitrogen) and the sequence was confirmed by DNA sequencing.

A point mutation, Ser241Pro (based on Kabat numbering) was introduced into the hinge region of the γ4 sequence to avoid formation of half-molecules when the IgG4 Ab is expressed in mammalian cell cultures (Schuurman et al, Mot Immunol 38:1, 2001). The human γ4 hinge region sequence between PstI and StuI restriction sites (56 bp) was replaced with a synthetic DNA fragment with substitution of the TCA codon for Ser241 to CCG for Pro. The human γ1 genomic sequence in hL243pdHL2 was substituted with the mutated γ4 sequence, resulting in the final expression vector, designated as hL243γ4PpdHL2, for the IgG4 isotype hL243.

Transfection and Expression of hL243 Antibodies

Approximately 30 µg of the expression vector for hL243 or hL243γ4P was linearized by digestion with SalI and transfected into Sp2/0-Ag14 cells by electroporation (450V and 25 g). The transfected cells were plated into 96-well plates for 2 days and then selected for drug-resistance by adding MTX into the medium at a final concentration of 25 pM. MTX-resistant colonies emerged in the wells after 2-3 weeks. Supernatants from colonies surviving selection were screened for human Ab secretion by ELISA assay. Briefly, 100 ul supernatants were added into the wells of a microtiter plate precoated with GAH-IgG, F(ab')$_2$ fragment-specific Ab and incubated for 1 h at room temperature. Unbound proteins were removed by washing three times with wash buffer (PBS containing 5% polysorbate 2). HRP-conjugated GAH-IgG, Fc fragment-specific Ab was added to the wells. Following an incubation of 1 h, the plate was washed. The bound HRP-conjugated Ab was revealed by reading $A_{490}$ nm after the addition of a substrate solution containing 4 mM OPD and 0.04% $H_2O_2$. Positive cell clones were expanded and hL243 and hL243γ4P were purified from cell culture supernatant by affinity chromatography on a Protein A column.

The Ag-Binding Specificity of hL243

Figure 5:
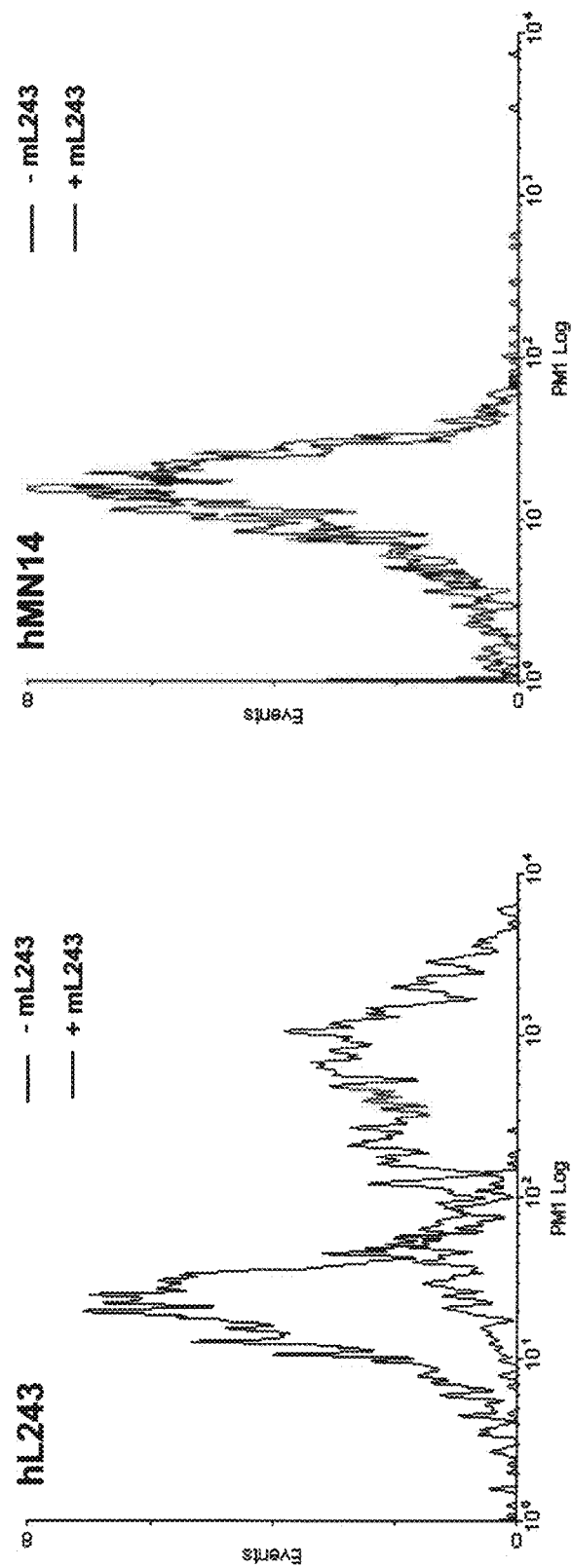
FIG. 5 illustrates an exemplary antigen-binding specificity of hL243. Raji cells, preincubated with a saturating concentration of mL234 (for blocking cell surface antigen ("Ag") sites) or without, were resuspended in PBS containing 1% BSA and 10 µg/ml of purified hL243 and incubated for 1 h at 4° C. After washing, the cells were resuspended in PBS containing 1% BSA and PE-labeled goat anti-human IgG, Fc fragment specific antibody. After further incubation at 4° C. for 30 min, the cells were counted in a Guava PCA. The left side of the Figure shows specific binding of hL243 to Raji human lymphoma cells, which was blocked by preincubation of the cells with mL243. The right side of the Figure shows a negative binding control, performed with anti-CEA antibody (hMN-14) in place of hL243 under identical conditions.

Ag-binding activity and specificity of HL243 was shown by a cell surface binding assay. Raji cells were incubated in PBS/BSA (1%) containing saturate concentration of purified hL243 (2 µg/ml) for 1 h at 4° C. After washing, cell surface-bound hL243 was detected by incubating the Raji cells in the buffer containing a PE-conjugated $2^{nd}$ antibody (goat anti-human IgG, Fc fragment specific) and counting in a Guave PCA system (Guava Technologies, Inc, Hayword, Calif.). As shown in FIG. 5, hL243 bound to an antigen on Raji cells recognized by mL243 because the binding is specifically blocked by preincubation of the cells with mL243, indicating the Ag-binding specificity of mL243 is preserved in the humanized version.

The Ag-Binding Activity of hL243γ4P

A competition cell-binding assay was carried out to assess the immunoreactivity of hL243γ4P relative to the parent mL243. A constant amount of $^{125}$I-labeled murine L243 or hL243γ4P (100,000 cpm, ~10 µCi/m) was incubated with human lymphoma cells (Raji, Daudi or Ramos) in the presence of varying concentrations (0.2-700 nM) of purified hL243γ4P or murine L243 at 4° C. for 1-2 h. Unbound Abs were removed by washing the cells in PBS. The radioactivity associated with cells was determined after washing. As shown in FIG. 6, murine L243 and hL243γ4P mAbs competed with each other for the binding to the cell surface antigen, indicating they recognize same antigenic determinant. hL243γ4P showed an apparent ~2-fold stronger binding avidity than mL243 because it competed better than mL243 ($EC_{50}$ of ~7 vs ~16.5 nM).

The antigen-binding affinity constant of hL243γ4P was determined by direct cell surface binding assay of the radiolabeled antibodies and Scatchard plot analysis. To measure specific cell surface antigen binding, two sets of cells were prepared and used in the binding assay to estimate the non-specific and total binding of radioactivities, respectively. The cells for non-specific binding were pre-incubated with excess amount of unlabled Ab to block all surface antigen sites prior to adding the radiolabeled antibody, while those for total binding were pre-incubated in PBS. After pre-incubation, varying amounts of either $^{125}$I-hL243γ4P or $^{125}$I-mL243 were added and incubated with $2 \times 10^5$ human lymphoma cells (Raji, Daudi or Ramos) at 4° C. for 2 h and unbound antibodies were removed by washing. The cell-associated radioactivity was counted. The specific cell surface binding of the radiolabeled antibody at a given concentration of radiolabeled antibody was calculated as: the counts of total binding minus the counts of non-specific binding. Scatchard plot analysis was then performed to determine the maximum number of hL243γ4P and mL243 binding sites per cell and the apparent dissociation constants of the equilibrium binding. As shown in FIG. 7, the maximum binding of hL243γ4P and mL243 to Daudi cells was virtually same, $\sim 6 \times 10^5$ molecules/cell, indicating they bound to the same Ag. The apparent dissociation constant values for hL243γ4P and mL243 were calculated to be 2.6 and 14 nM, respectively. Similar results were obtained with Raji and Ramos cells (data not shown).

Example 3. hL243γ4P Functional Studies

In vitro cell-based studies were conducted to determine whether hL243γ4P had retained its antiproliferative effect and whether effector cell and complement binding functions have been abrogated. This study indicated that the antiproliferative effect had been maintained, while effector cell and complement binding functions had been abrogated.

Effector Cell Assay

The goal of replacing the Fc region of hL243 with an IgG4 isotype Fc region was to abrogate effector cell functions through Fcγ-receptor. Complement-binding CDC and ADCC assays were performed to assess these functions by hL243γ4P.

CDC

Daudi cells were incubated with serial dilutions of the antibodies hL243, hL243γ4P, hA20 (as another positive control) and hMN14 (negative control) in the presence of human complement for 2 h. This was followed by the addition of resazurin to assess cell viability. Both untreated and maximum lysis controls were included. Fluorescence readings were obtained 5 hours after resazurin addition. The fluorescence level obtained is directly correlated to the amount of viable cells. Percent viable cells was calculated by the formula (Test—maximum lysis)/(untreated control–maximum lysis)×100. The results indicated that hL243γ4P does not produce any complement-mediated cytotoxic effect on cells compared to hL243 ($EC_5$=2.6 nM) and hA2 ($EC_5$=0.66 nM). See FIG. 8 and FIG. 15.

ADCC

Daudi cells were incubated with hA20, hL243, hL243γ4P and hMN-14 at 5 µg/ml. Effector cells were added at a ratio of 5:1. After 4 hours cell lysis was assayed by LDH release (FIG. 9A) and cell lysis (FIG. 9B).

In these results where the effects of antibody alone on effector cells are shown it can be seen that the hL243 induced significant lysis of effector cells while hL243γ4P did not. When the specific lysis figures are corrected for the effect on effector cells, hL243γ4P shows much reduced lysis of target cells compared to hL243 (12% vs 48%).

In Vitro Proliferation Assays

A multiplex colorimetric assays utilizing both MTS bioreduction (for determination of the number of viable cells) and BrdU (for quantification of cell proliferation based on the measurement of BrdU incorporation during DNA synthesis) were performed. Daudi and Raji cells were incubated with serial dilutions of hL243γ4P for 2 and 3 days. mL243 and hMN-14 were used as positive and negative controls respectively. After incubation, BrdU and MTS assays were performed. Results of the MTS assays are shown in FIG. 10 and FIG. 11. BRDU assays gave similar results (not shown). These results indicate hL243γ4P inhibits proliferation of Raji and Daudi cell lines. However in similar experiments in the EBV negative cell line Ramos, inhibition of proliferation was only observed in the presence of a crosslinking anti Fc (Fab)$_2$.

Example 4. Comparison of In Vivo Efficacy of hL243γ4P and mL243 (IgG2a) in a Xenograft Model of Human Non-Hodgkin's Lymphoma A therapeutic study was performed to compare the in vivo efficacy of humanized L243-IgG4 and murine L243-IgG2a monoclonal antibody isotypes, in a xenograft model of human non-Hodgkin's lymphoma (Raji). Prior in vitro studies have shown that replacing the Fc region of L243-IgG1 with an IgG4 isotype abrogates the effector cell functions of the antibody (ADCC and CDC), while retaining the anti-proliferative effects. Prior studies using fully human anti-HLA-DR antibodies engineered as an IgG4 isotype have also been shown to minimize side effects due to Fcγ-mediated effector functions while providing excellent tumoricidal activity in vitro, and in vivo in xenograft models of non-Hodgkins lymphoma and animal models (cynomologus monkeys) with no long-lasting hematological effects. See Nagy et al, Nature Medicine, 8:801 (2002). Thus, this study aimed to determine if hL243-IgG4 could maintain significant antitumor efficacy in a xenograft model. In the absence of sufficient quantity of hL243-IgG1, mL243 IgG2a was used (murine IgG2a is the equivalent of human IgG1 in complement fixation, and effecting ADCC).

SCID mice were injected with 2.5 million Raji cells. Therapy with hL243-IgG4 or mL243-IgG2a was initiated 1 day post tumor cell administration. Both groups of mice injected with saline or with non-specific control antibody, hMN-14, had a median survival time (MST) of 17 days. All the groups of mice treated with either humanized or murine L243 had significantly improved life span compared to mice injected with saline or hMN-14 (P<0.0001). Treatment with various doses of hL243 IgG4 resulted in a dose-response relationship, with mice receiving higher doses having better survival times. In the group of animals treated with various doses of mL243 IgG2a, the cure rate was in the range of 80-100%. See FIG. 12.

This study showed the concurrent retention of antitumor efficacy and removal of complement binding activity of the IgG4 construct of L243. Significant therapeutic benefits using the aforementioned constructs may be achieved in patients for the treatment of autoimmune diseases, lymphomas, and leukemias, as well as immune dysregulatory, metabolic, and neurodegenerative diseases involving HLA-DR expression.

Example 5. In Vitro Comparison of hL243 with L243 and Anti-B Cell MAbs in the Treatment of Human and Canine Lymphomas A 0.5 mg sample of hL243 (IgG4 isotype) was tested for reactivity with lymphoma cell lines and a dog B cell lymphoma aspirate in comparison to the murine L243 as well as in comparison to other anti-B cell MAbs. Two functional studies were also done. The ability of the hL243 to induce apoptosis in the dog lymphoma aspirate was determined, and the anti-proliferative activity of the hL243 was tested against Namalwa, a human lymphoma cell line reported to be resistant to rituximab.

The binding of humanized or chimeric MAbs on human B cell lymphomas were measured by flow cytometry using a Fluorescence-Activated Cell Sorter (FACS) in which the following MAbs-hMN-14, hLL1, hLL2, hA20, RITUXAN®, and hL243 were stained with FITC goat anti-human (GAH) IgG Fc. The cell lines chosen were Namalwa (a rituximab resistant human B cell lymphoma cell line), SU-DHL-6 (a human B cell non-Hodgkin's lymphoma), WSU-FSCCL (an EBV-negative low-grade human B cell lymphoma cell line), Raji, Daudi, and Ramos cells. As shown in Table 6, hL243 bound to all the aforementioned cell lines. In particular, hL243 bound to the Namalwa cells that are CD20-unresponsive, showing greater binding than other humanized MAbs. (See Table 5) Furthermore, hL243 demonstrated anti-proliferative activity in the rituximab resistant human B cell lymphoma cell line, Namalwa, as measured by a $^3$H-thymidine uptake assay. The other anti-CD20 antibody, humanized A20 (hA20), developed by Immunomedics, Inc, showed similar results to rituximab, a chimeric anti-CD20 known as RITUXAN®. See Stein et al. (2004) Clin Cancer Res 10: 2868-2878.

TABLE 5

Comparison of binding of humanized and murine MAbs on Namalwa

| Humanized MAbs | GEO MEAN Fluorescence 2nd Ab: FITC GAH | Murine MAbs | GEO MEAN Fluorescence 2nd Ab: FITC GAM |
|---|---|---|---|
| none | 2.52 | none | 2.91 |
| HMN14 | 2.49 | Ag8 | 3.64 |
| hRS7 | 2.47 | MN14 | 3.32 |
| hLL1 | 10.06 | RS7 | 3.39 |
| hLL2 | 6.76 | LL1 | 17.31 |
| hA20 | 6.28 | LL2 | 10.46 |
| Rituximab | 7.33 | 1F5 | 3.83 |
| HL243 | 324.16 | m2B8 | 6.16 |
|  |  | L243 | 594.96 |

As shown in FIG. 14A-B, the hL243 MAb yielded 28% inhibition of proliferation when given alone. This was increased to 51% when hL243 was given in combination with anti-human IgG second antibody. When used in combination with rituximab the activity was increased to a level greater than that of either MAb alone. See FIG. 14-B. Thus, anti-HLA-DR antibodies used in combination with other anti-TAA antibodies may exhibit synergistic effects against lymphoma and other diseases.

TABLE 6

Phenotyping cell lines (Binding of humanized or chimeric MAbs on B cell lines by FACS Assay)
Indirect assay using FITC-GAH Fc 2nd Ab staining Geometric Mean Fluorescence

|  | None | hMN14 | hLLl |  | hA20 | Rituximab | hL243 |
|---|---|---|---|---|---|---|---|
| Namalwa | 2.5 | 2.36 | 7.81 | 6.4 | 10.11 | 14.12 | 260.8 |
| SU-DHL-6 | 4.6 | 4.94 | 17.29 | 11 | 1199.34 | 1308.89 | 572.2 |
| WSU-FSCCL | 2.6 | 2.66 | 8.66 | 4.1 | 8.91 | 12.45 | 466.7 |
| Raji | 6.8 | 6.96 | 95.1 | 22. | 267.09 | 394.57 | 971.9 |
| Daudi | 3.1 | 3.16 | 48.77 | 51. | 240.96 | 380.45 | 937.4 |
| Ramos | 3.1 | 3.13 | 23.25 | 14. | 203.65 | 374.98 | 277.5 |

The studies also demonstrated that hL243 has a greater binding affinity to the dog lymphoma cells than other humanized MAbs. See Table 7. In addition, hL243 was able to induce apoptosis in the dog lymphoma cells when cross-linked with an anti-human IgG second antibody, measured as % cells with a sub G0/G1 phase DNA content (see FIG. 13).

TABLE 7

Phenotyping dog lymphoma aspirate

| | Murine MAbs | | | Humanized MAbs | |
|---|---|---|---|---|---|
| | % Positive | Mean FL | | % Positive | Mean FL |
| none | 3.85 | 3.37 | none | 4.48 | 3.24 |
| Ag8 | 2.81 | 3.04 | hMN-14 | 4.63 | 3.24 |
| L243 | 77.77 | 10.41 | hL243 | 26.33 | 5.47 |
| m2B8 | 2.61 | 3.11 | hA2 | 3.96 | 3.25 |
| LL1 | 6.69 | 4.01 | hLL1 | 4.71 | 3.33 |
| LL2 | 5 05 | 3 73 | hLL2 | 4 85 | 3 37 |

Example 6. hL243 Antibody Combinations and their Effects

Methods

Antibodies

The hybridoma cell clone producing the anti-HLA-DR monoclonal antibody, mL243, was obtained from ATCC (ATCC number HB-55). Cells were cultured in HSFM medium (Life Technologies, Inc) supplemented with 10% FBS (Hyclone). The genes encoding the Vκ and $V_H$ genes of L243 were cloned by RT-PCR. The humanized L243 isotype), hL243γ1, was generated similarly, as described previously (Leung et al., Hybridoma 13:469 (1994); Leung et al., Mol Immunol 32:1413 (1995); Stein et al., Blood 14:375 (2004); Govindan et al., Breast Cancer Res Treat 84:173 (2004)).

The IgG4/κ isotype of hL243, hL243γ4p, can be constructed by replacing the heavy chain constant region coding sequence for the human γ1 chain with that of γ4 chain. A point mutation, Ser241Pro (based on Kabat numbering) was introduced into the hinge region of the γ4 sequence in order to avoid formation of half-molecules when the antibody is expressed and produced in mammalian cell cultures (Schuurman et al., Mol Immunol 38:1 (2001)). Other MAbs used in the studies were rituximab, purchased from IDEC Pharmaceuticals Corp. (San Diego, Calif.), and hMN-14, or labetuzumab (humanized anti-carcinoembryonic antigen IgG1), provided by Immunomedics, Inc. The construction and characterization of hMN-14, used here as a negative isotype control, have been described previously (see, e.g., U.S. Pat. No. 5,874,540).

Cells

Exemplary cell lines were used in several studies. For example, the Burkitt lymphoma lines, Daudi, Raji, and Ramos, were purchased from the American Type Culture Collection (Manassas, Va.). Non-Burkitt lymphoma cell lines were obtained as follows: RL and SU-DHL-6, which contain the chromosomal translocation t(14;18), were obtained from Dr John Gribben (Dana-Farber Cancer Institute, Boston, Mass.) and Dr Alan Epstein (University of Southern California, Los Angeles, Calif.), respectively. Cell lines SU-DHL-4, SU-DHL-1, and Karpas 422 were provided by Dr Myron Czuczman (Roswell Park Cancer Institute, Buffalo, N.Y.), and WSU-FCCL and DoHH2 cell lines were obtained from Dr Mitchell Smith (Fox Chase Cancer Center, Philadelphia, Pa.). The cells were grown as suspension cultures in DMEM (Life Technologies, Gaithersburg, Md.), supplemented with 1o % fetal bovine serum, penicillin (100 U/ml), streptomycin (100 µg/ml), and L-glutamine (2 mM) (complete media).

Flow Cytometric Assays

Immunophenotyping.

Indirect immunofluorescence assays were performed with the panel of cell lines described above, using FITC-goat anti-human IgG (Tago, Inc., Burlingame, Calif.) essentially as described previously, and analyzed by flow cytometry using a FACSCaliber (Becton Dickinson, San Jose, Calif.).

Analysis of Apoptosis.

Flow cytometric analysis of cellular DNA was performed following propidium iodide staining. Cells were placed in 24-well plates ($5 \times 10^5$ cells/well) and subsequently treated with MAbs (5 µg/ml). Three wells were prepared with each MAb to study the effects of crosslinking with goat anti-mouse or goat anti-human second antibodies. Following a 2-min incubation with the primary MAbs (37° C., 5% $CO_2$), $F(ab')_2$ goat anti-mouse IgG Fcγ-specific second antibody (Jackson Laboratories, West Grove, Pa.) was added to one well from each primary MAb to adjust the second antibody concentration to 20 pg/ml. $F(ab')_2$ goat anti-human IgG Fcγ-specific (Jackson Laboratories) was similarly added to the second well from each primary MAb, and the volume of the third set was equalized by addition of medium. Following a 48-h incubation (37° C., 5% $CO_2$), cells were transferred to test tubes, washed with PBS, and then resuspended in hypotonic propidium iodide solution (50 mg/ml propidium iodide in 0.1% sodium citrate, 0.1% Triton X-100). Samples were analyzed by flow cytometry using a FACSCaliber. Percent apoptotic cells was defined as the percent of cells with DNA staining before GO/G1 peak (hypodiploid).

Antigen Expression of Cultured Lymphoma Cells

Flow cytometry analysis was performed using indirect immunofluorescent staining to show that hL243γ4P binds to a panel of cultured human B cell lymphomas. A comparison to other surface antigens is shown. As seen in Table 8, the hL243γ4P MAb binds to all the tested cell lines. A stronger expression was observed on Daudi and Raji, but the level of fluorescence staining is strong on all the cell lines tested. Binding was compared to that of humanized MAbs against other B cell antigens (CD74, CD22, CD20), the murine-human chimeric anti-CD20 MAb rituximab, and a humanized anti-CEA MAb (negative control). The staining with hL243γ4P was markedly greater than that of CD22 and CD74 on all seven cell lines. CD20 staining was more variable, as shown by reactivity with the humanized (hA20) and chimeric (rituximab) MAbs. The Burkitt's lines, Daudi, Raji, and Ramos, expressed intermediate levels of CD20, whereas the follicular and diffuse large B cell lymphoma lines assessed varied. In comparison to HLA-DR expression measured by hL243γ4P binding, SU-DHL-6 has higher CD20 expression, Namalwa, and WSU-FSCCL lower CD20 expression, and RL approximately equal expression of both antigens.

Effector Cell Assays

Induction of ADCC was measured in Raji, Daudi, and SU-DHL-6 by calcein AM release. The activity of hL243γ4P was compared to that of the murine L243 and rituximab, as a positive control. As expected, rituximab and the murine L243 induced significantly more cell lysis than the negative controls (no MAb and murine and humanized MN-14) and hL243γ4P did not (FIG. 16).

TABLE 8

Binding of humanized or chimeric MAbs on B cell lines An indirect flow cytometry assay was performed using FITC-GAH Fc specific 2nd antibody staining

| | Geometric Mean Fluorescence | | | | | | |
|---|---|---|---|---|---|---|---|
| | none | anti-CEA (hMN14) | anti-CD74 (hLL1) | anti-CD22 (hLL2) | anti-CD20 (hA20) | anti-CD20 (Rituximab) | anti-HLA-DR (hL243γ4P) |
| Daudi | 3.2 | 3.2 | 48.8 | 517 | 241.0 | 380.5 | 937.4 |
| Namalwa | 2.6 | 2.4 | 7.8 | 64 | 10.1 | 14.1 | 260.9 |
| Raji | 6.9 | 7.0 | 95.1 | 226 | 267.1 | 394.6 | 972.0 |
| Ramos | 3.1 | 3.1 | 23.3 | 146 | 203.7 | 375.0 | 277.6 |
| RL | 2.4 | 2.8 | 7.9 | 51 | 127.5 | 147.8 | 112.2 |
| SU-DHL-6 | 4.6 | 4.9 | 17.3 | 11 | 1199.3 | 1308.9 | 572.3 |
| WSU-FSCCL | 2.7 | 2.7 | 8.7 | 42 | 8.9 | 12.5 | 466.8 |

In Vitro Anti Proliferative Effects

The effect of hL243 on cellular proliferation was assessed using the $^3$H-thymidine uptake assay on Raji, FSCCL, and Namalwa cells (FIG. 17B and Table 9). The effect of hL243γ4P was compared to that of rituximab and to rituximab combined with hL243γ4P, in the presence or absence of a crosslinking anti Fc antibody. In FSCCL, previously shown to be relatively insensitive to rituximab, hL243γ4P yielded significantly greater inhibition of proliferation than rituximab. In Ramos, hL243 and rituximab activity were similar, and the combination was more effective than either alone. The combination may have a synergistic effect. Crosslinking with an anti-human Fc antibody was required for significant anti-proliferative activity to be seen in Ramos. In Namalwa, as with FSCCL, hL243γ4P yielded significantly greater inhibition of proliferation than rituximab and the combination of rituximab and hL243γ4P yielded significantly more inhibition of proliferation than either MAb alone.

TABLE 9

Summary of antiproliferative activity of MAbs with and without crosslinking
(% Inhibition of 3-H-Thymidine uptake)

| Rituximab + hL243 | Rituximab | hL243γ4P |
|---|---|---|
| Antiproliferative activity of MAbs without crosslinking | | |
| Ramos 18.2 ± 4.9 | −7.9 ± 3.6 (0.0001)[a] | 10.1 ± 11.9 (0.3619) |
| FSCCL 75.9 ± 10.2 | 13.4 ± 12.3 (0.0028) | 78.9 ± 1.7 (0.6611) |
| Namalwa 50.1 ± 1.1 | 13.8 ± 5.6 (0.0061) | 27.8 ± 3.3 (0.0038) |
| Antiproliferative activity of MAbs in the presence of anti-human 2$^{nd}$ Ab | | |
| Ramos 69.0 ± 7.0 | 50.5 ± 9.4 (0.0519) | 56.8 ± 0.8 (0.0073) |
| FSCCL 94.5 ± 0.9 | 28.1 ± 9.6 (0.0067) | 94.5 ± 0.8 (0.9984) |
| Namalwa 58.1 ± 2.1 | 14.7 ± 7.0 (0.005) | 51.5 ± 3.0 (0.0416) |

[a]Numbers in parentheses represent P values of the single MAbs in comparison to the combination of rituximab + hL243γ4P Assessment of Apoptosis Induction The mechanism of hL243 γ4P-induced cell death was evaluated by measuring various markers of apoptosis. These included induction of DNA fragmentation, Annexin V/7-AAD staining, measurement of activated caspase-3, loss of mitochondrial membrane potential and activation of the AKT survival pathway.

DNA fragmentation was evaluated by flow cytometry in SU-DHL-6 and Namalwa. Cells were cultured with the MAbs for 48 h with or without a second MAb for crosslinking, followed by DNA staining with propidium iodide. Cells were analyzed by flow cytometry, and positive florescence below the G1 region represents DNA fragmentation and is a measure of apoptosis. Activity of hL243 γ4P was compared to that of humanized MAbs against other B cell antigens, including anti-CD74 (hLL1), anti CD22 (hLL2, epratuzumab), anti-CD20 (hA20), as well as the murine-human chimeric MAb rituximab. Controls included no first MAb and the negative control humanized anti-CEA MAb, hMN-14. hL243 γ4P induced apoptosis in both cell lines, at levels similar to or greater than the other anti-B cell MAbs (FIGS. 18A and 21B).

A kit was used (eg the Guava Nexin™ kit) to discriminate between apoptotic and nonapoptotic dead cells in Daudi cells. The kit utilizes Annexin-V-PE to detect phosphatidylserine (PS) on the external membrane of apoptotic cells and a cell impermeant dye 7-AAD as an indicator of membrane structural integrity. 7-AAD is excluded from live, healthy cells and early apoptotic cells, but permeates late stage apoptotic and dead cells. As shown in FIG. 18B the results of this study indicated that hL243γ4P induced apoptosis similar to mL243 following both 4 h and 24 h treatment. In contrast, the anti-CD20 MAb did not induce measurable apoptosis in Daudi cells. Therefore, hypercrosslinking by a secondary agent, such as anti-human IgG or protein A may be used for induction of apoptosis by anti-CD20 MAbs in many cell lines including Daudi.

In another example, the effects of humanized and murine L243 on mitochondrial potential was studied in different cells, namely, SU-DHL-6, Daudi, Raji, WSU-FSCCL, RL, and Namalwa. Results shown in FIG. 19 indicate apoptotic changes in the mitochondrial membrane potential were observed with both murine and humanized L243 MAbs. Crosslinking with a second antibody may not be needed, but can increase the effect in 2 of 6 cell lines evaluated, FSCCL and Namalwa. The loss of mitochondrial membrane potential induced by hL243γ4P was greater than that of the anti-CD20 MAb (hA20), without a crosslinking agent. With crosslinking the hA20 levels are increased to those of hL243γ4P in 3 of the 6 cell lines (RL, SU-DHL-6, and Daudi).

Induction of activated caspase-3 by humanized and murine L243 was assayed by flow cytometry in a panel of lymphoma cell lines. Result summarized in Table 10 show both the murine and humanized L243 induce activation of caspase-3, at similar levels, in the absence of crosslinking with second antibody. The induction of activated caspase-3 with the L243 MAbs is greater in all cell lines than that of hA20. With a second antibody these levels are increased and the effect of hA20 is similar to that of the hL243γ4P, except in Namalwa and FSCCL, two cell lines which we routinely observe to be relatively insensitive to anti-CD20 MAbs. Cleaved caspase-3 was also assayed in Daudi over a 2 day time course (FIG. 20A). The activity continues to increase for approximately 2 days of L243γ4P incubation. Time points less than 1 h were not done.

TABLE 10

Cleaved Caspase-3 assay

| | Cleaved caspase-3 (% above no MAb control) | | | | |
|---|---|---|---|---|---|
| | Humanized MAbs | | | murine MAbs | |
| | hL243g4P | hA2 | hMN-14 | mL243 | mMN-14 |
| No crosslinking | | | | | |
| Ramos | 26.9 | 3.2 | 0.8 | 15.8 | 3.9 |
| Namalwa | 18.4 | −0.1 | 0.2 | 9.4 | 0.5 |
| FSCCL | 46.4 | 0.7 | 0.3 | 26.2 | −0.7 |
| Daudi | 48.1 | 7.9 | 0.9 | 45.8 | 1.0 |
| RL | 22.5 | 1.5 | −0.1 | 18.2 | −0.3 |
| SU-DHL-6 | 52.2 | 30.9 | 2.3 | 46.5 | 0.2 |
| Raji | 22.5 | 1.5 | −0.1 | 18.2 | −0.3 |
| with 2nd Ab | | | | | |
| Ramos | 71.7 | 67.8 | 7.3 | 40.3 | 3.0 |
| Namalwa | 72.2 | 20.4 | 7.9 | 25.2 | −0.3 |
| FSCCL | 86.7 | 20.0 | 8.4 | 55.0 | 1.5 |
| Daudi | 68.9 | 72.0 | 2.9 | 51.2 | 0.0 |
| RL | 37.3 | 24.2 | 4.0 | 4.0 | 0.7 |
| SU-DHL-6 | 72.1 | 75.8 | 5.5 | 51.4 | −0.9 |
| Raji | 59.8 | 37.4 | 2.8 | 20.4 | −0.3 |

The involvement of AKT in the mechanism of action of L243 was assayed in 6 cell lines by flow cytometry. Cells were incubated with various MAbs for 2 days, then assayed for phospho-AKT. The results listed in Table 11 show that L243 activates AKT in all cell lines. Phospho-AKT levels in anti-CD20 (hA20) treated cells, as well as anti-CD74 and anti-CD22 treated cells (not shown), are similar to untreated cells on all cell lines. To determine the time course of P-AKT activation, Daudi cells were incubated with MAbs for various times, MAbs were removed (by centrifugation) at time points from 0 min to around 2 days (FIG. 20B). These results show activation of AKT by L243 can occur faster than can be measured by this assay, because even at the zero time point P-AKT levels are equal to the 2 day time point.

TABLE 11

P-AKT assay

| | % above no MAb control | | | | |
|---|---|---|---|---|---|
| | humanized MAbs | | | murine MAbs | |
| | hL243g4P | hA2 | hMN-14 | mL243 | mMN-14 |
| Namalwa | 8.4 | −2.8 | 1.3 | 3.5 | −4.4 |
| FSCCL | 25.1 | −1.4 | 3.9 | 16.3 | −1.7 |
| Daudi | 34.9 | 1.0 | −1.4 | 24.5 | −2.1 |
| RL | 5.9 | 1.8 | 0.0 | 1.3 | 1.3 |
| SU-DHL-6 | 29.8 | 0.2 | 1.2 | 26.1 | −0.5 |
| Raji | 5.1 | −0.9 | −1.6 | 17.2 | −4.2 |

In Vivo Therapeutic Efficacy of hL243 in a Xenograft Model of Non-Hodgkin's Lymphoma (Raji)

A therapeutic study was performed to compare the in vivo efficacy of hL243γ4P and mL243 (IgG2a isotype) monoclonal antibodies, in a xenograft model of human non-Hodgkin's lymphoma (Raji). The aim of this study was to determine if hL243γ4P can maintain significant antitumor efficacy in a xenograft model. SCID mice were injected with $2.5 \times 10^6$ Raji cells. Therapy with hL243γ4P or mL243 was initiated 1 day-post tumor cell administration. Results are shown in FIG. 21. Both groups of mice injected with saline or with non-specific control antibody, hMN14, had a median survival time (MST) of 17 days. All the groups of mice treated with either humanized or murine L243 had significantly improved life span compared to mice injected with saline or hMN14 ($P<0.0001$). Treatment with various doses of hL243γ4P resulted in a dose-response relationship, with mice receiving higher doses having better survival times. In the group of animals treated with various doses of mL243 IgG2a, the cure rate was in the range of 80-100%.

Example 7. Anti-HLA-DR Antibody Therapy in Spontaneous Canine Lymphoma

Expression of HLA-DR on hematological malignancies has generated considerable interest in its development as a target for antibody-based therapy. Here we describe the use of anti-HLA-DR monoclonal antibodies (mAbs), L243 and IMMU-114 (hL243γ4P), a humanized IgG4 mAb engineered to eliminate adverse reactions associated with complement-activation, for antibody therapy in dogs with lymphoma.

Normal and malignant canine B cell binding, induction of apoptosis, antibody-dependent cellular-cytotoxicity (ADCC), complement-dependent cytotoxicity (CDC), and direct cytotoxicity of L243 and IMMU-114 were measured in vitro. Safety and pharmacokinetic data on L243 and IMMU-114 administration were collected in normal dogs, followed by a preliminary trial of L243 in dogs with advanced lymphoma or unresectable plasmacytoma.

L243 and IMMU-114 were observed to bind to normal canine lymphocytes and canine lymphoma cells. In vitro, murine L243 and IMMU-114 binding yielded a reduction in viable cell counts and induction of apoptosis in canine lymphoma cells. When incubated with canine serum or peripheral blood mononuclear cells, L243, but not IMMU-114, induced CDC and ADCC, respectively. In vivo, both anti-HLA-DR mAbs can be administered safely to dogs and bind to malignant cells. Evidence of clinical activity (hematopoietic toxicity and tumor response) was observed in dogs with advanced-stage lymphoma following L243 immunotherapy.

To avoid complications associated with complement-dependent cytotoxicity (CDC) and antibody-dependent cellular cytotoxicity (ADCC), we recombinantly-engineered a humanized IgG4 construct of the murine anti-HLA-mAb, L243, referred to as hL243γ4P (IMMU-114) (Stein et al., 2006, Blood 108:2736-44). The IgG4 isotype was prepared because human Fcγ receptors are known to have low affinity for the human IgG4 isotype (Ravetch and Kinet, Ann Rev Immunol, 1991, 9:457-92). A point mutation, Ser241Pro, was introduced into the hinge region of the γ4 sequence in order to avoid formation of half-molecules when the antibody is expressed and produced in mammalian cell cultures, thus the designation, γ4P. As discussed in the preceding Examples, replacing the Fc region of a humanized IgG1 anti-HLA-DR mAb with the IgG4 isotype abrogated the effector cell functions of the antibody (ADCC and CDC), while the antigen-binding properties, anti-proliferative capacity (in vitro and in vivo), and the ability to induce apoptosis concurrent with activation of the AKT survival pathway and other signaling pathway effects, were retained. Thus, IMMU-114 is indistinguishable from the parental murine mAb and a humanized IgG1 anti-HLA-DR mAb in assays dependent upon antigen recognition. The abrogation of ADCC and CDC may be preferred for in vivo therapeutic use.

Materials and Methods

Antibodies.

The following mAbs were used for phenotyping: anti-CD3-FITC, anti-CD4-FITC, anti-CD8-PE, and B cell-PE, purchased from Serotec Ltd (Raleigh, N.C.), unlabeled anti-human CD22 (LL2) and anti-human CD74 (LL1), supplied by Immunomedics, Inc. (Morris Plains, N.J.), unlabeled anti-human-CD3, -CD20, and -CD45 (Leu 4, Leu-16, and H-Le-1, respectively), purchased from BD Biosciences (San Jose, Calif.), and anti-CD20 mAbs, 2B8 and 1F5, purified from culture fluids of hybridoma cells obtained from the American Type Culture Collection (ATCC, Manassas, Va.). Murine mAbs Ag8 (P3x63 Ag8, ATCC) and MN-14 (anti-carcinoembryonic antigen [CEA, CEACAM5 or CD66e]) were used as isotype controls. L243 and humanized mAbs, IMMU-114 (hL243γ4P), milatuzumab (hLL1, anti-CD74 mAb) (Stein et al., Blood, 2004, 104:3705-11), veltuzumab (hA20, anti-CD20) (Stein et al., Clin Cancer Res, 2004, 10:2868-78), epratuzumab (hLL2, anti-CD22) (Leung et al., Molecular Immunol, 1995, 32:1416-27), and labetuzumab (hMN-14, anti-CEA) (Sharkey et al., Cancer Res, 1995, 55:5935s-45s), were from Immunomedics, Inc.

Flow Cytometry.

Peripheral blood lymphocyte subsets were determined using flow cytometry. The different leukocyte populations were identified by their distinctive position on forward and side scatter plots. The lymphocyte population was gated and 10,000 events were acquired for each antibody. All flow cytometry experiments were performed and analyzed using a FACSCalibur (Becton Dickinson, San Jose, Calif.). The data were analyzed with CellQuest software. Immunostaining was performed according to the manufacturer's directions. Briefly, a 100-µl aliquot of whole blood in EDTA was incubated with either antibody or isotype control antibody for 15 min at room temperature. Red blood cells were lysed with 2 ml of FACS lysing solution and incubated for 5 min. The cells were washed in phosphate-buffered saline (PBS), pH 7.4. The cell pellet was resuspended in PBS containing 20 mM glucose and 1% bovine serum albumin and immediately assayed by flow cytometry.

Determination of HLA-DR and CD20 antigen expression on normal and neoplastic cells was performed by indirect immunofluorescence assays using FITC-goat anti-mouse IgG (GAM, Invitrogen, Carlsbad, Calif.), as described previously (Stein et al., Blood, 2006, 108:2736-44).

In Vitro Cytotoxicity and Apoptosis Assays.

Apoptosis was evaluated by flow cytometry. Briefly, cells were incubated with mAbs for 48 h with or without a second antibody for cross-linking, followed by DNA staining with propidium iodide. Samples were analyzed by flow cytometry using a FACSCalibur. Percentage of apoptotic cells was defined as the percentage of cells with DNA staining before G1/G0 peak (hypodiploid).

Standard $^{51}$Cr release assays were used to measure ADCC and CDC. Briefly, for CDC a 1/8 final dilution of canine serum was used as the source of complement, followed by a 3-h incubation. Cells treated with 0.25% Triton X-100 were included as 100% lysis control, and cells treated with complement alone as 0% lysis. For ADCC, effector:target cell ratios of approximately 50:1 were used, and incubations were for 4 h. All assays were performed in triplicate.

In Vivo Studies.

Sterile antibodies were diluted in a total volume of 90 ml and 250 ml of 0.9% NaCl for administration to normal dogs and dogs with lymphoma, respectively. All dogs were premedicated with 4 mg/kg diphenhydramine intramuscularly 20 min prior to antibody infusion. The dogs were monitored continuously during the infusion, and vital signs and body temperature were recorded every 30 min. If adverse events (vomiting, erythema, pruritus, weakness, tachycardia) were observed, the infusion was stopped for at least 15 min and restarted at half the initial infusion rate. The normal dogs' rectal temperature was taken twice daily for 7 days following each antibody infusion. Adverse events were graded according to the veterinary co-operative group—common terminology criteria (Veterinary co-operative oncology group, Vet Comparative Oncol, 2004, 2:194-213).

Normal Dogs.

Intact female beagle dogs were used to assess systemic toxicity with L243 (2 dogs) and IMMU-114 (2 dogs) antibody administration. The dogs were deemed healthy based on physical examination, complete blood cell count, biochemical profile, and urinalysis. L243 was administered at 1.5 mg/kg of body weight over a planned 90-min interval to the first dog. This dose was extrapolated from previous dose ranging studies in mice. The antibody infusion was repeated on day-7 in this dog. The dose of L243 was increased to 3 mg/kg for the second dog, since there was minimal toxicity noted in dog-1. The second dose was repeated on day-2 rather than day-7, to determine if increased toxicity would be detected with a shorter interval between treatments. IMMU-114 was administered at 3 mg/kg infused over a 90-min period to 2 dogs. One of the dogs was infused a second time 2 weeks later at 1.3 mg/kg.

Blood was collected into ethylenediamine tetraacetic acid (EDTA) tubes for complete blood cell counts and peripheral blood lymphocyte phenotyping at 4, 24, 48, and 72 h and at 7, 14, 21 days after the first infusion. Biochemical profiles and urine were analyzed at 7, 14, and 21 days after the first infusion. Dogs were humanely euthanized by intravenous pentobarbital sodium injection 30 days after the first infusion. Necropsies were performed post mortem and tissue samples were collected in formalin for histologic review by a board certified pathologist.

Dogs with Lymphoma.

Dogs were enrolled in this study if they had histologic or cytologic confirmation of lymphoma or plasma cell neoplasia and had previously failed or were refractory to conventional cytotoxic chemotherapy or if the owner had declined other therapy. Chemotherapy was not administered concurrently or less than 3 weeks prior to treatment with HLA-DR mAb. Pretreatment evaluation for all tumor-bearing dogs included physical examination, complete blood cell count, biochemical profile, and urinalysis. Dogs were excluded if there was evidence of ≥grade 2 toxicity on screening studies. Lymph nodes or tumors were measured in 3 dimensions and tumor volume was calculated as the product of length, width, height, π/6. Dogs received 1 to 4 treatments administered at 2-week intervals at a dosage of 3 mg/kg intravenously. Based on the normal dog studies above, the starting protocol for infusion of L243 was planned over a 4-h period. Due to delays caused by infusion reaction in some of the dogs, the infusion was slowed to 3 mg/kg over 12 h. Adverse infusion events were monitored continuously in an intensive care setting during the infusion. Complete blood cell count, chemistry profile, urinalysis and tumor measurements were evaluated weekly.

Enzyme-Linked Immunoabsorbent Assay (ELISA).

L243 and IMMU-114 serum levels were measured by ELISA. Two ml of whole blood were collected pretreatment, at the end of the antibody infusion, 1 h after the end of the infusion and at 24 h. The samples were allowed to clot at room temperature for 30 min and the serum was separated and frozen at −80° C. prior to analysis. The ELISA assays were performed in 96-well PVC microtiter plates. Plates were coated overnight with goat anti-mouse IgG F(ab')$_2$ fragment specific antibody at 10 μg/ml in PBS, 0.02% NaN$_3$ (Jackson Immunoresearch, West Grove, Pa.), then blocked with 1% BSA/PBS, 0.02% NaN$_3$ for 1 h at room temperature. Triplicate serum dilutions (in 1% BSA/PBS, 0.02% NaN$_3$ at 1/3, 1/10, 1/30, and 1/100) were incubated for 1 h in the coated wells. A standard curve of L243 or IMMU-114 was run in the same plate. After washing with PBS, 0.05% Tween, peroxidase conjugated goat anti-mouse (or anti-human) IgG, Fcγ specific antibody (1:3000 dilution in 1% BSA/PBS, Jackson Immunoresearch) was added and the plate was incubated for an additional 1 h at room temperature in the dark. The plates were washed, developed with o-phenylenediamine dihydrochloride substrate solution and read at 490 nm, after stopping the reaction by adding 1.5 N H$_2$SO$_4$.

Statistics.

P-values were calculated using the Student's t test. Two-sided tests were used throughout. Values less than 0.05 are considered statistically significant. For ADCC and CDC assays, P values were calculated versus the no-antibody control.

Results

In Vitro Effects of L243 on Proliferation and Apoptosis.

Lymph node aspirates from four dogs with lymphoma were incubated with mAb L243 in vitro to determine the effects of the mAb on proliferation and apoptosis. All four specimens were positive for L243 binding (FIG. 22A). Induction of apoptosis by L243 was evaluated by flow cytometry assays measuring hypodiploid DNA. Cells were cultured with the mAbs for 48 h with or without a second mAb for cross-linking, followed by DNA staining with propidium iodide. Cells were analyzed by flow cytometry, and positive fluorescence below the G0/G1 region represents DNA fragmentation and is a measure of apoptosis. As shown in FIG. 22B, L243 caused specific induction of apoptosis in the presence of goat anti-mouse IgG second antibody (P<0.05 vs. crosslinked isotype control) in all four specimens. Viable cell counts were measured after 2-day incubations of the tumor aspirates with L243 plus goat anti-mouse IgG second antibody. Decreases in the viable tumor cell population of 43% (P=0.0088) and 23% (P=0.097) were obtained in specimens 160812 and 160965, respectively, vs. Ag8 plus goat anti-mouse IgG second antibody (FIG. 22C). Specimens 160540 and 150836 were not tested by this assay. ADCC and CDC assays were performed on one tumor aspirate, from dog 171205, using PBMCs or serum isolated from that animal as sources of effector cells and complement, respectively. Statistically significant lysis was observed with L243 but not an isotype control (MN-14) in both assays. For CDC, lysis was 38.1%±0.9% (P=0.0004) and 1.1±2.2% (P=1.0000) for L243 and isotype control, respectively. For ADCC, lysis was 26.6±15.9% (P=0.0319) and −6.9±18.36% (P=0.4544) for L243 and isotype control, respectively. Thus, crosslinked L243 yields a specific therapeutic effect on canine lymphoma aspirates, leading to a reduction in viable cell count and induction of apoptosis, as measured by DNA fragmentation. When incubated with dog serum or PBMCs, L243 induces CDC and ADCC.

We also demonstrated that IMMU-114 (humanized, engineered L243) binds to canine lymphoma cells (Table 12). In addition, IMMU-114 induces apoptosis in the canine lymphoma cells when crosslinked with an anti-human IgG second antibody (FIG. 23A). Evaluation of the ability of IMMU-114 to induce CDC and ADCC was performed on one canine lymphoma aspirate (171205). As shown in FIGS. 23B and 23C, murine L243 but not IMMU-114 yielded specific cell lysis of the dog lymphoma cells, confirming the lack of CDC and ADCC effector functions of IMMU-114.

TABLE 12

Characteristic phenotype of a canine lymphoma aspirate (150836).

| Murine Abs | % Positive | Mean FL | Humanized mAbs | % Positive | Mean FL |
|---|---|---|---|---|---|
| None | 3.9 | 3.4 | none | 4.5 | 3.2 |
| Ag8 | 2.8 | 3.0 | hMN-14 | 4.6 | 3.2 |
| L243 | 77.8 | 10.4 | IMMU-114 | 26.2 | 5.5 |
| 2B8 (anti-CD20) | 2.6 | 3.1 | hA20 (anti-CD20) | 4.0 | 3.3 |
| LL1 (anti-CD74) | 6.7 | 4.0 | hLL1 (anti-CD74) | 4.7 | 3.3 |
| LL2 (anti-CD22) | 5.1 | 3.7 | hLL2 (anti-CD22) | 4.9 | 3.4 |

L243 Administration In Vivo.

Safety data on L243 infusion was collected in two normal dogs, followed by a trial in 6 dogs with relapsed lymphoma, and 1 dog with an unresectable plasmacytoma.

Normal Dogs.

Dog 1 received 2 infusions of 1.5 mg/kg, 7 days apart. An infusional reaction occurred during the first antibody administration that included grade I nausea/vomiting and grade I fever. Decreasing the infusion rate by 50% (from an initial rate of 0.2 mg/ml/min) eliminated the adverse reactions. There were no adverse events during the second infusion. Dog 2 received 2 infusions of 3.0 mg/kg, 48 hours apart (0.25 mg/ml/min). There were no adverse reactions during either infusion. There were no significant changes in the post-infusion biochemical profiles or urinalysis in either dog. Mature neutrophils were transiently elevated in Dog 2 (13.3×10$^3$/μl; normal range 3.4-9.7×10$^3$/μl) 24 h after the first infusion and normalized within 24 h. Both dogs had a marked transient increase in band neutrophils. Dog 1 had 1000/μl band neutrophils 4 h after the second infusion (normal range 0-100/μl); Dog 2 had 1300/μl band neutrophils 24 h after the first infusion. Both dogs had normal band neutrophil counts 24 h later. Lymphopenia (800/μl—dog 1, 500/μl—dog 2: normal range 1000-4000/μl) was noted 4-24 h following the first infusion in both dogs and following the second infusion in dog 2. Lymphocytes returned to normal within approximately 1 week following infusion. Peripheral blood lymphocyte subset phenotyping indicated a decrease in both B and T cell lymphocytes (FIG. 24). Such rapid changes in neutrophils and lymphocytes represent a non-specific component to immunogens in dogs. Resolution of the neutrophilia occurred within one day and lymphocyte populations recovered over a 7-day period. Complete necropsy examination of Dogs 1 and 2 did not reveal any gross or histologic abnormalities.

Tumor-Bearing Dogs.

Seven dogs with lymphoma/plasmacytoma were treated with L243. The median age of the patients was 10.8 years (range 8.4-11.9 years). The median body weight was 35 kg (range 12.6-51.2 kg). There were 4 male dogs (2 intact, 2 castrated), and 3 female dogs (all spayed). Four of the dogs had B cell lymphoma, 2 had T-cell lymphoma, and 1 had an unresectable plasmacytoma. All dogs were staged according to WHO guidelines for canine lymphoma: 3 were stage V, 2 were stage III, and one remained incompletely staged. Four of the six lymphoma patients had failed initial conventional and rescue chemotherapy treatments. The remaining two lymphoma patients had received prednisone as their only therapy prior to presentation and their owners' had declined standard chemotherapy. All previous chemotherapeutic agents were discontinued 2-4 weeks prior to L243 therapy.

Toxicity.

Infusional side-effects were common with 6/7 patients, experiencing grade 1 nausea or vomiting and 5/7 experiencing grade 1 fever. Slowing the infusion rate abrogated the adverse reactions. Two dogs received dexamethasone at 0.5-2 mg/kg i.v. due to vomiting and elevated temperature. No dog had treatment discontinued due to adverse events. Hematologic toxicity was noted in 3/7 patients. One dog had grade 1 neutropenia and grade 1 thrombocytopenia two weeks after the first infusion. This dog received a total of 3 treatments and did not exhibit any additional hematologic abnormalities. In two dogs, grade 3 neutropenia and grade 4 thrombocytopenia were observed one week after the second infusion. Both of these dogs were heavily pretreated with chemotherapy prior to antibody infusion. Bone marrow aspirates indicated a non-specific granulocytic and megakaryocytic hypoplasia. One dog was euthanized due to hemorrhage from multiple ulcerated cutaneous lymphoma lesions. The second dog's cytopenias resolved uneventfully by the fourth week post infusion. One dog died suddenly at home approximately 5 days after L243 therapy due to rapidly progressing, resistant lymphoma. A necropsy was not performed.

Response to Therapy.

Two dogs with advanced, multicentric B cell lymphoma had a transient response to L243 therapy. One dog had stable disease with complete resolution of circulating lymphoblasts for 5 weeks following the second infusion, with improvement in attitude and appetite. This dog received a total of three treatments. His disease progressed 8 weeks after his first L243 treatment. The second dog had a 50% reduction in the size of peripheral lymph nodes observed by physical examination and measurement of peripheral lymph node volume one week after the first treatment. The partial response lasted 8 weeks before progressive disease was noted. This dog received a total of 4 treatments without evidence of any toxicity. Both dogs received a brief course (1-2 weeks) of corticosteroid prior to L243 therapy. In each instance, the dogs had progressive disease on corticosteroids prior to L243 infusion and all corticosteroid therapy was discontinued before treatment.

A comparison of cells aspirated from a lymph node prior to L243 with cells obtained one week after the first L243 infusion was performed in order to assess in vivo targeting of the L243 mAb. The histograms represented baseline and one-week post infusion aspirated cells, to which no first or second antibodies were added in vitro (not shown). The profiles of the baseline cells and week-1 cells overlapped (not shown). The cells were incubated in vitro with FITC-labeled GAM, to detect cells that were labeled with L243 in vivo (not shown). Cells obtained from the same lymph node 1 week after treatment with L243 were shifted to the right of the baseline cells, demonstrating the binding of murine IgG to the cell surface (not shown). The cells were incubated in vitro with L243 and FITC-GAM to determine whether the cells were saturated with mAb L243. Aspirated cells taken 1 week after treatment with L243 coincided with the baseline cells because the in vivo and in vitro binding of L243 IgG to the cell surface are indistinguishable after saturating doses of L243 (not shown). Both groups exhibited higher mean fluorescence compared to that of the FITC-GAM labeled cells, indicating that the in vivo L243 dose administered did not saturate all malignant cells in the node (not shown). Data obtained from cells aspirated 2 weeks after infusion continue to demonstrated L243 binding to malignant lymphocytes (not shown). An alternate explanation is that some of the bound L243 was internalized or processed, and the antigen remains on or returns to the cell surface, able to bind additional antibody. Cells were incubated in vitro with Ag8 (isotype matched, nonspecific mAb) and FITC-GAM. Aspirated cells taken 1 week after infusion with L243 were shifted to the right of the baseline cells, again demonstrating the binding of murine IgG to the cell surface (not shown). Only the cells labeled in vivo with L243 bind to the FITC-GAM, because Ag8 does not bind to the cells. This assay demonstrated that L243 targeted the tumor cells in vivo.

The L243 antibody was measured by ELISA in the serum of the last treated dog (152616). Samples were collected prior to the antibody infusion, at the end of the infusion, 1 h post infusion and at 24 h at each of the 4 treatments (FIG. 25). The serum level of L243 detected after the second infusion was markedly higher than after the first infusion. This suggests that the antigen pool present on cell surfaces was either blocked or eliminated by the first infusion. Infusions 3 and 4 yielded progressively lower serum concentrations of L243. This was likely due to an anti-antibody response causing rapid clearance of the infused murine L243 antibody. Because the presence of anti-mouse IgG was not measured, reappearance of an antigen sink cannot be ruled out.

IMMU-114 Administration In Vivo.

Once IMMU-114, the humanized reengineered IgG4 form of murine L243, became available, it was administered to 2 normal beagles at 3 mg/kg over 90 min. There was no infusion reaction noted in either dog during the infusion. One of the dogs was infused a second time 2 weeks later (at 1.3 mg/kg). A mild infusion reaction that included head shaking, mild fever and vomiting occurred following the second infusion. The severity of the reaction was lessened by slowing the rate of the infusion. This may suggest the development of anti-human IMMU-114 antibody. CBCs and biochemical panels were conducted with no significant changes noted over a 2-week period, with the exception of a transient lymphopenia as also observed with L243 infusion. Pharmacokinetic (PK) data obtained at the end of infusion, and 1, 4, 24, 48, 72 h, 1 week, and 2 weeks post-infusion indicated a rapid clearance within the first few hours, with about 50% of the IMMU-114 antibody cleared within 2 h, and with the remaining antibody clearing with a half-life of ~2 days (FIG. 25).

DISCUSSION

Naturally-occurring lymphoma in dogs is extremely common and has been validated as a useful model of high-grade, B cell, non-Hodgkin's lymphoma in humans. Conventional chemotherapeutic management of lymphoma in dogs, as in humans, is limited with 5-20% 2-year survival rates following CHOP-based chemotherapeutic protocols. The availability of canine lymphoma patients, the ability to investigate novel strategies with repeated sampling of normal and tumor tissue or fluid, as well as the design of rigorous clinical trials to determine relevant therapeutic endpoints, are recognized advantages of this model as a bridge from preclinical investigations to humans. Although anti-CD20 antibodies have contributed to improved outcomes in some forms of lymphoma in humans, the commercially available human anti-CD20 antibodies do not bind sufficiently with canine B cell lymphomas to permit further investigations of this strategy. However, substantial opportunities exist to expand the investigation of other antibody-based immunologic therapeutics.

Lymphoma is an increasingly common form of cancer with a wide range of immunologic and genetic subcategories with equally diverse prognoses. Aggressive forms of non-Hodgkin's lymphoma are currently controlled with chemotherapy with or without antibody infusions with only a moderate degree of success. Novel immunotherapeutic approaches, such as infusion of anti-B cell mAbs to improve the management of lymphoma, are traditionally examined in murine models but should be more carefully evaluated prior to human study to identify and better anticipate the impact of such interventions. Studies in the present canine model are important to the translation of IMMU-114 to clinical studies in humans, particularly given the prior clinical experience with another anti-HLA-DR antibody (Hu1D10; apolizumab), where moderate to severe side effects, primarily related to robust immune effector activity (e.g., mainly CDC) limited its dosing (Shi et al., Leuk Lymphoma, 2002, 43:1303-12. In order to expedite the scientific and practical decisions about progression of new immunotherapeutic strategies into humans with B cell malignancies, prudent use of the canine lymphoma model to address both safety and efficacy represents a truly comparative approach to cancer investigation.

The effects of anti-HLA-DR antibodies on malignant cells have been studied extensively. The most widely recognized function of class II major histocompatibilty complex (MHC) molecules is the recognition of foreign antigen fragments and presentation to CD4 T lymphocytes. In addition, signals delivered via HLA-DR molecules contribute to the functioning of the immune system by up-regulating the activity of adhesion molecules, inducing T-cell antigen counter receptors, and initiating the synthesis of cytokines. Stimulation of HLA molecules by antibodies has been shown to affect growth, differentiation, and immunoglobulin secretion by B lymphocytes, as well as production of cytokines, modulation of expression of growth factor receptors, cell adhesion, and co-stimulatory molecules by B cells and monocytes (Nagy et al., J Mol Med, 2003, 81:757-65). HLA molecules have also been shown to serve as receptors that activate various cell death pathways, including caspase-dependent and caspase-independent alternative pathways of apoptosis (Nagy et al., J Mol Med, 2003, 81:757-65; Mone et al., Blood, 2004, 103:1846-54; Newell et al., PNAS USA 1993, 90:10459-63; Truman et al., Blood, 1997, 89:1996-2007). Functions reported to be affected by incubation of cells with L243 have included signal transduction, growth inhibition, Fas-mediated apoptosis, interactions with actin microfilaments, TNF-α and TNF-β gene expression, cell adhesion, ADCC, and others (see, e.g., Nagy et al., J Mol Med, 2003, 81:757-65; Mone et al., Blood, 2004, 103:1846-54; Newell et al., PNAS USA 1993, 90:10459-63; Truman et al., Blood, 1997, 89:1996-2007; Altomonte et al., J Cell Physiol, 2004, 200:272-6; Aoudjit et al., Exp Cell Res 2004, 299:79-90; Guo et al., Hum Immunol, 1999, 60:312-22). Enhanced cell kill over rituximab alone is demonstrated when the IMMU-114, is combined with rituximab in vitro (Stein et al., 2006, 108:2736-44). Recent studies have shown that antigen expression is not sufficient for cytotoxicity, but that antibody-induced activation of extracellular signal-regulated kinase (ERK) and c-Jun N-terminal kinase (JNK) stress signaling pathways are also required (Stein et al., unpublished).

The results reported here show that the anti-HLA-DR antibodies, L243 and IMMU-114, are able to induce cell death of canine lymphoma cells in vitro and can be given safely to dogs with lymphoma that are not heavily pretreated with chemotherapy. From this study, we were able to obtain valuable information regarding the dose and infusion rate for canine patients diagnosed with B cell lymphomas. The primary reaction following initiation of the infusion was mild and was characterized by a grade 1 fever and grade 1 nausea/vomiting. Myelosuppression was only noted in canine patients that were heavily pretreated with other chemotherapeutic agents. No other severe acute reactions were observed.

Two dogs with T-cell lymphoma were treated. Our preliminary work demonstrated that the T-cell form of lymphoma did not bind L243 significantly. We chose to enroll these dogs to identify whether the infusion reaction may be non-specific in an L243-negative tumor. Neither dog expressed the L243 antigen on the tumor cells. Both of these dogs experienced similar infusion reactions to those dogs with L243+ B cell tumors.

All dogs had tumor measurements and were evaluated for response. The two dogs with B cell lymphoma that had received prednisone as their only prior therapy experienced measurable responses to L243. One experienced a minor, but measurable, response with significant improvement of advanced symptoms, while the second had a partial response lasting 8 weeks. Five dogs did not demonstrate an obvious tumor response. Dogs in this group were L243-negative (T-cell lymphoma) or had end-stage disease at the time of treatment.

In vitro studies showed that murine L243 and its humanized IgG4 construct, IMMU-114, bind to normal and malignant canine lymphocytes and subsequently induce biological activity. In vivo studies indicate that the murine and humanized mAbs can be administered safely to dogs with lymphoma and bind to the malignant cells in nodal tissue. Preliminary evidence of disease stabilization was observed in dogs with advanced-stage lymphoma following anti-HLA-DR immunotherapy.

Example 8. Comparative Effects of Different Specificity Antibodies

The cross-reactivity of a panel of anti-human B cell mAbs with dog lymphocytes was evaluated using peripheral blood from a healthy dog. A human blood sample was tested at the same time as a control. Single color indirect flow cytometry analysis was performed. Reactivity of the mAb panel with the human lymphocytes was within the expected range. MAbs against human CD20 (1F5) and HLA-DR (L243) reacted with the dog lymphocytes. Anti-human CD22 (LL2), CD74 (LL1), and mAbs recognizing human CD3 (Leu 4), CD20 (Leu-16), and CD45 (H-Le-1) did not cross-react with dog lymphocytes. Based on these initial results, tumor aspirates obtained through a large gauge needle from dogs with lymphoma were tested for binding to anti-HLA-DR and anti-CD20 murine mAbs. Anti-HLA-DR (L243) was positive in 32/35 samples (greater than 5 units above the isotype control) and strongly positive (greater than 10 units above the negative control) in 30/35 samples. In contrast, anti-CD20 (2B8 used in these studies) was positive in 5/21, including 3 strongly positive. Reactivity of L243 was confirmed on the peripheral blood of several of these dogs.

The comparative effect of the different specificity antibodies on survival of mice injected with WSU-FSCCL tumor cells is shown in FIG. 26. The mL243 and hL243γ4P antibodies produced a significant increase in survival compared to the other antibodies tested.

We examined the reactivity and cytotoxicity of hL243γ4P on a panel of leukemia cell lines. hL243γ4P bound to the cell surface of 2/3 AML, 2/2 mantle cell, 4/4 ALL, 1/1 hairy cell leukemia, and 2/2 CLL cell lines, but not on the 1 CML cell line tested. Cytotoxicity assays demonstrated that hL243γ4P was toxic to 2/2 mantle cell, 2/2 CLL, 3/4 ALL, and 1/1 hairy cell leukemia cell lines, but did not kill 3/3 AML cell lines despite positive staining. As expected, the CML cell line was also not killed by hL243γ4P.

Additional comparative data for different antibodies tested against a variety of NHL cell lines is presented in Table 13. Table 14 shows the relative expression of HLA-DR compared with CD74, CD22 and CD20 in different tumor types. Table 15 illustrates the relative cytotoxicity of hL243γ4P compared to other anti-B cell mAbs in different tumor types. The percent of untreated values in MTT assay are shown. Highlited values represent a significant decrease from untreated (P<0.05). HLA-DR is expressed on all B-lymphoma and leukemia tested cell lines at markedly higher levels than CD20, CD22, and CD74. Despite positive staining AML cell lines are not killed by hL243g4P. Variation in expression and cytotoxicity profiles between the mAbs suggests that combination therapies may yield greater effects than the mAbs given singly.

TABLE 13

Comparative reaction of different specificity antibodies with NHL cell lines

| Murine MAb | NHL Cell Line | | | | |
|---|---|---|---|---|---|
| | RL | Raji | Ramos | SU-DHL6 | Daudi |
| Ag8 (neg control) | 3.3 | 2.6 | 4.6 | 2.5 | 6.9 |
| L243 (HLA-DR) | 157.2 | 623.7 | 92.9 | 370.3 | 435.5 |
| LL1 (CD74) | 7.5 | 63.8 | 12.3 | 27.9 | 26.4 |
| LL2 (CD22) | 5.4 | 30.8 | 10.7 | 9.7 | 43.5 |
| 2B8 (CD20) | 46.7 | 102.7 | 64.2 | 148.8 | 101.5 |

TABLE 14

Expression of HLA-DR compared to CD74, CD22 and CD20 (mean FL)

| | Cell line | No mAb | Ag8 (Isotype control) | L243 (HLA-DR) | LL1 (CD74) | LL2 (CD22) | 2B8 (CD20) |
|---|---|---|---|---|---|---|---|
| AML | GDM-1 | 16.8 | 20.1 | 1072.7 | 69.5 | 28.5 | 15.6 |
| | Kasumi-1 | 18.2 | 17.0 | 24.0 | 23.8 | 20.9 | 14.5 |
| | Kasumi-3 | 9.6 | 15.7 | 565.3 | 18.4 | 13.9 | 11.0 |
| MCL | Jeko-1 | 14.3 | 17.4 | 1895.0 | 32.7 | 25.0 | 454.8 |
| | Granta-519 | 15.3 | 16.9 | 2107.9 | 50.8 | 28.6 | 677.2 |
| ALL | RS4; 11 | 6.4 | 8.6 | 152.0 | 24.3 | 20.9 | 11.5 |
| | REH | 3.9 | 3.9 | 2088.4 | 61.1 | 16.8 | 23.5 |
| | 697 | 4.9 | 5.6 | 259.3 | 20.6 | 15.9 | 6.9 |
| | MN60 | 8.1 | 10.5 | 1221.1 | 25.9 | 17.1 | 162.4 |
| CML | K562 | 3.2 | 4.1 | 4.9 | 7.0 | 4.3 | 4.3 |
| Hairy cell leukemia | HC-1 | 4.8 | 3.5 | 514.9 | 36.7 | 17.8 | 42.2 |
| CLL | MEC-1 | 4.7 | 6.0 | 1700.5 | 44.7 | 49.0 | 175.3 |
| | WAC | 15.8 | 14.4 | 787.5 | 43.6 | 20.1 | 275.4 |

TABLE 15

Cytotoxicity of hL243γ4P compared to other anti-- cell mAbs

| | | GAN 2$^{nd}$ Ab | hL243γ4P (HLA-DR) | Milatuzumab (CD74) | Veltuzumab (CO20) |
|---|---|---|---|---|---|
| AML | GDM-1 | − | 105.9 ± 14.4 | 102.0 ± 15.2 | 100.3 ± 10.5 |
| | | + | 104.1 ± 10.0 | 128.9 ± 9.5 | 111.9 ± 14.5 |
| | Kasumi-1 | − | 92.1 ± 6.0 | 83.9 ± 5.2 | 88.1 ± 16.3 |
| | | + | 88.6 ± 10.6 | 88.1 ± 8.9 | 99.4 ± 4.6 |
| | Kasumi-3 | − | 120.4 ± 7.7 | 116.1 ± 7.3 | 112.3 ± 8.3 |
| | | + | 113.9 ± 9.9 | 123.3 ± 8.9 | 111.8 ± 18.0 |
| MCL | Jeko-1 | − | 41.3 ± 5.4 | 116.7 ± 10.1 | 124.1 ± 7.9 |
| | | + | 25.8 ± 1.7 | 33.1 ± 1.0 | 66.8 ± 3.0 |
| | Granta-519 | − | 78.8 ± 3.2 | 103.8 ± 5.7 | 94.6 ± 3.4 |
| | | + | 64.7 ± 2.2 | 64.7 ± 3.2 | 64.8 ± 1.6 |
| ALL | RS4; 11 | − | 79.6 ± 3.7 | 102.0 ± 10.2 | 88.1 ± 10.6 |
| | | + | 90.8 ± 9.7 | 88.6 ± 5.3 | 106.9 ± 5.5 |
| | REH | − | 50.4 ± 5.0 | 79.1 ± 10.2 | 87.9 ± 7.1 |
| | | + | 29.4 ± 2.5 | 29.3 ± 2.1 | 94.7 ± 9.8 |
| | 697 | − | 90.8 ± 13.4 | 105.1 ± 8.2 | 115.0 ± 12.1 |
| | | + | 57.8 ± 3.9 | 59.3 ± 8.2 | 124.2 ± 7.6 |
| | MN60 | − | 34.9 ± 2.8 | 87.6 ± 14.9 | 92.1 ± 10.2 |
| | | + | 26.8 ± 2.5 | 34.9 ± 2.8 | 56.0 ± 2.0 |
| CML | K562 | − | 100.5 ± 7.8 | 100.3 ± 10.1 | 93.8 ± 12.8 |
| | | + | 124.8 ± 20.6 | 108.9 ± 7.4 | 99.8 ± 8.7 |
| hairy cell leukemia | HC-1 | − | 27.5 ± 2.1 | 120.5 ± 5.8 | 91.2 ± 10.8 |
| | | + | 16.9 ± 1.1 | 18.8 ± 1.3 | 48.7 ± 9.9 |
| CLL | MEC-1 | − | 68.8 ± 2.6 | 100.7 ± 8.2 | 99.1 ± 4.8 |
| | | + | 29.6 ± 2.0 | 51.7 ± 2.0 | 62.7 ± 5.8 |
| | WAC | − | 54.4 ± 7.3 | 97.0 ± 11.5 | 101.6 ± 16.9 |
| | | + | 41.1 ± 3.5 | 50.5 ± 6.9 | 62.3 ± 8.2 |

FIG. 27 illustrates the ex vivo effects of various antibodies on whole blood. hL243γ4P resulted in significantly less B cell depletion than rituximab and veltuzumab, consistent with an earlier report (Nagy, et al, J Mol Med 2003; 81:757-65) which suggested that anti-HLA-DR mAbs kill activated, but not resting normal B cells, in addition to tumor cells. This suggests a dual requirement for both MHC-II expression and cell activation for antibody-induced death, and implies that because the majority of peripheral B cells are resting, the potential side effect due to killing of normal B cells may be minimal. T-cells are unaffected.

The effects of ERK, JNK and ROS inhibitors on hL243γ4P mediated apoptosis in Raji cells is shown in FIG. 28. hL243γ4P cytotoxicity correlates with activation of ERK and JNK signaling and differentiates the mechanism of action of hL243γ4P cytotoxicity from that of anti-CD20 mAbs. hL243γ4P also changes mitochondrial membrane potential and generates ROS in Raji cells (not shown). Inhibition of ERK, JNK, or ROS by specific inhibitors partially abrogates the apoptosis. Inhibition of 2 or more pathways abolishes the apoptosis.

These data demonstrate that hL243g4P may be useful in the treatment of mantle cell lymphoma, ALL, hairy cell leukemia, and CLL, as well as NHL and multiple myeloma.

Example 9. Purification of hL243 Anti-HLA-DR Antibody

The hL243 anti-HLA-DR antibody was designed, constructed, cloned and transfected into myeloma host cells as described in U.S. Pat. No. 7,612,180, the Examples section of which is incorporated herein by reference.

The purification process for hL243 IgG featured chromatography on three sequential columns of Protein A, Q-SEPHAROSE® and SP-SEPHAROSE®. Although SEPHAROSE® is used as an exemplary column chromatography resin, the skilled artisan will realize that alternative methods of chromatography and alternative chromatography resins are known in the art and may be used. Further, the anion and cation exchange steps are not limited to Q-SEPHAROSE® and SP-SEPHAROSE®, but may also utilize other anion- and cation-exchange resins known in the art. The last step of the process utilizes a DV20 virus removal filtration, after which the product is tested for sterility.

The Protein A affinity resin used for the first column, MABSELECT™ (GE Healthcare, Piscataway, N.J.) has a binding capacity of 25-30 mg/mL. The resin was packed up to a 20 cm height in a 20 cm diameter column to a packed bed volume of 6.3 L, with a maximum loading capacity of 220 gm. Before the antibody containing culture medium was loaded, the packed column was sanitized with 0.1 M acetic acid in 20% ethanol and then re-generated with 0.04 M PBS, pH 7.4. After equilibration, the supernatant was loaded at a maximum flow rate of 300 cm/hr. The column was washed with 0.04 M PBS, pH 7.4, until the absorbance returned to baseline, followed by washing with another 5 bed volumes of 0.04 M PBS, pH 7.4 at 300 cm/hr.

The bound IgG was eluted with 0.1 M citrate, pH 3.5, at a maximum flow rate of 300 cm/hr. The elution profile was monitored by absorbance at 280 nm, using a flow through spectrophotometer. The collected product peak was neutralized to pH 7.0-8.0 using 3 M Tris/HCl, pH 8.6. As an additional virus removal step, the neutralized product peak was titrated to pH 3.5-3.7 using 1 M citric acid. This mixture was incubated at room temperature for four hours and at the end of the incubation, it was neutralized to pH 7.0-8.0 using 3 M Tris/HCl, pH 8.6.

The mixture was then concentrated to 5-7 mg/mL and diafiltered into 0.02 M Tris/HCl, 0.05 M NaCl, pH 7.5, in preparation for the next purification step. The diafiltered Protein A purified hLL2 IgG was filtered through a 0.2 µm filter and stored at 2-8° C., before loading onto the Q-SEPHAROSE® column.

The anion exchange resin used for the next column was Q-SEPHAROSE® fast flow resin (GE Healthcare, Piscataway, N.J.). The resin was packed up to a 20 cm height in a 30 cm diameter column, to a packed bed volume of 14.1 L with a maximum loading capacity of 300 gm. Before the Protein A purified IgG was loaded, the packed column was sanitized with 1 M sodium hydroxide and then regenerated with 0.02 M Tris/HCl, 1.0 M NaCl, pH 8.0. The resin was then equilibrated with 0.02 M Tris/HCl, 0.05 M NaCl, pH 7.5. The diafiltered Protein A purified IgG was loaded at a flow rate of 100 cm/hr and the flow through peak was eluted with 0.02 M Tris/HCl, 0.05 M NaCl, pH 7.5 at a maximum flow rate of 300 cm/hr. The contaminants eluted from the Protein A column bound to the Q-SEPHAROSE® resin. The Q-SEPHAROSE® purified IgG was filtered using a 0.2-µm filter and stored at 2-8° C. until further purification. Before loading onto the final column, the IgG was titrated to pH 5.0 using 1 M citric acid.

The cation exchange resin used for the last column was SP-SEPHAROSE® fast flow resin (GE Healthcare, Piscataway, N.J.). The resin was packed up to a 20 cm height in a 20 cm diameter column, with a maximum loading capacity of 220 gm. Before the Q-SEPHAROSE® purified hLL2 IgG was loaded, the packed column was sanitized with 1 M sodium hydroxide and then equilibrated with 0.025 M citrate, pH 5.0. The IgG was loaded at a maximum flow rate of 300 cm/hr and the column was washed with 5 bed volumes of 0.025 M citrate, pH 5.0, at 300 cm/hr. After loading and washing, the IgG was eluted with 0.025 M citrate, 0.15 M NaCl, pH 6.0. The elution profile was monitored by absorbance at 280 nm.

The purified hL243 IgG was concentrated to 10-11 mg/mL and diafiltered into 0.04 M PBS, pH 7.4, then filtered through 0.2 and 0.1 µm filters before $DV_{20}$ filtration. After filtration, 75 mL of 0.04 M PBS, 1% Polysorbate 80, pH 7.4 was added to every liter of purified IgG and the mixture was filtered again through a 0.2 µm filter before storage at 2°-8° C.

Example 10. Ultrafiltration Concentration of Humanized Antibodies in High Concentration Formulation Buffer Using ultrafiltration, humanized IgG was concentrated to at least 200 mg/mL in High Concentration Formulation (HCF) buffer, with minimal or no aggregation. A series of analytical assays were performed to monitor any changes during the concentration process. No detectable changes in antibody quality or solution characteristics were observed. The liquid formulation was stable at 2-8° C. for at least 12 months. The stability estimated at 12 months by SE-HPLC (which showed essentially a single peak on the absorbance trace) was between 97 and 99%. Reducing and non-reducing PAGE was consistent with the HPLC results (not shown). The formulation is suitable for subcutaneous injection (SQ). Exemplary antibodies tested include milatuzumab (hLL1, anti-CD74), epratuzumab (hLL2, anti-CD22), veltuzumab (hA20, anti-CD20) and hL243 (anti-HLA-DR; IMMU-114).

A High Concentration Formulation (HCF) buffer was developed that was demonstrated to be capable of stabilizing antibody solutions to at least 200 mg/mL concentration (Table 16). In addition to phosphate buffer and NaCl from IV formulation, this SQ formulation contains mannitol which has been of use in protein formulations for maintaining stability and isotonicity, and Polysorbate 80 (PS-80) which protects antibodies against aggregation. Since the pI value of most humanized IgG1 antibodies is between 8-9.5, a citric acid/sodium citrate buffer system (buffering range 2.5-5.6) and a low pH (5.2) were used to ensure the protein is in charged form, and thus more stable in solution.

During ultrafiltration a 50 KD MW cut-off membrane was used, which retained and concentrated the 150 kD IgG molecules while allowing water and small molecules in the formulation buffer to pass through.

TABLE 16

High Concentration Formulation Compositions

| Component | hLL1 (Milatuzumab, anti-CD74) | hLL12 (Epratuzumab, anti-CD22) | hA20 (Veltuzumab, anti-CD20) | hL243 (anti-HLA-DR) |
|---|---|---|---|---|
| $IgG_1$ | 213 mg/mL | 109 mg/mL | 162 mg/ml | 101 mg/mL |
| $Na_2HPO_4 \cdot 7H_2O$ | 2.30 g | | | |
| $NaH_2PO_4 \cdot H_2O$ | 0.76 g | | | |
| Sodium Chloride | 6.16 g | | | |
| Polysorbate 80 (w/v) | 1.0 mL (polysobate-80 was added at the end of the concentration step) | | | |
| Sodium Citrate Dihydrate | 0.34 g | | | |
| Citric Acid Monohydrate | 1.3 g | | | |
| Mannitol | 12.0 g | | | |
| WFI (qs) | 1 L | | | |
| pH (adjusted by NaOH) | 5.2 | | | |

The solute concentrations of HCF buffer were 6.2 mM citric acid monohydrate, 105 mM sodium chloride, 1.2 mM sodium citrate dihydrate, 8.7 mM sodium phosphate dibasic, 5.5 mM sodium phosphate monobasic, 66 mM mannitol, pH 5.2, conductivity 11.0-14.0 mS/cm.

An AMICON® Model 8050 Stirred Ultrafiltration Cell (from MILLIPORE®, 50 mL max volume) was used with a 50 kD polyethersulfone filter NMWL (from MILLIPORE®, diameter 44.5 mm) to concentrate the antibodies. Ultra pure argon gas was used to pressurize the system.

The UF-cell with a 50 KD membrane was assembled and connected to the argon gas supply. The cell was rinsed and filled with buffer. With the stirrer on, pressure was applied to run more than two volumes of HCF buffer through the membrane. From this point on, the membrane was maintained in a wet state.

After rinsing of the stirred cell chamber, the residual buffer was discarded and the cell was filled with IgG solution. The stir plate was then started and the pressure applied. The antibody solution was concentrated to approximately one half (½) the original volume, then diafiltered using HCF buffer (5× retentate volume). The process was repeated 3-4 times until the diafiltration was completed and checked to make sure that the pH and conductivity of filtrate was identical to the HCF buffer.

Post-concentration, Polysobate-80 was added so that the final concentration of Polysorbate was 0.1%. The IgG was then filtered through a 0.22-μm filter, placed in clear glass vials, and stored at 2-8° C. until analytical testing was performed.

Each sample was visually inspected against a dark background under light for any particulates and precipitates. IgG protein concentration was measured by UV ($OD_{280}$) absorbance after serial dilutions. SDS-PAGE was performed using pre-cast 4-20% gradient gels. Ten μL of ~1 mg/mL sample was heated at 95° C. for 3 minutes in the presence (reducing gel) or absence (non-reducing gel) of a 3% 2-mercaptoethanol solution. Gels were stained with 0.1% Coomassie Blue. Isoelectric Focusing (IEF) was performed by standard techniques, using pH 6-10.5 gradient gels. Samples were diluted to 2 mg/mL and applied at 5 μL each along with pI markers and reference standard. Gels were stained with Coomassie Blue and scanned for quantification of pI range.

Size Exclusion HPLC (SE-HPLC) was carried out using a BECKMAN® HPLC system (Model 116), with a BIO-SIL® SEC 250 column. The sample was diluted to about 1 mg/mL and 60 μL was injected. The elution buffer was composed of 0.05 M $NaH_2PO_4$, 0.05 M $Na_2HPO_4$ and 1 mM EDTA, pH 6.8. The elution was monitored by UV absorbance at 280 nm.

All analytical results are summarized in Table 17. The SDS-PAGE gel, IEF gel, and SE-HPLC chromatograms are not shown. Ultrafiltration concentration of the IgG in HCF buffer from 101 mg/mL to 213 mg/mL did not result in any detectable changes in the purified IgG.

TABLE 17

Analytical Results

| Antibody Concentration | hLL1 213 mg/mL | hLL2 109 mg/mL | hA20 102 mg/mL | hL243 101 mg/mL |
|---|---|---|---|---|
| SE-HPLC (Area Percent) | 98.3% (0 month) 97.5% (4 month) | 98.5 % (0 Month) 97.3% (12 Month) | 98.9% (0 Month) 98.5% (12 Month) | 99.3% (0 Month) 98.8% (12 Month) |
| Visual inspection | Clear yellowish color | Clear yellowish color | Clear yellowish color | Clear slight milk color |
| SDS-Page gel | Reducing and Non-Reducing SDS-PAGE gels for all samples of concentrated MAb showed a band pattern similar to reference standard | | | |
| IEF gel | IEF gel patterns for all samples of concentrated MAb showed a band pattern similar to reference standard | | | |

This study demonstrated that in the HCF buffer, IgG could be concentrated by ultrafiltration up to 213 mg/mL without any visible aggregation or precipitation. Other quality aspects of the antibody such as molecular integrity, charge variation and solution pH were also maintained.

Example 11. High-Protein Concentration Antibody Formulations for Subcutaneous or Intramuscular Injection Alternative high concentration formulations for subcutaneous or intramuscular administration may comprise amino acids, such as arginine or glutamine. A comparison of the maximal protein concentration achievable without precipitation was determined for epratuzumab (humanized anti-CD22), using three different formulations comprising the sugar mannitol and/or the amino acids arginine and glutamic acid (Table 18).

Epratuzumab was applied to a 40 mL MABSELECT® (Protein A) affinity chromatography column, which was washed with phosphate-buffered saline and then diH$_2$O, to remove polysorbate-80 from the original bulk material. The antibody was eluted with 80 mL of 0.05 M sodium citrate, pH 3.5. The eluate was neutralized by the addition of 132 mL of 0.1 M NaH$_2$PO$_4$ and formulated into CPREM buffer by the addition of 60 mL of a 1 M L-arginine monohydrochloride/1 M L-glutamic acid (monosodium salt) solution and 39.6 mL of 1 M mannitol, adjusted to pH 5.3 with HCl and diluted to 600 mL with deionized H$_2$O. The final CPREM formulation contained 66 mM mannitol, 100 mM arginine, 100 mM glutamic acid, 144 mM Na, 100 mM Cl, 7.3 mM citrate, 22 mM phosphate, pH 5.3. A protein concentration of 2.56 mg/mL was measured by UV spectrophotometry at 280 nM (OD$_{280}$).

The 600 mL solution was concentrated 120-fold using a stir-cell concentrator with a 50 kDa MWCO membrane. A protein concentration of 238 mg/mL in the 120× concentrate was measured by OD$_{280}$. There was no evident precipitation by visual inspection and an SE-HPLC trace, which was indistinguishable from that of the pre-concentration material, showed no evidence of aggregation (data not shown). The 120-fold concentrate was separated into three aliquots.

An aliquot (0.5 mL) of the 120× concentrate (238 mg/mL) was maintained in the CPREM formulation and further concentrated to 170× (0.35 mL) and measured by 0D$_{280}$ at a protein concentration of 298 mg/mL without evident precipitation. SE-HPLC analysis resolved an identical trace to the pre-concentration material with no aggregation (data not shown). Further concentration of the 30% protein solution was not attempted due to high viscosity and limiting volumes.

A second aliquot was diafiltered into CPRE buffer (100 mM arginine, 100 mM glutamic acid, 144 mM Na, 100 mM Cl, 7.3 mM citrate, 22 mM phosphate, pH 5.3.), which is CPREM buffer without mannitol. The CPRE protein solution was concentrated until a precipitate was evident. At this point, concentration was terminated and the solution was filtered. The protein concentration in the filtered concentrate was measured at 99 mg/mL by OD$_{280}$.

The third aliquot was diafiltered into CPM buffer (66 mM mannitol, 144 mM Na, 100 mM Cl, 7.3 mM citrate, 22 mM phosphate, pH 5.3.), which is CPREM without arginine and glutamic acid. The CPM protein solution was concentrated until a precipitate was evident. At this point, concentration was terminated and the solution was filtered. The protein concentration in the filtered concentrate was measured at 137 mg/mL by OD$_{280}$.

These results suggest that addition of arginine and glutamic acid to the HCF buffer increased the maximum concentration of antibody that could be maintained without precipitation, up to at least 300 mg/ml. Further, since maximum concentration of the hLL1 antibody that could be obtained in HCF buffer was no higher than observed with the other tested antibodies, and substantially lower than observed with the hLL1 antibody in HCF buffer, it is expected that comparable increases in stable antibody concentration without precipitation may be obtained for other highly concentrated antibodies.

TABLE 18

High-concentration epratuzumab formulations

| Formulation | Arginine (mM) | Glutamic Acid (mM) | Mannitol (mM) | C$_{max}$ (mg/L) |
|---|---|---|---|---|
| CPREM | 100 | 100 | 66 | 298‡ |
| CPRE | 100 | 100 | 0 | 99* |
| CPM | 0 | 0 | 66 | 137* |

Each formulation contained 144 mM Na, 100 mM Cl, 7.3 mM citrate, 22 mM PO$_4$, pH 5.3
C$_{max}$, maximal achievable concentration at the point of protein precipitation‡ or limiting viscosity*

Example 12. Subcutaneous Injection of Low-Dose Veltuzumab in Non-Hodgkin's Lymphoma (NHL)

Veltuzumab was prepared for subcutaneous administration as described above. Seventeen patients with previously untreated or relapsed NHL received 4 doses of 80, 160 or 320 mg veltuzumab injected s.c. every two weeks (Negrea et al., 2011, Haematologica 96:567-573). Responses were assessed by CT scans, with other evaluations including adverse event, B-cell blood levels, serum veltuzumab levels and human anti-veltuzumab (HAHA) titers.

Only occasional, mild to moderate transient injection reactions were seen with the s.c. injection and no other safety issues were observed. The s.c. veltuzumab exhibited a slow release pattern over several days, with mean maximum serum concentrations of 19, 25 and 64 µg/mL at dosages of 80, 160 or 320 mg per injection. Transient B-cell depletion was observed at all dosage levels of veltuzumab. The objective response rate (partial responses plus complete responses plus complete responses unconfirmed) was 47% (8/17) with a complete response/complete response unconfirmed rate of 24% (4/17). Four of the eight objective responses continued for 60 weeks or more. Objective responses were observed at all dose levels of s.c. veltuzumab. All serum samples evaluated for human anti-veltuzumab antibody (HAHA) were negative.

It was concluded that subcutaneous injections of low-dose veltuzumab are convenient, well-tolerated and capable of achieving sustained serum levels, B-cell depletion and durable objective responses in indolent non-Hodgkin's lymphoma.

What is claimed is:

1. A method of treating an HLA-DR positive hematologic cancer comprising administering by subcutaneous injection a dosage of anti-HLA-DR antibody to a human patient with an HLA-DR positive hematologic cancer selected from the group consisting of DLBCL (diffuse large B-cell lymphoma), follicular lymphoma, non-Hodgkin's lymphoma, CLL (chronic lymphocytic leukemia), and Burkitt lymphoma, wherein the anti-HLA-DR antibody is a humanized antibody comprising the heavy chain CDR sequences NYGMN (SEQ ID NO: 39), WINTYTREPTYADDFKG (SEQ ID NO: 40), and DITAVVPTGFDY (SEQ ID NO: 41) and the light chain CDR sequences RASENIYSNLA (SEQ ID NO: 42), AASNLAD (SEQ ID NO: 43), and QHFWTTPWA (SEQ ID NO: 44), wherein the humanized anti-HLA-DR antibody comprises the light chain murine L243 FR residues R37, K39, V48, F49, and G100 and heavy chain murine L243 FR residues F27, K38, K46, A68, and F91, and wherein the patient has failed at least one prior therapy for the hematologic cancer.

2. The method of claim 1, wherein administration by subcutaneous injection does not induce infusion-related toxicity.

3. The method of claim 1, wherein the patient has failed therapy with an anti-CD20 antibody, prior to administration of the anti-HLA-DR antibody.

4. The method of claim 3, wherein the patient has failed therapy with rituximab, prior to administration of the anti-HLA-DR antibody.

5. The method of claim 1, wherein the patient who has failed at least one prior therapy responds to the subcutaneous anti-HLA-DR antibody.

6. The method of claim 1, wherein the cancer is recurrent NHL (non-Hodgkin's lymphoma), relapsed NHL or CLL (chronic lymphocytic leukemia).

7. The method of claim 1, wherein the dosage of anti-HLA-DR antibody administered to the patient is 150, 200, 250 or 300 mg.

8. The method of claim 1, wherein the anti-HLA-DR antibody comprises a human heavy chain γ4 constant region sequence with a Ser241Pro substitution.

9. The method of claim 1, wherein the anti-HLA-DR antibody is a naked antibody.

* * * * *

SEQUENCE LISTING

```
<160> NUMBER OF SEQ ID NOS: 46

<210> SEQ ID NO 1
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1
```

```
Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Ile Glu Tyr Leu Ala Lys Gln Ile Val Asp Asn Ala Ile Gln Gln
1               5                   10                  15

Ala

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 5
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: Any conservative amino acid substitution
<220> FEATURE:
<221> NAME/KEY: MOD_RES
<222> LOCATION: (4)..(4)
<223> OTHER INFORMATION: Any conservative amino acid substitution
```

```
<220> FEATURE:
<221> NAME/KEY: MOD_RES
<222> LOCATION: (6)..(8)
<223> OTHER INFORMATION: Any conservative amino acid substitution
<220> FEATURE:
<221> NAME/KEY: MOD_RES
<222> LOCATION: (10)..(11)
<223> OTHER INFORMATION: Any conservative amino acid substitution
<220> FEATURE:
<221> NAME/KEY: MOD_RES
<222> LOCATION: (14)..(15)
<223> OTHER INFORMATION: Any conservative amino acid substitution
<220> FEATURE:
<221> NAME/KEY: MOD_RES
<222> LOCATION: (17)..(17)
<223> OTHER INFORMATION: Any conservative amino acid substitution
<220> FEATURE:
<221> NAME/KEY: MOD_RES
<222> LOCATION: (19)..(19)
<223> OTHER INFORMATION: Any conservative amino acid substitution
<220> FEATURE:
<221> NAME/KEY: MOD_RES
<222> LOCATION: (22)..(27)
<223> OTHER INFORMATION: Any conservative amino acid substitution
<220> FEATURE:
<221> NAME/KEY: MOD_RES
<222> LOCATION: (30)..(30)
<223> OTHER INFORMATION: Any conservative amino acid substitution
<220> FEATURE:
<221> NAME/KEY: MOD_RES
<222> LOCATION: (32)..(32)
<223> OTHER INFORMATION: Any conservative amino acid substitution
<220> FEATURE:
<221> NAME/KEY: MOD_RES
<222> LOCATION: (34)..(34)
<223> OTHER INFORMATION: Any conservative amino acid substitution
<220> FEATURE:
<221> NAME/KEY: MOD_RES
<222> LOCATION: (37)..(38)
<223> OTHER INFORMATION: Any conservative amino acid substitution
<220> FEATURE:
<221> NAME/KEY: MOD_RES
<222> LOCATION: (40)..(44)
<223> OTHER INFORMATION: Any conservative amino acid substitution

<400> SEQUENCE: 5

Xaa Xaa Ile Xaa Ile Xaa Xaa Xaa Leu Xaa Xaa Leu Leu Xaa Xaa Tyr
1               5                   10                  15

Xaa Val Xaa Val Leu Xaa Xaa Xaa Xaa Xaa Xaa Leu Val Xaa Phe Xaa
            20                  25                  30

Val Xaa Tyr Phe Xaa Xaa Leu Xaa Xaa Xaa Xaa Xaa
        35                  40

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any conservative amino acid substitution
<220> FEATURE:
<221> NAME/KEY: MOD_RES
<222> LOCATION: (7)..(8)
<223> OTHER INFORMATION: Any conservative amino acid substitution
<220> FEATURE:
<221> NAME/KEY: MOD_RES
<222> LOCATION: (11)..(12)
<223> OTHER INFORMATION: Any conservative amino acid substitution
<220> FEATURE:
<221> NAME/KEY: MOD_RES
<222> LOCATION: (15)..(17)
```

<223> OTHER INFORMATION: Any conservative amino acid substitution

<400> SEQUENCE: 6

Xaa Xaa Xaa Xaa Xaa Ala Xaa Xaa Ile Val Xaa Xaa Ala Ile Xaa Xaa
1               5                   10                  15

Xaa

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Ile Glu Tyr Val Ala Lys Gln Ile Val Asp Tyr Ala Ile His Gln
1               5                   10                  15

Ala

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Ile Glu Tyr Lys Ala Lys Gln Ile Val Asp His Ala Ile His Gln
1               5                   10                  15

Ala

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Ile Glu Tyr His Ala Lys Gln Ile Val Asp His Ala Ile His Gln
1               5                   10                  15

Ala

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ile Glu Tyr Val Ala Lys Gln Ile Val Asp His Ala Ile His Gln
1               5                   10                  15

Ala

<210> SEQ ID NO 11
<211> LENGTH: 24
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 11

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Glu Gln Tyr Ala Asn Gln Leu Ala Asp Gln Ile Ile Lys Glu Ala
1               5                   10                  15

Thr Glu

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Glu Glu Leu Ala Trp Lys Ile Ala Lys Met Ile Trp Ser Asp Val
1               5                   10                  15

Phe Gln Gln Cys
            20

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25
```

```
<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any conservative amino acid substitution
<220> FEATURE:
<221> NAME/KEY: MOD_RES
<222> LOCATION: (4)..(4)
<223> OTHER INFORMATION: Any conservative amino acid substitution
<220> FEATURE:
<221> NAME/KEY: MOD_RES
<222> LOCATION: (7)..(7)
<223> OTHER INFORMATION: Any conservative amino acid substitution
<220> FEATURE:
<221> NAME/KEY: MOD_RES
<222> LOCATION: (10)..(10)
<223> OTHER INFORMATION: Any conservative amino acid substitution
<220> FEATURE:
<221> NAME/KEY: MOD_RES
<222> LOCATION: (18)..(18)
<223> OTHER INFORMATION: Any conservative amino acid substitution
<220> FEATURE:
<221> NAME/KEY: MOD_RES
<222> LOCATION: (23)..(23)
<223> OTHER INFORMATION: Any conservative amino acid substitution
<220> FEATURE:
<221> NAME/KEY: MOD_RES
<222> LOCATION: (26)..(26)
<223> OTHER INFORMATION: Any conservative amino acid substitution
<220> FEATURE:
<221> NAME/KEY: MOD_RES
<222> LOCATION: (33)..(34)
<223> OTHER INFORMATION: Any conservative amino acid substitution
<220> FEATURE:
<221> NAME/KEY: MOD_RES
<222> LOCATION: (37)..(38)
<223> OTHER INFORMATION: Any conservative amino acid substitution
<220> FEATURE:
<221> NAME/KEY: MOD_RES
<222> LOCATION: (40)..(40)
<223> OTHER INFORMATION: Any conservative amino acid substitution
<220> FEATURE:
<221> NAME/KEY: MOD_RES
<222> LOCATION: (42)..(42)
<223> OTHER INFORMATION: Any conservative amino acid substitution
<220> FEATURE:
<221> NAME/KEY: MOD_RES
<222> LOCATION: (44)..(44)
<223> OTHER INFORMATION: Any conservative amino acid substitution

<400> SEQUENCE: 17

Xaa His Ile Xaa Ile Pro Xaa Gly Leu Xaa Glu Leu Leu Gln Gly Tyr
1               5                   10                  15

Thr Xaa Glu Val Leu Arg Xaa Gln Pro Xaa Asp Leu Val Glu Phe Ala
```

```
                20                  25                  30
Xaa Xaa Tyr Phe Xaa Xaa Leu Xaa Glu Xaa Arg Xaa
            35                  40

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Lys Ser Leu Ser Leu Ser Pro Gly Leu Gly Ser Gly Gly Gly Gly
1               5                   10                  15

Ser Gly Gly Cys Gly
            20

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Lys Ser Leu Ser Leu Ser Pro Gly Ala Gly Ser Gly Gly Gly Gly
1               5                   10                  15

Ser Gly Gly Cys Gly
            20

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Lys Ser Leu Ser Leu Ser Pro Gly Gly Ser Gly Gly Gly Gly Ser
1               5                   10                  15

Gly Gly Cys Gly
            20

<210> SEQ ID NO 21
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
ggtctgagtt gaagaagcct ggggcctcag tgaaggtttc ctgcaaggct tctggattta      60
ccttcacaaa ctatggaatg aactgggtga agcaggcccc tggacaaggg cttaagtgga     120
tgggctggat aaacacctac actagagagc aacatatgc tgatgacttc aaggg           175

<210> SEQ ID NO 22
<211> LENGTH: 168
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 22 accccttggcc ccagtagtca aaacccgtag gtacaaccgc agtaatatct cttgcacaga    60
aatacacggc agtgtcgtca gcctttaggc tgctgatctg gagatatgcc gtgctgacag   120
aggtgtccaa ggagaaggca aaccgtccct tgaagtcatc agcatatg                168

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
gtggtgctgc agcaatctgg gtctgagttg aagaagcc                             38

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
tgaggagacg gtgaccaggg acccttggcc ccagtagt                             38

<210> SEQ ID NO 25
<211> LENGTH: 155
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 25
tccatcatct ctgagcgcat ctgttggaga tagggtcact atcacttgtc gagcaagtga    60
gaatatttac agtaatttag catggtatcg tcagaaacca gggaaagcac ctaaactgct   120
ggtctttgct gcatcaaact tagcagatgg tgtgc                              155

<210> SEQ ID NO 26
<211> LENGTH: 159
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 26
cagcttggtc cctccaccga acgcccacgg agtagtccaa aaatgttgac aataatatgt    60
tgcaatgtct tctggttgaa gagagctgat ggtgaaagta taatctgtcc cagatccgct   120
gccagagaat cgcgaaggca caccatctgc taagtttga                          159

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27
gacattcagc tgacccagtc tccatcatct ctgagcgc                                   38

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ccggcagatc tgcagcttgg tccctccacc g                                          31

<210> SEQ ID NO 29
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccgcggtcac atggcaccac ctctcttgca gcttccacca agggccc                         47

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccggccgtcg cactcattta cccagagaca ggg                                        33

<210> SEQ ID NO 31
<211> LENGTH: 324
<212> TYPE: DNA
<213> ORGANISM: Mus musculus
<220> FEATURE:
<221> NAME/KEY: CDS
<222> LOCATION: (1)..(323)

<400> SEQUENCE: 31

```
gac atc cag atg act cag tct cca gcc tcc cta tct gta tct gtg gga         48
Asp Ile Gln Met Thr Gln Ser Pro Ala Ser Leu Ser Val Ser Val Gly
1               5                   10                  15 gaa act gtc acc atc aca tgt cga gca agt gag aat att tac agt aat         96
Glu Thr Val Thr Ile Thr Cys Arg Ala Ser Glu Asn Ile Tyr Ser Asn
                20                  25                  30 tta gca tgg tat cgt cag aaa cag gga aaa tct cct cag ctc ctg gtc        144
Leu Ala Trp Tyr Arg Gln Lys Gln Gly Lys Ser Pro Gln Leu Leu Val
            35                  40                  45 ttt gct gca tca aac tta gca gat ggt gtg cca tca agg ttc agt ggc        192
Phe Ala Ala Ser Asn Leu Ala Asp Gly Val Pro Ser Arg Phe Ser Gly
        50                  55                  60 agt gga tca ggc aca cag tat tcc ctc aag atc aac agc ctg cag tct        240
Ser Gly Ser Gly Thr Gln Tyr Ser Leu Lys Ile Asn Ser Leu Gln Ser
65                  70                  75                  80 gaa gat ttt ggg gat tat tac tgt caa cat ttt tgg act act ccg tgg        288
Glu Asp Phe Gly Asp Tyr Tyr Cys Gln His Phe Trp Thr Thr Pro Trp
                85                  90                  95
```

```
gcg ttc ggt gga ggc acc aac ctg gaa atc aaa cgt          324
Ala Phe Gly Gly Gly Thr Asn Leu Glu Ile Lys Arg
        100                 105
```

<210> SEQ ID NO 32
<211> LENGTH: 108
<212> TYPE: PRT
<213> ORGANISM: Mus musculus

<400> SEQUENCE: 32

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Arg Gln Lys Gln Gly Lys Ser Pro Gln Leu Leu Val
        35                  40                  45

Phe Ala Ala Ser Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Asp Tyr Tyr Cys Gln His Phe Trp Thr Thr Pro Trp
                85                  90                  95

Ala Phe Gly Gly Gly Thr Asn Leu Glu Ile Lys Arg
            100                 105
```

<210> SEQ ID NO 33
<211> LENGTH: 363
<212> TYPE: DNA
<213> ORGANISM: Mus musculus
<220> FEATURE:
<221> NAME/KEY: CDS
<222> LOCATION: (1)..(363)

<400> SEQUENCE: 33

```
cag atc cag ttg gtg cag tct gga cct gag ctg aag aag cct gga gag   48
Gln Ile Gln Leu Val Gln Ser Gly Pro Glu Leu Lys Lys Pro Gly Glu
1               5                   10                  15 aca gtc aag atc tcc tgc aag gct tct ggg ttt acc ttc aca aac tat   96
Thr Val Lys Ile Ser Cys Lys Ala Ser Gly Phe Thr Phe Thr Asn Tyr
            20                  25                  30 gga atg aac tgg gtg aag cag gct cca gga aag ggt tta aag tgg atg   144
Gly Met Asn Trp Val Lys Gln Ala Pro Gly Lys Gly Leu Lys Trp Met
        35                  40                  45 ggc tgg ata aac acc tac act aga gag cca aca tat gct gat gac ttc   192
Gly Trp Ile Asn Thr Tyr Thr Arg Glu Pro Thr Tyr Ala Asp Asp Phe
    50                  55                  60 aag gga cgg ttt gcc ttc tct ttg gaa acc tct gcc agc act gcc tat   240
Lys Gly Arg Phe Ala Phe Ser Leu Glu Thr Ser Ala Ser Thr Ala Tyr
65                  70                  75                  80 ttg cag atc aac aac ctc aaa aat gag gac acg gct aaa tat ttc tgt   288
Leu Gln Ile Asn Asn Leu Lys Asn Glu Asp Thr Ala Lys Tyr Phe Cys
                85                  90                  95 gca aga gat att act gcg gtt gta cct acg ggt ttt gac tac tgg ggc   336
Ala Arg Asp Ile Thr Ala Val Val Pro Thr Gly Phe Asp Tyr Trp Gly
            100                 105                 110 caa ggc acc act ctc acc gtc tcc tca                               363
Gln Gly Thr Thr Leu Thr Val Ser Ser
        115                 120
```

<210> SEQ ID NO 34
<211> LENGTH: 121

```
<212> TYPE: PRT
<213> ORGANISM: Mus musculus

<400> SEQUENCE: 34

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Phe Thr Phe Thr Asn Tyr
             20                  25                  30

Gly Met Asn Trp Val Lys Gln Ala Pro Gly Lys Gly Leu Lys Trp Met
         35                  40                  45

Gly Trp Ile Asn Thr Tyr Thr Arg Glu Pro Thr Tyr Ala Asp Asp Phe
 50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Lys Tyr Phe Cys
             85                  90                  95

Ala Arg Asp Ile Thr Ala Val Val Pro Thr Gly Phe Asp Tyr Trp Gly
            100                 105                 110

Gln Gly Thr Thr Leu Thr Val Ser Ser
            115                 120

<210> SEQ ID NO 35
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(324)

<400> SEQUENCE: 35 gac atc cag ctg acc cag tct cca tca tct ctg agc gca tct gtt gga      48
Asp Ile Gln Leu Thr Gln Ser Pro Ser Ser Leu Ser Ala Ser Val Gly
 1               5                  10                  15 gat agg gtc act atc act tgt cga gca agt gag aat att tac agt aat      96
Asp Arg Val Thr Ile Thr Cys Arg Ala Ser Glu Asn Ile Tyr Ser Asn
             20                  25                  30 tta gca tgg tat cgt cag aaa cca ggg aaa gca cct aaa ctg ctg gtc     144
Leu Ala Trp Tyr Arg Gln Lys Pro Gly Lys Ala Pro Lys Leu Leu Val
         35                  40                  45 ttt gct gca tca aac tta gca gat ggt gtg cct tcg cga ttc tct ggc     192
Phe Ala Ala Ser Asn Leu Ala Asp Gly Val Pro Ser Arg Phe Ser Gly
 50                  55                  60 agc gga tct ggg aca gat tat act ttc acc atc agc tct ctt caa cca     240
Ser Gly Ser Gly Thr Asp Tyr Thr Phe Thr Ile Ser Ser Leu Gln Pro
 65                  70                  75                  80 gaa gac att gca aca tat tat tgt caa cat ttt tgg act act ccg tgg     288
Glu Asp Ile Ala Thr Tyr Tyr Cys Gln His Phe Trp Thr Thr Pro Trp
             85                  90                  95 gcg ttc ggt gga ggg acc aag ctg cag atc aaa cgt                     324
Ala Phe Gly Gly Gly Thr Lys Leu Gln Ile Lys Arg
            100                 105

<210> SEQ ID NO 36
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 36

Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Arg Gln Lys Pro Gly Lys Ala Pro Lys Leu Leu Val
        35                  40                  45

Phe Ala Ala Ser Asn Leu Ala Asp Gly Val Pro Ser Arg Phe Ser Gly
50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Thr Thr Pro Trp
                85                  90                  95

Ala Phe Gly Gly Gly Thr Lys Leu Gln Ile Lys Arg
            100                 105

<210> SEQ ID NO 37
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 37 cag gtg caa ctg cag caa tct ggg tct gag ttg aag aag cct ggg gcc      48
Gln Val Gln Leu Gln Gln Ser Gly Ser Glu Leu Lys Lys Pro Gly Ala
1               5                   10                  15 tca gtg aag gtt tcc tgc aag gct tct gga ttt acc ttc aca aac tat      96
Ser Val Lys Val Ser Cys Lys Ala Ser Gly Phe Thr Phe Thr Asn Tyr
            20                  25                  30 gga atg aac tgg gtg aag cag gcc cct gga caa ggg ctt aag tgg atg     144
Gly Met Asn Trp Val Lys Gln Ala Pro Gly Gln Gly Leu Lys Trp Met
        35                  40                  45 ggc tgg ata aac acc tac act aga gag cca aca tat gct gat gac ttc     192
Gly Trp Ile Asn Thr Tyr Thr Arg Glu Pro Thr Tyr Ala Asp Asp Phe
50                  55                  60 aag gga cgg ttt gcc ttc tcc ttg gac acc tct gtc agc acg gca tat     240
Lys Gly Arg Phe Ala Phe Ser Leu Asp Thr Ser Val Ser Thr Ala Tyr
65                  70                  75                  80 ctc cag atc agc agc cta aag gct gac gac act gcc gtg tat ttc tgt     288
Leu Gln Ile Ser Ser Leu Lys Ala Asp Asp Thr Ala Val Tyr Phe Cys
                85                  90                  95 gca aga gat att act gcg gtt gta cct acg ggt ttt gac tac tgg ggc     336
Ala Arg Asp Ile Thr Ala Val Val Pro Thr Gly Phe Asp Tyr Trp Gly
            100                 105                 110 caa ggg tcc ctg gtc acc gtc tcc tca                                 363
Gln Gly Ser Leu Val Thr Val Ser Ser
        115                 120

<210> SEQ ID NO 38
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Gln Gln Ser Gly Ser Glu Leu Lys Lys Pro Gly Ala
1               5                   10                  15

Ser Val Lys Val Ser Cys Lys Ala Ser Gly Phe Thr Phe Thr Asn Tyr
                20                  25                  30

Gly Met Asn Trp Val Lys Gln Ala Pro Gly Gln Gly Leu Lys Trp Met
            35                  40                  45

Gly Trp Ile Asn Thr Tyr Thr Arg Glu Pro Thr Tyr Ala Asp Asp Phe
        50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Asp Ile Thr Ala Val Val Pro Thr Gly Phe Asp Tyr Trp Gly
                100                 105                 110

Gln Gly Ser Leu Val Thr Val Ser Ser
        115                 120

<210> SEQ ID NO 39
<211> LENGTH: 5
<212> TYPE: PRT
<213> ORGANISM: Mus musculus

<400> SEQUENCE: 39

Asn Tyr Gly Met Asn
1               5

<210> SEQ ID NO 40
<211> LENGTH: 17
<212> TYPE: PRT
<213> ORGANISM: Mus musculus

<400> SEQUENCE: 40

Trp Ile Asn Thr Tyr Thr Arg Glu Pro Thr Tyr Ala Asp Asp Phe Lys
1               5                   10                  15

Gly

<210> SEQ ID NO 41
<211> LENGTH: 12
<212> TYPE: PRT
<213> ORGANISM: Mus musculus

<400> SEQUENCE: 41

Asp Ile Thr Ala Val Val Pro Thr Gly Phe Asp Tyr
1               5                   10

<210> SEQ ID NO 42
<211> LENGTH: 11
<212> TYPE: PRT
<213> ORGANISM: Mus musculus

<400> SEQUENCE: 42

Arg Ala Ser Glu Asn Ile Tyr Ser Asn Leu Ala
1               5                   10

<210> SEQ ID NO 43
<211> LENGTH: 7
<212> TYPE: PRT
<213> ORGANISM: Mus musculus

<400> SEQUENCE: 43

Ala Ala Ser Asn Leu Ala Asp
1               5

<210> SEQ ID NO 44
<211> LENGTH: 9
<212> TYPE: PRT
<213> ORGANISM: Mus musculus

<400> SEQUENCE: 44

Gln His Phe Trp Thr Thr Pro Trp Ala
1               5

<210> SEQ ID NO 45
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 46
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
                305                 310                 315                 320
Gln Lys Ser Leu Ser Leu Ser Pro Gly Lys
                    325                 330
```